(12) United States Patent
Mukhopadhyay

(10) Patent No.: US 11,600,364 B2
(45) Date of Patent: Mar. 7, 2023

(54) MACHINE-LEARNED PHARMACOLOGY OPTIMIZATION

(71) Applicant: Creyon Bio, Inc., San Diego, CA (US)

(72) Inventor: Swagatam Mukhopadhyay, Oceanside, CA (US)

(73) Assignee: Creyon Bio, Inc., San Diego, CA (US)

( * ) Notice: Subject to any disclaimer, the term of this patent is extended or adjusted under 35 U.S.C. 154(b) by 0 days.

(21) Appl. No.: 17/526,775

(22) Filed: Nov. 15, 2021

(65) Prior Publication Data

US 2022/0157409 A1 May 19, 2022

Related U.S. Application Data

(60) Provisional application No. 63/114,389, filed on Nov. 16, 2020.

(51) Int. Cl.
*G16C 20/70* (2019.01)
*G16C 20/30* (2019.01)
*G16C 20/40* (2019.01)
*G16C 20/50* (2019.01)

(52) U.S. Cl.
CPC ............ *G16C 20/70* (2019.02); *G16C 20/30* (2019.02); *G16C 20/40* (2019.02); *G16C 20/50* (2019.02)

(58) Field of Classification Search
CPC ........ G16C 20/70; G16C 20/30; G16C 20/40; G16C 20/50; G16H 50/70; G16H 70/40

USPC ........................................................ 700/2, 3
See application file for complete search history.

(56) References Cited

U.S. PATENT DOCUMENTS

| | | | |
|---|---|---|---|
| 11,075,010 B1 * | 7/2021 | Goswami et al. | G16H 50/70 705/2 |
| 2014/0278130 A1 * | 9/2014 | Bowles et al. | G06F 19/704 702/19 |

OTHER PUBLICATIONS

PCT International Search Report and Written Opinion, PCT Application No. PCT/US2021/059388, dated Feb. 24, 2022, 18 pages.

* cited by examiner

*Primary Examiner* — Thinh T Nguyen
(74) *Attorney, Agent, or Firm* — Fenwick & West LLP

(57) ABSTRACT

Aspects of the present disclosure include methods for optimizing pharmacological compound development and methods for optimizing one or more modifications of a compound. Aspects of the present disclosure further include methods for designing treatments for a disease, and methods for designing optimized candidate compounds to treat a disease that causes one or more disease effects. Aspects of the present disclosure further include computer-implemented methods for training a model for pharmacological compound design, and computer-implemented methods for optimizing chemical modification of pharmacological compounds.

8 Claims, 30 Drawing Sheets

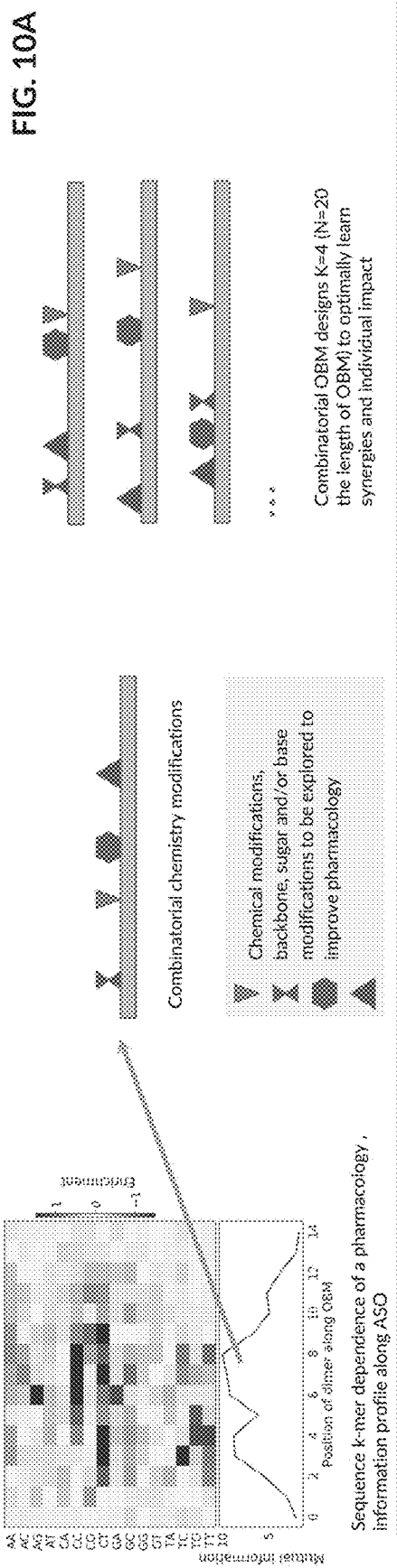
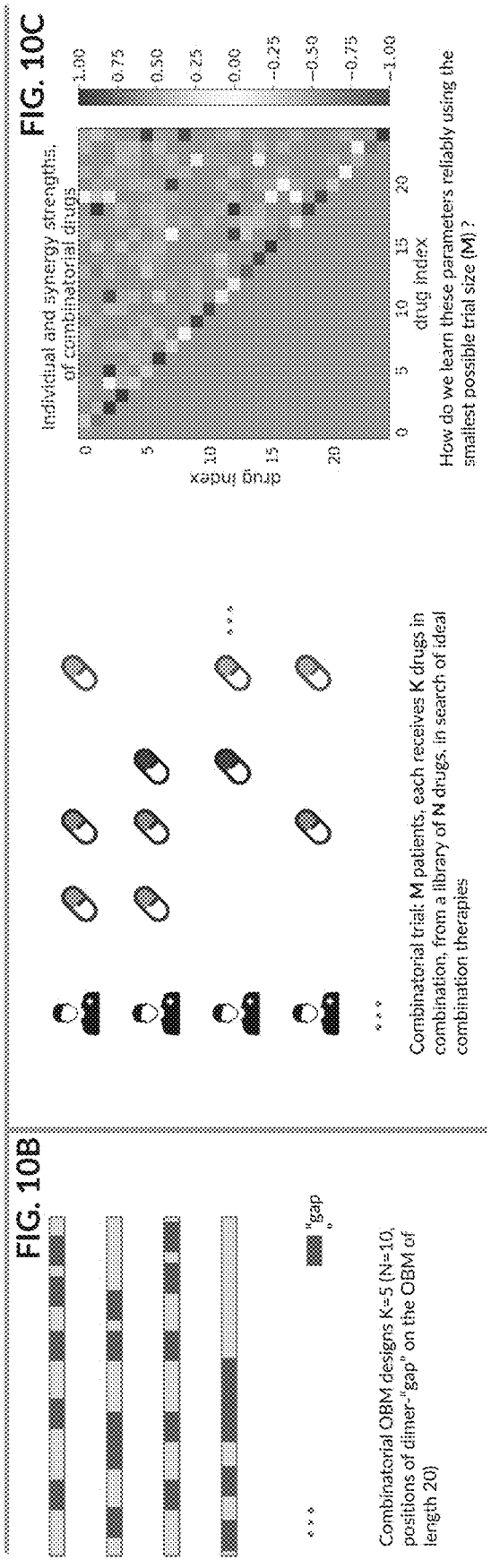
FIG. 10A
FIG. 10B
FIG. 10C

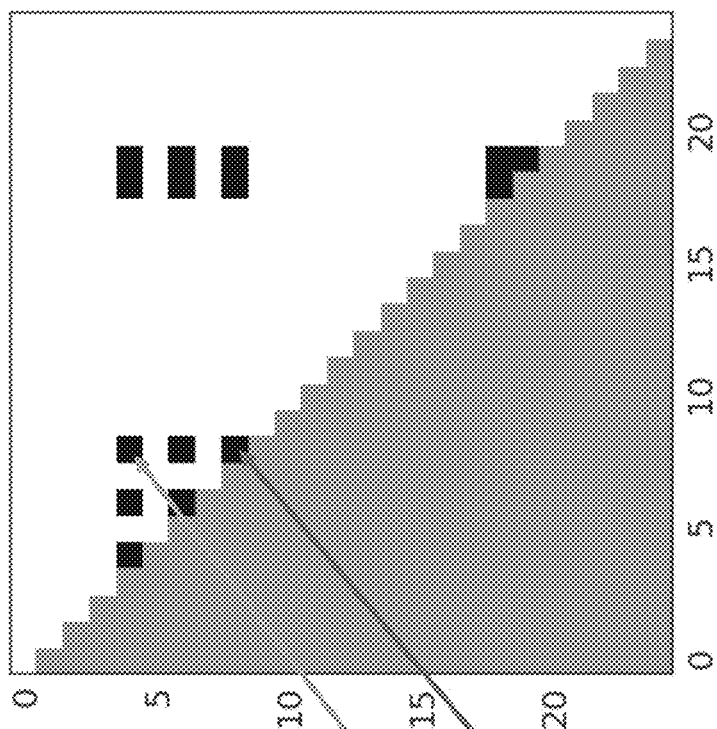

$K = 5, N = 25$

Parameters to learn, N individual (dense) weights
$N \times (N-1)/2$ (sparse) synergy weights = 325

Learned from 180 combination treatments, M = 180

Ground truth: number of nonzero (sparse) synergies + dense parameters modelled = 108

Measurement matrix construction: All pairwise interactions queried exactly 6 times and individual weights queried exactly 36 times

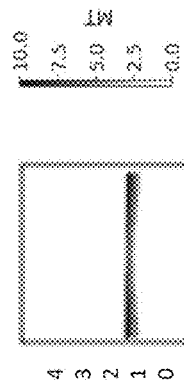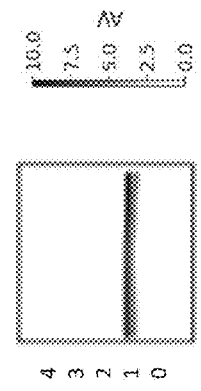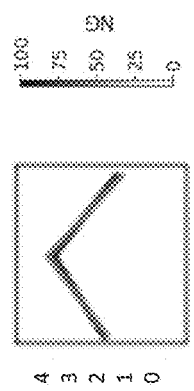
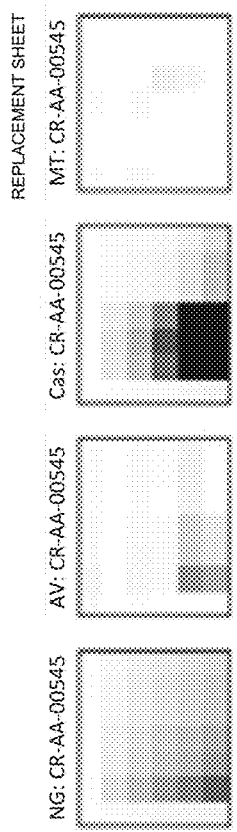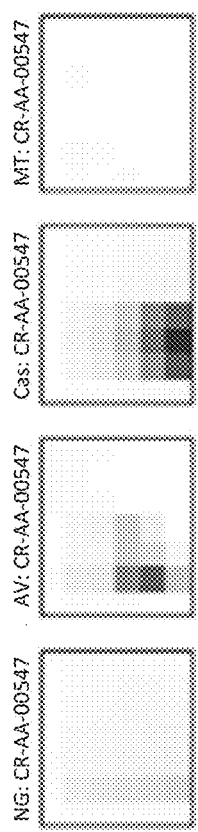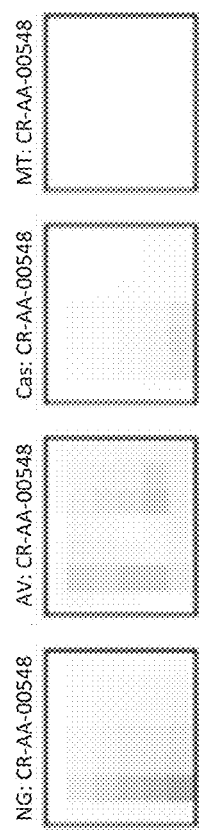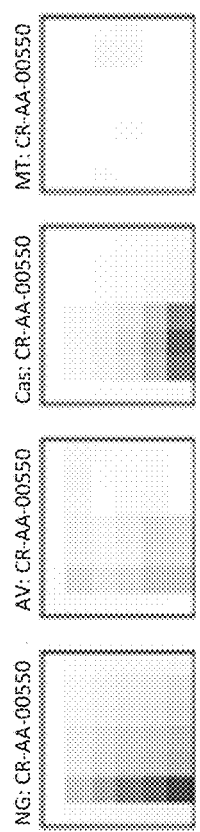
FIG. 14A

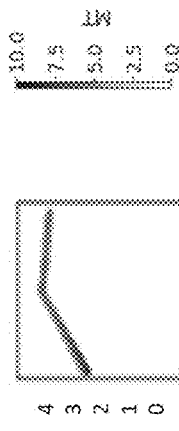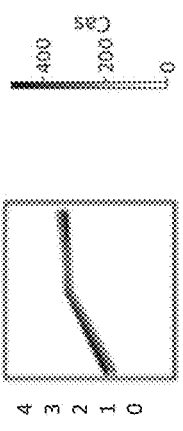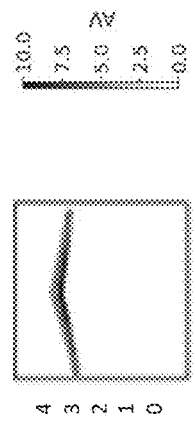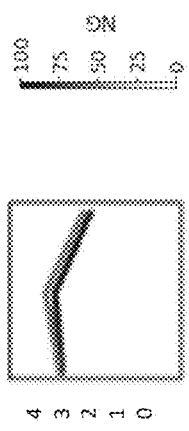
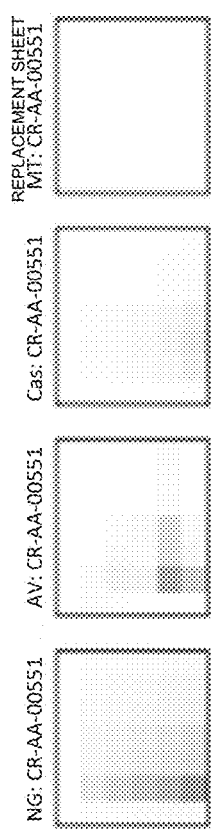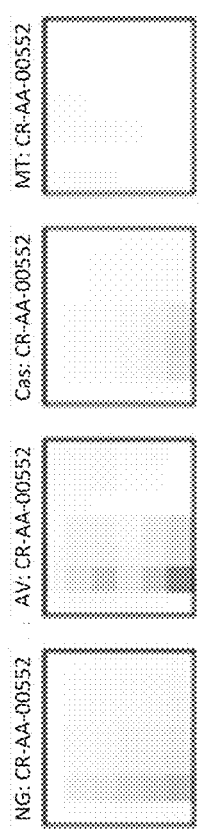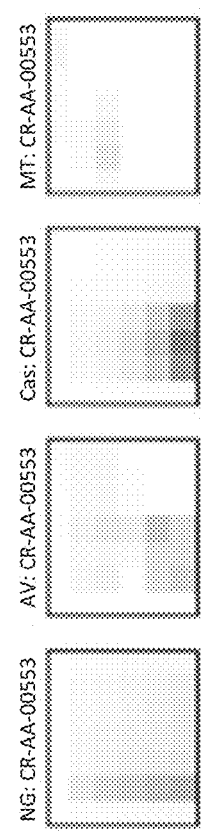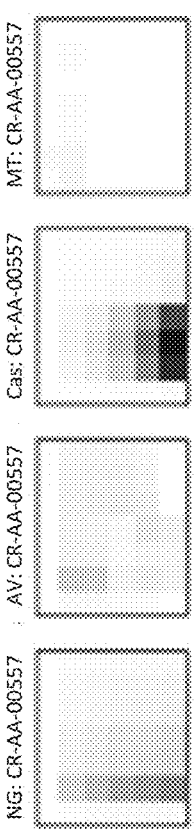
FIG. 14A (continued)

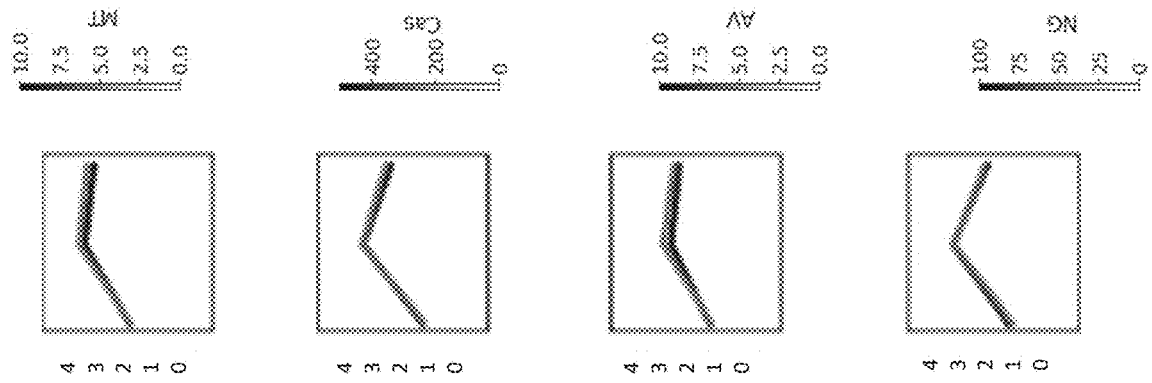
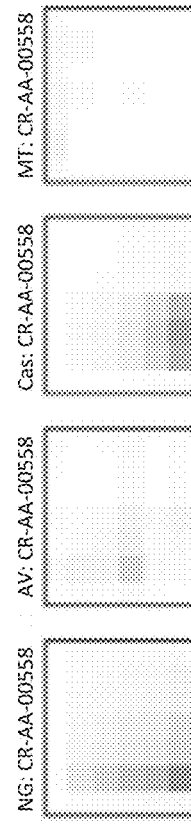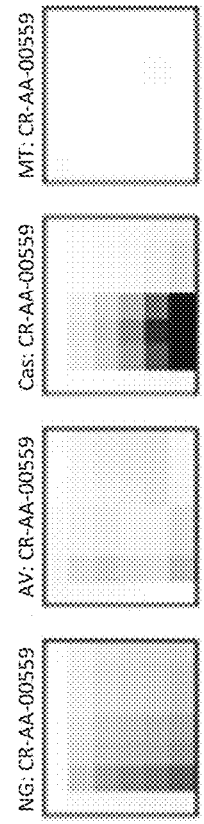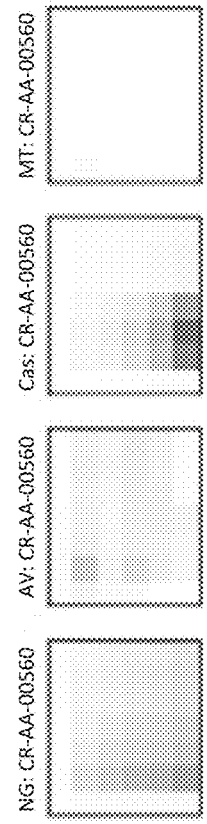
FIG. 14A (continued)

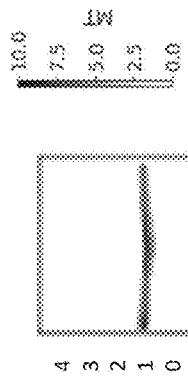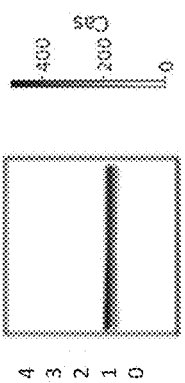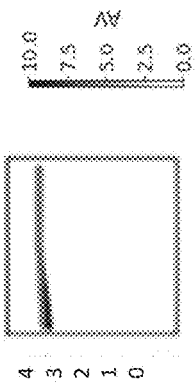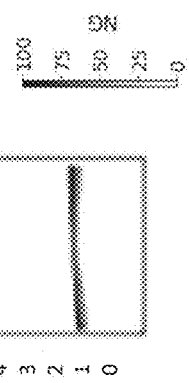
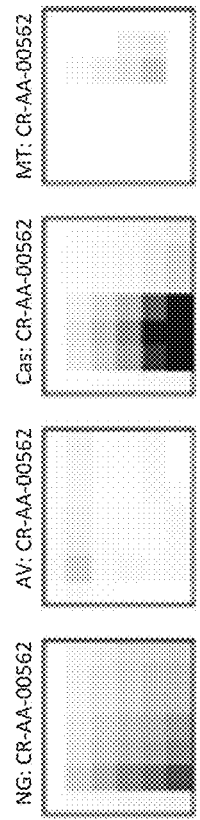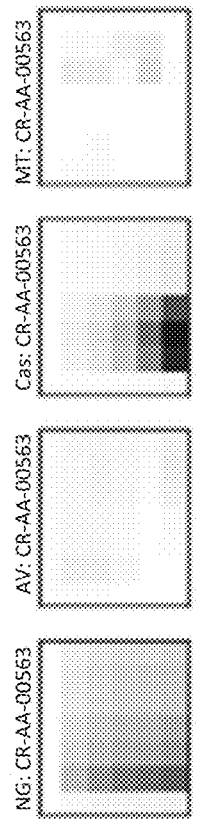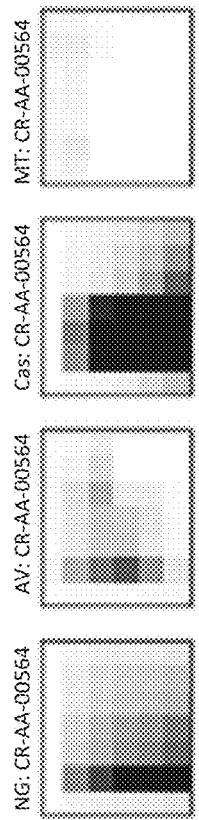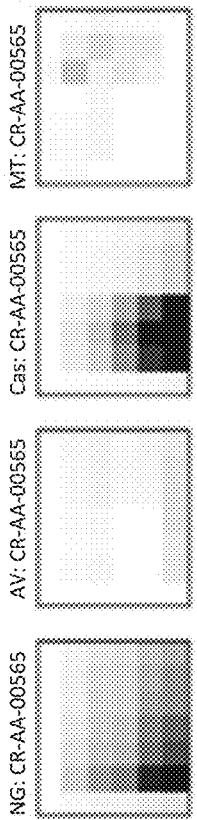
FIG. 14A (continued)

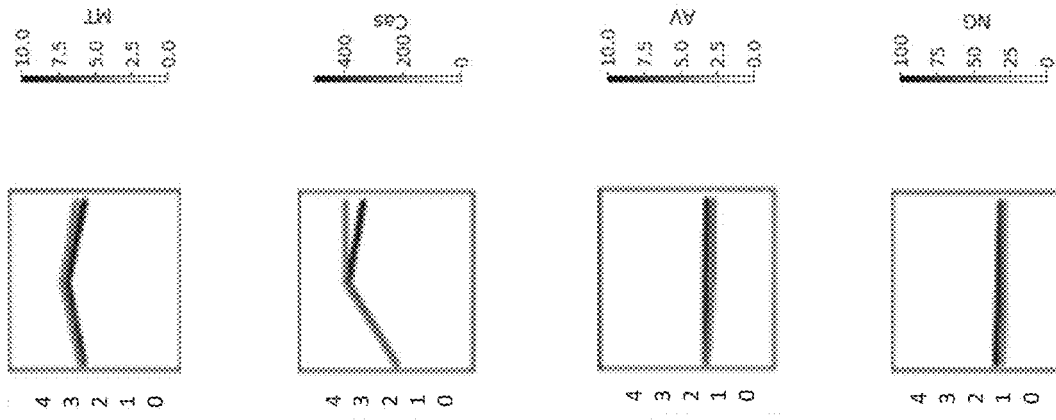
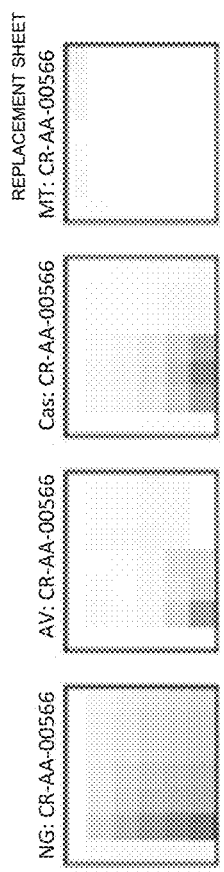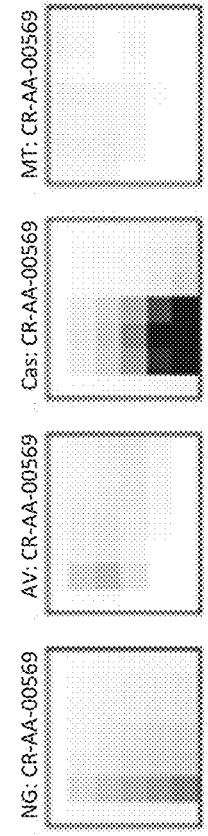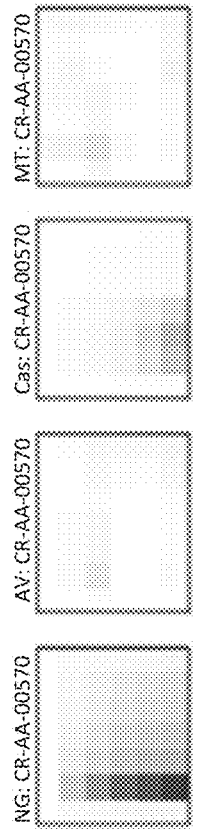
FIG. 14B

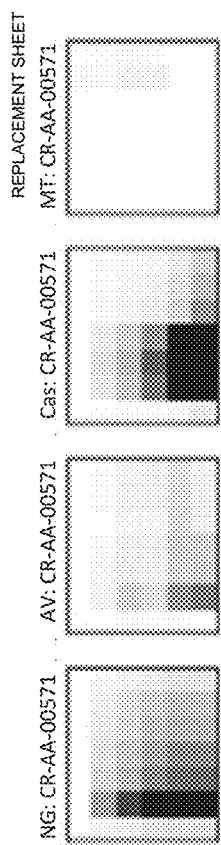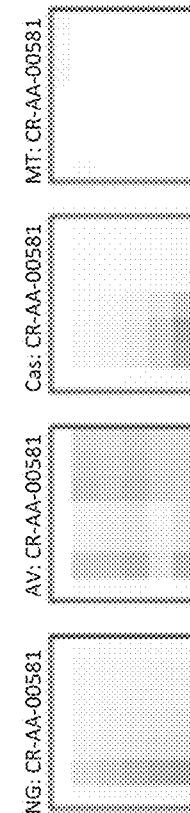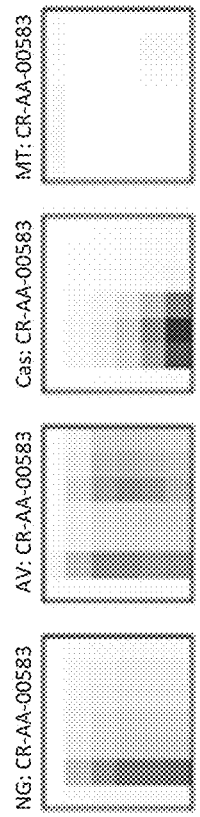
FIG. 14B (continued)

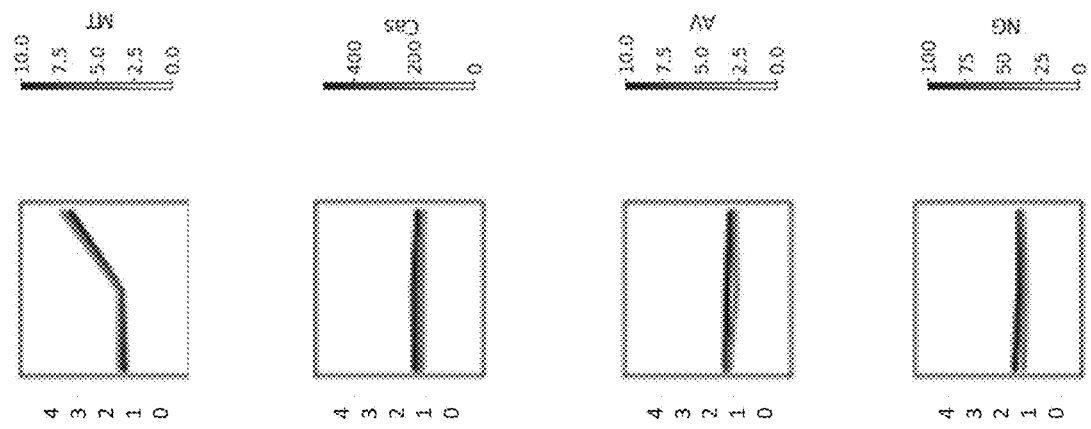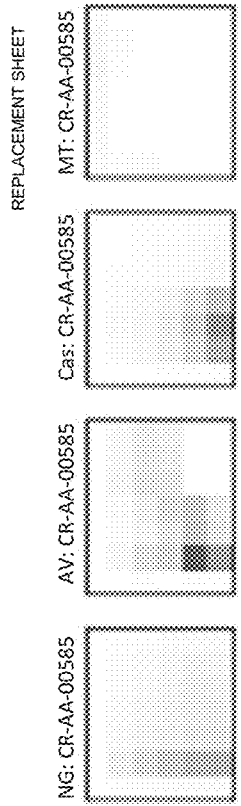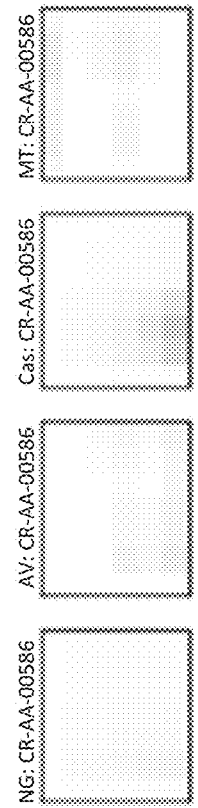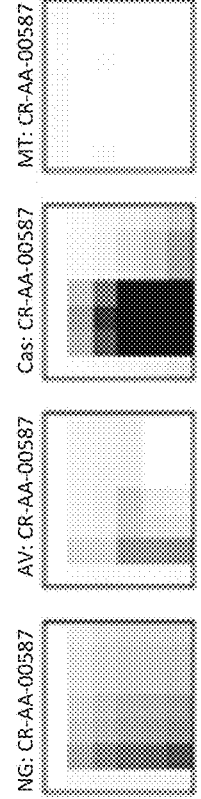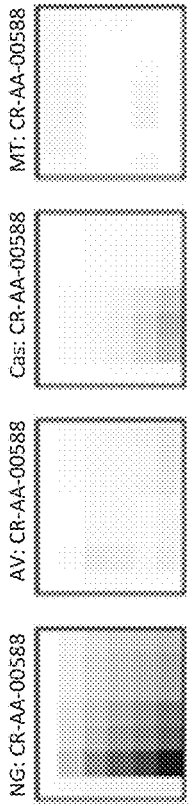
FIG. 14B (continued)

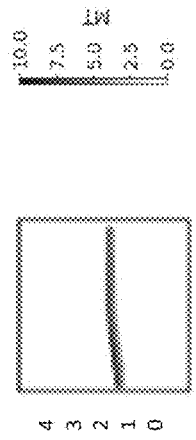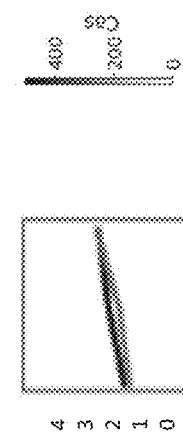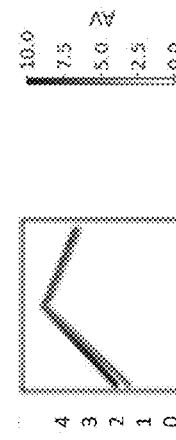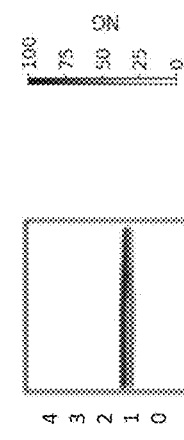
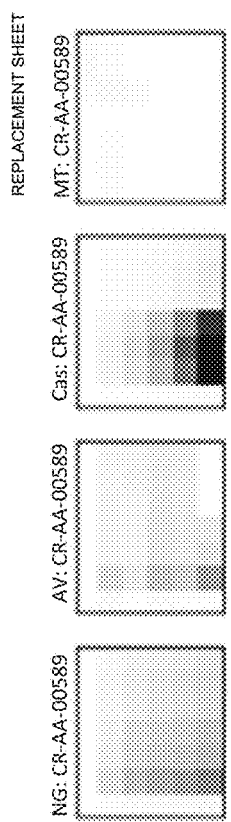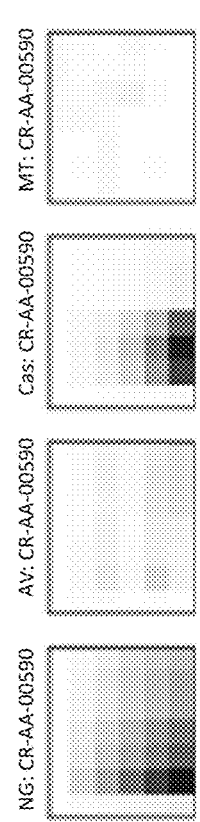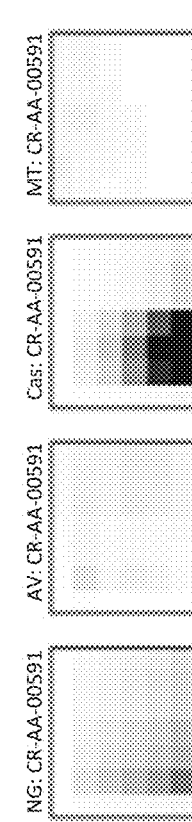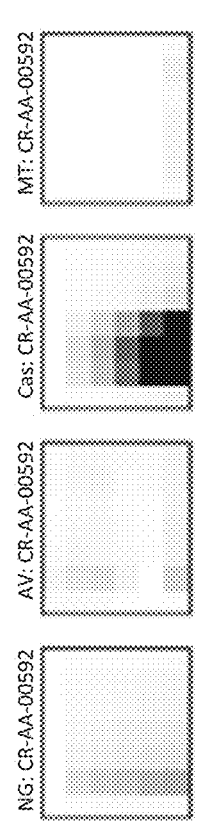
FIG. 14B (continued)

MACHINE-LEARNED PHARMACOLOGY OPTIMIZATION

CROSS REFERENCE TO RELATED APPLICATIONS

This application claims the benefit of U.S. Provisional Application No. 63/114,389, filed Nov. 16, 2020, which is incorporated by reference in its entirety.

BACKGROUND

In vivo animal studies required in determining the pharmacology of new compounds is very expensive. The problem is more acute when the goal is to build predictive models of pharmacology, since it requires screening hundreds, if not thousands, of compounds in rodents, in non-human primates and in Phase I/II trials in humans. The cost of such screening can be hugely reduced if in vitro pharmacology recapitulates in vivo behavior and a robust in vitro to in vivo mapping for toxicology and efficacy can be established. However, this is not possible without creating high-content data, which requires burdensome amounts of screening in vivo. Moreover, such a mapping may not be possible for some pharmacological endpoints, for example, tissue distribution and immunogenicity.

There is a need to establish algorithmic methods to reduce the burden of in vivo screening drastically, without compromising the quality of data and the granularity and certainty with which the pharmacology is learned.

SUMMARY

Aspects of the present disclosure include methods for optimizing pharmacological compound development and methods for optimizing one or more modifications of a compound. Aspects of the present disclosure further include methods for designing treatments for a disease, and methods for designing candidate compounds to treat a disease that causes one or more disease effects. Aspects of the present disclosure further include computer-implemented methods for training a model for pharmacological compound design, and computer-implemented methods for optimizing chemical modification of pharmacological compounds.

In one embodiment, a method for optimizing pharmacological compound development comprises: accessing, for each compound of a plurality of compounds, information describing an effect of the compound; determining, for each compound, a corresponding minimum amount of the compound required to produce an above-threshold effect and a maximum amount of the compound that can be administered to a subject; training an initial compound model based on the accessed information, the initial compound model identifying a first set of compound combinations, each compound combination including a subset of compounds, the number of compounds in each subset of compounds based on the minimum amount and maximum amount corresponding to each compound in step (b); for each compound combination in the first set of compound combinations: accessing a set of effects caused by an application of the subset of compounds included in the compound combination; and determining an association, for each effect of the subset of effects, between the effect and the compound of the subset of compounds that caused the effect; retraining the initial compound model based on the determined associations between effects and compounds; determining a target set of effects; and selecting one or more compounds of the plurality of compounds for administering to a target subject by applying the retrained compound model to the target set of effects.

In one embodiment, the effect is of each individual compound.

In one embodiment, the effect is between the compounds within the subset of compounds.

In one embodiment, the effect is selected from: a biophysical effect, a synergistic or antagonistic effect, and a combination thereof.

In one embodiment, the biophysical effect is a biological effect, a chemical effect, or a pharmacological effect.

In one embodiment, the pharmacological effect is a pharmacodynamic interaction between the compounds within the subset of compounds.

In one embodiment, the biophysical effect is a toxicity or an immune response of the subset of compounds.

In one embodiment, the biophysical effect is a toxicity or an immune response of each individual compound.

In one embodiment, the maximum amount of the compound is the maximum concentration of the compound that is safe to administer to the subject.

In one embodiment, the compound model comprises a matrix.

In one embodiment, the matrix is based on the accessed information, each column of the matrix corresponding to a compound that can be included in the subset of compounds, and each row of the matrix corresponding to an experiment associated with each subset of compounds.

In one embodiment, the experiment associated with a subset of compounds comprises a concentration of each compound within the subset of compounds.

In one embodiment, the subset of compounds comprises 2 or more compounds, 3 or more compounds, 4 or more compounds, or 5 or more compounds.

In one embodiment, the matrix comprises a plurality of experiments.

In one embodiment, the plurality of experiments comprises 2 or more experiments, 3 or more experiments, 4 or more experiments, 5 or more experiments, 10 or more experiments, 15 or more experiments, 20 or more experiments, 50 or more experiments, or 100 or more experiments.

In one embodiment, every compound in the subset of compounds is included in an identical number of experiments.

In one embodiment, every experiment in the matrix has a fixed number of compounds.

In one embodiment, the method comprises a constraint such that no two compounds are in more than 1 experiment.

In one embodiment, the subset of compounds is selected from a small molecule, a polypeptide, an oligonucleotide-based medicine (OBM), and a combination thereof.

In one embodiment, the polypeptide is an antibody or antibody-binding fragment.

In one embodiment, the method further comprises selecting compound combinations in the first set of compound combinations to reduce overlap between compounds in different compound combinations.

In one embodiment, for each of the one or more effects of a compound, a distribution of compounds in the plurality of compounds that cause an above-threshold measure of the effect is sparse.

In one embodiment, the accessed information comprises a qualitative prior configured to estimate a sparsity level and determine the matrix size.

In one embodiment, the accessed information comprises in vivo, in vitro, and/or in silico experiments based on pharmacological, medicinal chemistry, biophysics, and synthesis constraints of the plurality of compounds.

In one embodiment, the association comprises quantitative mapping between the effect and each compound of the subset of compounds.

In one embodiment, quantitative mapping comprises an interaction between each of the compounds of the plurality of compounds that produces a positive or negative biophysical effect on the safety or efficacy of the combined compounds.

In one embodiment, the present disclosure provides a method for optimizing pharmacological compound development comprising: accessing, for each compound of a plurality of compounds, effect information describing an effect of the compound; iteratively training a compound experiment model until a threshold criterion is satisfied by: generating, for each of a plurality of experiments, a corresponding set of compounds to combine together in the experiment using the effect information; performing, for each of the plurality of experiments, the experiment by applying the corresponding set of compounds in a subject; determining, for each of the plurality of experiments, a resulting set of effects of the applied set of compounds within the subject; determining, for each of the plurality of experiments, an association between each effect of the resulting set of effects and a compound of the applied set of compounds to which the effect is attributed; and updating the effect information based on the determined associations between effects and compounds; wherein the total number of experiments performed while training the compound experiment model is less than a total number of possible combinations of the plurality of compounds.

In one embodiment, the trained compound experiment model comprises a matrix.

In one embodiment, the effect is a synergistic or antagonistic effect between two or more compounds of the corresponding set of compounds.

In one embodiment, the effect is selected from: biological effect, a chemical effect, a pharmacological effect, and a combination thereof.

In one embodiment, the effect is selected from: a biological effect, a chemical effect, and a pharmacological effect, in combination with synergistic or antagonistic effects between compounds of the corresponding set of compounds.

In one embodiment, the pharmacological effect is a pharmacodynamic interaction between the compounds within the subset of compounds.

In one embodiment, the biophysical effect is a toxicity or an immune response of the subset of compounds.

In one embodiment, the biophysical effect is a toxicity or an immune response of each individual compound.

In one embodiment, the corresponding set of compounds comprises 2 or more compounds, 3 or more compounds, 4 or more compounds, 5 or more compounds, 6 or more compounds, 7 or more compounds, 8 or more compounds, 9 or more compounds, or 10 or more compounds.

In one embodiment, the corresponding set of compounds is selected from a small molecule, a polypeptide, an oligonucleotide-based medicine (OBM), and a combination thereof.

In one embodiment, the polypeptide is an antibody or antibody-binding fragment.

In one embodiment, the association comprises quantitative mapping between the effects is the interaction between each of the plurality of compounds that produce a positive or negative biophysical effect on the safety or efficacy of the combined compounds.

In one embodiment, the interaction is a chemical interaction, a molecular interaction, a toxic interaction, a synergistic or antagonistic interaction, or a combination thereof.

In one embodiment, the subject is an animal.

In one embodiment, the subject is a mammal or a rodent.

In one embodiment, steps a)-c) are repeated until a threshold criteria is satisfied by the iteratively updated trained compound experiment model based on one or more desired effects.

In one embodiment, a method for optimizing modifications of a compound comprises: accessing, information describing one or more effects of the compound associated with one or more modifications to the compound; determining a minimum number of modifications to the compound required to produce an above-threshold effect and a maximum number of modifications of each modification that can be administered to a subject; training an initial compound modification model based on the accessed information identifying a first set of compound modification combinations, each compound modification combination including a subset of compound modifications, the number of compound modifications in each subset based on the determined minimum amount and maximum number; for each compound modification combination in the first set of compound modification combinations: accessing a set of effects caused by an application of the subset of compound modifications included in the compound modification combination; and determining an association, for each effect of the subset of effects, between the effect and the compound modification of the subset of compound modifications that caused the effect; retraining the initial compound modification model based on the determined associations between effects and compound modifications; determining a target set of effects; and selecting one or more compound modifications of the plurality of compound modifications for administering to a target subject by applying the retrained compound modification model to the target set of effects.

In one embodiment, the application of the subset of compound modifications comprises in vitro experiments, in vivo experiments, in silico experiments, or a combination thereof.

In one embodiment, the one or more modifications comprises sequence-specific modifications.

In one embodiment, the sequence-specific modifications comprise an amino acid substitution and/or a nucleotide substitution.

In one embodiment, the one or more modifications comprises chemical modifications.

In one embodiment, the one or more modifications comprises two or more modifications, three or more modifications, four or more modifications, or five or more modifications.

In one embodiment, the effect is a synergistic or antagonistic effect between compound modification combinations.

In one embodiment, the effect is of each individual modification on the compound.

In one embodiment, the effect is between the modifications within the compounds.

In one embodiment, the effect is selected from: a biophysical effect, a synergistic or antagonistic effect, and a combination thereof.

In one embodiment, the biophysical effect is a biological effect, a chemical effect, or a pharmacological effect.

In one embodiment, the pharmacological effect is a pharmacodynamic interaction between compound modification combinations.

In one embodiment, the biophysical effect is a toxicity or an immune response between compound modification combinations.

In one embodiment, the biophysical effect is a toxicity or an immune response of each individual modification of the compound.

In one embodiment, the effect is affinity maturation of the compound.

In one embodiment, the effect is stability of the compound.

In one embodiment, the effect is a conjugation reaction of the compound to a moiety.

In one embodiment, the compound modification model comprises a matrix.

In one embodiment, the matrix is based on the accessed information, each column of the matrix corresponding to a compound modification that can be included in the first set of compound modification combinations, and each row of the matrix corresponding to an experiment associated with the first set of compound modification combinations.

In one embodiment, the subject is an animal.

In one embodiment, the subject is a mammal or a rodent.

In one embodiment, the corresponding set of compounds is selected from a small molecule, a polypeptide, an oligonucleotide-based medicine (OBM), and a combination thereof.

In one embodiment, the polypeptide is an antibody or antibody-binding fragment.

In one embodiment, the association comprises quantitative mapping between the effect and each compound of the subset of compounds.

In one embodiment, quantitative mapping comprises an interaction between each of the compound modifications of the plurality of compounds that produces a positive or negative biophysical effect on the safety or efficacy of the combined compound modifications.

In one embodiment, a method for designing treatments for a disease comprises: accessing, for each of a plurality of therapies, information describing an effect of the therapy on a subject; determining a number of therapies that can be combined such that the combination is safe to apply and such that an effect of each therapy in the combination can be detected when applied; generating a matrix based on the accessed information, each column of the matrix corresponding to a therapy of the plurality of therapies and each row of the matrix corresponding to an experiment associated with a set of the therapies; for each experiment, determining a set of effects caused by an application of the set of therapies associated with the experiment and determining which therapy in the set of therapies corresponds to each effect in the set of effects; modifying the matrix by additional rows corresponding to additional experiments, each associated with a different set of the therapies; and treating the disease with a set of therapies selected using the modified matrix.

In one embodiment, the effect is of each individual therapy.

In one embodiment, the effect is between the therapies within the set of therapies.

In one embodiment, the effect is selected from: a biophysical effect, a synergistic or antagonistic effect, and a combination thereof.

In one embodiment, the biophysical effect is a biological effect, a chemical effect, or a pharmacological effect.

In one embodiment, the pharmacological effect is a pharmacodynamic interaction between the set of therapies.

In one embodiment, the biophysical effect is a toxicity or an immune response of the set of therapies.

In one embodiment, the biophysical effect is a toxicity or an immune response of each individual therapy.

In one embodiment, the set of therapies comprises two or more therapies, three or more therapies, four or more therapies, or five or more therapies.

In one embodiment, the combination of therapies comprises two or more selected from: photodynamic therapy, gene therapy, oxygen supply, physical therapy, surgical procedures, radiation and chemotherapy, and hormone treatments.

In one embodiment, the combination of therapies comprises drug treatments in combination with one or more of: biologics, a medical procedure, and a medical intervention.

In one embodiment, the medical intervention is selected from: vaccination, blood transfusion, gene therapy, oxygen supply, physical therapy, surgical procedure, radiation and chemotherapy, hormone treatment, and a combination thereof.

In one embodiment, the effect is a side effect of each individual therapy.

In one embodiment, the effect is a side effect caused by the combination of the therapies within the subset of therapies.

In one embodiment, a method for designing candidate compounds to treat a disease that causes one or more disease effects comprises: selecting a set of candidate compounds each associated with one or more compound effects that correspond to the one or more disease effects; generating a model that includes a set of compound combinations, each compound combination selected to minimize overlap between the candidate compounds in the compound combination and candidate compounds in other compound combinations in the set of compound combinations; in response to an application of each compound combination to a subject, determining, for each candidate compound in the compound combination, a measure of how the candidate compound addresses each of the one or more disease effects; iteratively modifying the model based on the determined measures of how each candidate compound addresses the one or more disease effects to include additional sets of compound combinations, each additional compound combination selected to minimize overlap between the candidate compounds in the additional compound combination and the candidate compounds in other compound combinations and other additional compound combinations; and selecting a final set of candidate compounds to treat the disease using the iteratively modified model and based on the one or more disease effects.

In one embodiment, a computer-implemented method of training a model for pharmacological compound design comprises: accessing a first set of data comprising physiological or pharmacological characteristics of each of a set of compounds from one or more databases; generating a first training set of data based on the accessed first set of data describing, for each compound of the set of compounds, a toxicity and an efficacy of the compound; training a machine-learned model in a first stage using the first training set of data; accessing a second training set of data describing an updated toxicity and updated efficacy of each compound in a set of compounds; and training the machine-learned model in a second stage using the second training set of data.

In one embodiment, a computer-implemented method of training a model for pharmacological compound design comprises: generating a first training set of data comprising, for each of a first set of compounds, information describing a composition of the compound, a toxicity of the compound, and a biophysical effect of the compound; training a machine-learned model using the first training set of data, the machine-learned model configured to map a composition of a compound to a toxicity and biophysical effects of the compound; generating a second training set of data describing an updated toxicity and updated biophysical effects of each compound in a second set of compounds, the second set of compounds selected using the machine-learned model; and retraining the machine-learned model using the second training set of data.

In one embodiment, a computer-implemented method for optimizing chemical modification of pharmacological compounds comprises: collecting data associated with one or more modifications to one or more pharmacological compounds and describing a resulting toxicity or effect of the modifications; comparing a resulting toxicity or effect of the modification to a predefined threshold; generating a model using the collected data, the model including combinations of 1) the pharmacological compounds and 2) a set of pharmacological compounds modified by the one or more chemical modifications; and collecting additional data associated with a toxicity or effect of the combinations included in the model when the resulting toxicity or effect of the chemical modification exceeds the predefined threshold.

In one embodiment, a method for optimizing combinatorial design and testing, wherein individual design contributions are efficiently deconvolved from a combination of two or more design elements comprising the steps of: providing a reference prior that is approximately sparse; calibrating the readout to the reference to determine the range of min to max for each individual design element; generating a custom measurement matrix specification using the parameters determined in step (b) and loading the generated positive measurement matrix into a computing device; physically combining the design elements in the proportions determined in step (c); collecting measurements for each mixture experiment as determined in step (c); reconstructing individual measurements from the mixture experiment; and optimizing the measurement matrix based on the determined measurements of step (e) and repeating steps (d)-(f); wherein, where the total number of experiments are fewer than the total number of design elements combined, or fewer than the number of total parameters to be learned.

In one embodiment, a method for deconvoluting individual pharmacological properties of a therapeutic intervention from testing combinations comprising two or more independent therapeutic interventions, comprises the steps of: providing a reference prior that is approximately sparse; calibrating the readout to the reference to determine the range of min to max dosing and mixing number for each therapeutic intervention; generating a custom measurement matrix specification using the parameters determined in step (b) and loading the generated positive measurement matrix into a computing device; physically combining the therapeutic intervention in the proportions determined in step (c); determining measurements of each combination experiment as determined in step (c); reconstructing individual measurements from the combination experiment; and updating and extending the measurement matrix based on the determined measurements of step (e) and repeating steps (d)-(f) until individual measurements are reconstructed for each therapeutic intervention in the mixture; wherein, where the total number of experiments are fewer than the total number of drugs combined, or fewer than the number of total parameters to be learned.

In one embodiment, a method for deconvoluting synergistic or antagonistic pharmacological properties of therapeutic intervention from testing one or more combinations comprising two or more independent therapeutic interventions, comprises the steps of: providing a reference prior that is approximately sparse; calibrating the readout to the reference to determine the range of min to max dosing and mixing number for each therapeutic intervention; generating a custom positive measurement matrix specification using the parameters determined in step (b) and customized to optimally detecting synergistic or antagonistic effects, and loading the generated positive measurement matrix into a computing device; physically combining the therapeutic intervention in the proportions determined in step (c); determining measurements of each combination experiment as determined in step (c); reconstructing individual measurements from the combination experiment; and updating and extending the measurement matrix based on the determined measurements of step (e) and repeating steps (d)-(f) until individual measurements are reconstructed for each therapeutic intervention in the mixture; wherein, where the total number of experiments are fewer than the total number of individual and synergistic or antagonistic parameters to be learned.

In one embodiment, a method for optimizing chemical modification of oligonucleotide-based medicines (OBMs), wherein two or more independent chemical modifications are simultaneously tested in the same physical system and the independent contributions for each independent chemical modification are deconvolved, said method comprises the steps of: providing a reference prior that is approximately sparse; calibrating the readout to the reference to determine the range of min to max dosing and mixing number for each OBM and chemical modification; generating a custom measurement matrix specification using the parameters determined in step (b) and loading the generated positive measurement matrix into a computing device; physically combining the OBMs in the proportions determined in step (c); determining measurements of each mixture experiment as determined in step (c); reconstructing individual measurements from the mixture experiment; and applying one or more transformations to the measurement matrix, including optimization and deterministic extension of said matrix, based on the determined measurements of step (e) and repeating steps (d)-(f) until individual measurements are reconstructed for each OBM in the mixture; wherein, where the total number of experiments are fewer than the total number of OBMs combined, or fewer than the number of total parameters to be learned.

In one embodiment, a computer-implemented method of training a model for optimization of chemical modification of oligo-based medicines (OBMs) comprises: collecting a set of physiological or pharmacology observations recorded in a experiment or medical record in a database; applying one or more transformations to each digital OBM toxicity record including normalization and pre-processing to create a modified set of digital OBM toxicity records; creating a first training set comprising the collected set of digital OBM toxicity records, the modified set of digital OBM toxicity records, and a third set of digital OBM toxicity records; training the model in a first stage using the first training set; creating a second training set for a second stage of training comprising the first training set and digital non-toxic OBMs that are incorrectly detected as toxic after the first stage of training; and training the model in a second stage using the second training set.

In one embodiment, a computer-implemented method of training a model for optimization of chemical modification of oligo-based medicines (OBMs) comprises: collecting a set of physiological or pharmacology records from a database; applying one or more transformations to each record including normalization and pre-processing to create a modified set of physiological or pharmacology records; creating a first training set comprising the collected set of physiological or pharmacology records, the modified set of physiological or pharmacology records, and a third set of non-physiological or non-pharmacology records; training the model in a first stage using the first training set; creating a second training set for a second stage of training comprising the first training set and non-physiological or non-pharmacology that are incorrectly detected as having one or more of a physiological or pharmacological effect after the first stage of training; and training the model in a second stage using the second training set.

In one embodiment, a computer-implemented method for optimizing chemical modification of oligonucleotide-based medicines (OBMs) comprises: collecting, by a computing device, OBM data related to one or more chemical modifications, the data comprising at least one of toxicity, nucleotide position of chemical moiety, and OBM sequence; comparing, by a computing device, at least one of the collected data to a predefined threshold; and generating a custom measurement matrix specification using the parameters determined in steps (a) and (b) and loading the generated positive measurement matrix into a computing device; and collecting additional OBM data relating to efficacy or toxicity when the collected data is greater than the predefined threshold, the additional data comprising combinatorial mixing data as specified by the measurement matrix specification.

BRIEF DESCRIPTION OF THE DRAWINGS

FIG. 6 is an exemplary depiction of the constraints in the graph algorithm of the present disclosure for measurement matrix construction.

FIG. 10 is an exemplary depiction of applications of combinatorial design. FIG. 10A is an exemplary depiction of chemistry modifications to explore, perhaps in independent sequence-contexts learned from information profiles of sequence contribution to pharmacology, where these modifications are composable, but realistically only a few K can be simultaneously incorporated in any one OBM. In some embodiments, a goal is to learn ideal modification strategies to improve pharmacology. In some embodiments a goal is to learn independent and synergistic and antagonistic contributions to pharmacology. FIG. 10B is an exemplary depiction of optimizing "gapmer"-design where all gaps are composed of units, say, dimers, and any OBM can only have at most a few such units. In an OBM on length 20 there are N=10 such position-dependent gap dimers to combine. This method allows for learning the synergies or antagonisms and individual contributions of gap to activity. FIG. 10C is an exemplary depiction of a general set up of combinatorial drug design, where a library of N drugs are explored, and only K drugs can be combined at a time owing to dosage limitations or other pharmacological constraints. This method allows for optimal learning of both individual impact and synergistic and antagonistic contributions of all K drugs leading to the identification of ideal combinations, and the optimal number of combinations M that are needed to be tested.

FIG. 11 is an exemplary depiction of encoding of combinatorial design to create the x matrix (unravelled to vector), for sparse learning using measurement matrix $\Phi$.

FIGS. 14A & 14B plots the typical time series of liver toxicity (column 5, ALT is black, AST is gray, x axis are the three time points, see study design), with increasing toxicity typically observed after the second dose for toxic ASOs, owing to accumulating toxic effects. The rest of the columns are measured dose-time matrix of response for various assays of cytotoxicity (all assays run on HeLa cell-line): first column is for cellular necrosis (measured using Necrosis Green); second column is for cell-membrane integrity (Annexin-V); third column is for apoptosis (Caspase 3/7); and the fourth column is or cell viability (RealTime-Glo MT Viability Assay). Each entry is for each ASO treatment. The response matrix rows are doses [0, 2, 5, 5, 10, 20, 40] uM concentration treatment, and the matrix columns are times of measurement [7 hrs, 24 hrs, 27 hrs, 30 hrs, 48 hrs, 51 hrs, 54 hrs]. The in vitro data can be used as a prior to set expectations on in vivo response; however, in vitro and in vivo endpoints do not always agree and in vitro measures cannot obviate in vivo measures, necessitating the current invention of reducing burden for in vivo pharmacology.

DETAILED DESCRIPTION

Figure 1A:
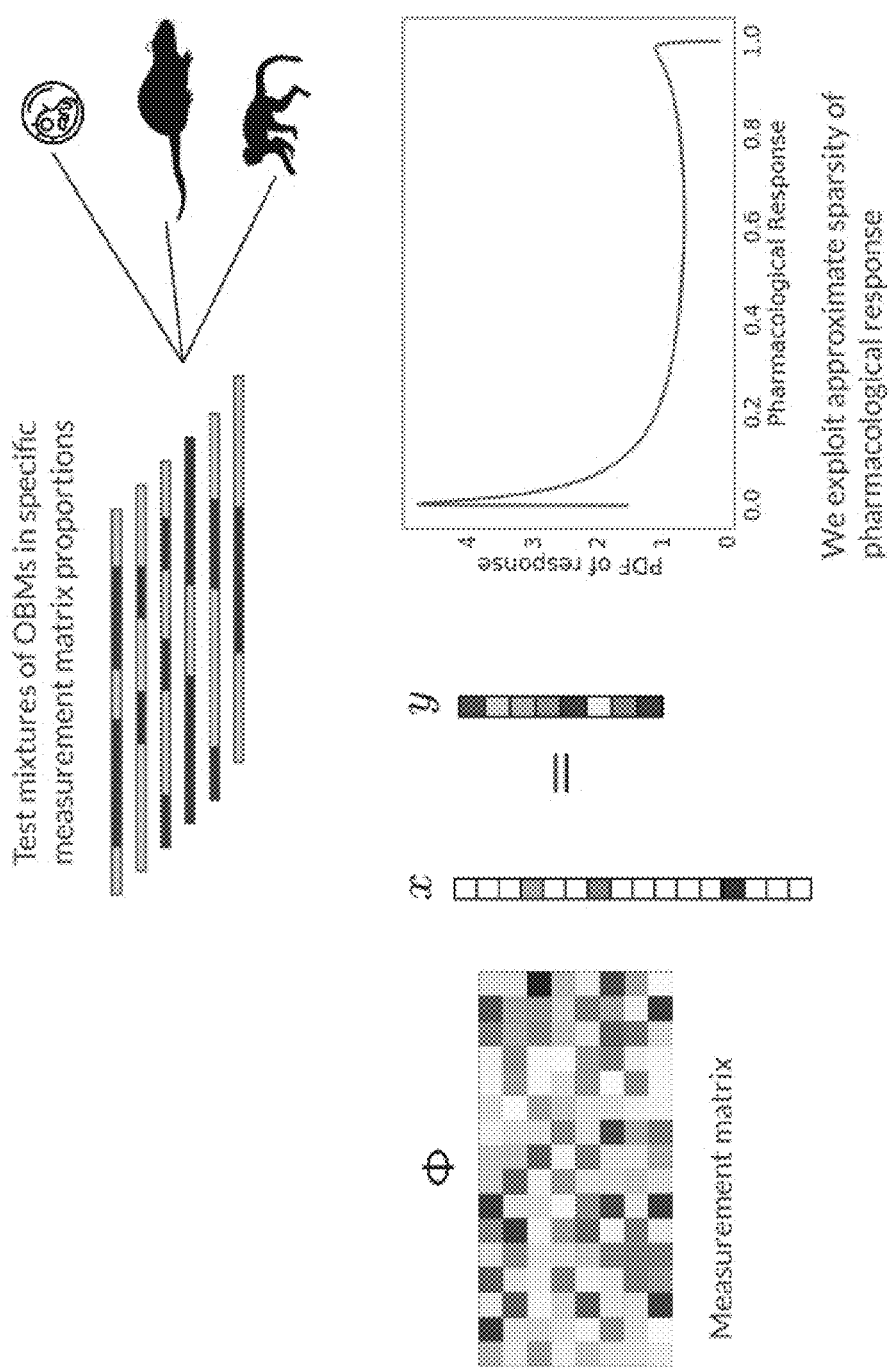
FIG. 1A depicts an exemplary framework that was explored in this approach: A number of, for example, oligonucleotide-based medicines (OBMs) were tested in vitro and in vivo, and read out the pharmacology of the mixture for the same pharmacological endpoint. The measurement matrix dictates the proportions of OBMs as a fraction of total dose, in each mixture to be tested and is created specifically for the endpoint in question, and the category of OBMs studied. The method is a compressed sensing algorithm, however, there are constraints on the measurement matrix that are unique to the problem at hand and not described in the traditional compressed sensing literature. For example, the measurement matrix rows are proportions, so should sum to unity, and each fraction value should be in the linear regime of dose response, i.e., none of the OBMs should be under-dosed or overdosed. Also, the examples explain the regime and transformations for which the signal to recover, i.e., the pharmacology measurement value of individual OBMs, is sparse. Sparsity in the present problem is rather unconventional-biological readouts are noisy, so naive sparsity, meaning a subset of (transformed) measurements being exactly zero, does not hold. Instead, the signal is only approximately sparse, necessitating the measurement matrix and recovery algorithms of the present disclosure.

Aspects of the present disclosure include methods for optimizing pharmacological compound development and methods for optimizing one or more modifications of a compound. Aspects of the present disclosure further include methods for designing treatments for a disease, and methods for designing candidate compounds to treat a disease that causes one or more disease effects. Aspects of the present disclosure further include computer-implemented methods for training a model for pharmacological compound design, and computer-implemented methods for optimizing chemical modification of pharmacological compounds.

Aspects of the present disclosure include systems for carrying out the methods of the present disclosure. Aspects of the present disclosure include a computer readable medium, comprising instructions, that cause a processor to carry out the methods of the present disclosure.

Reference will now be made in detail to several embodiments, examples of which are illustrated in the accompanying figures. It is noted that wherever practicable similar or like reference numbers may be used in the figures and may indicate similar or like functionality.

I. DEFINITIONS

Unless defined otherwise, all technical and scientific terms used herein have the meaning commonly understood by a person skilled in the art to which this description belongs. As used herein, the following terms have the meanings ascribed to them below.

The terms "biophysical", "biophysical effect", and "biophysical function" generally refer to biological, chemical, and physical properties of an oligonucleotide that determine its tolerability, functionality, activity, efficacy and effects within a living organism, cell or cell extract.

As used herein, the term "compound experiment model" refers to a set of (iterative) experiments whose design (i.e., measurement matrix) is updated by the results of the previous (or all previous) iterations, including calibration steps.

As used herein, the term "individual" refers to a human or animal individual. As used herein, the term "healthy individual" refers to an individual presumed to not have a disease or disorder.

As used herein, the term "oligonucleotide-based medicine" or "OBM" or "oligonucleotide-based drug" refers to an oligonucleotide-based therapeutic for treatment of diseases, such as genetic diseases. Oligonucleotide-Based Medicines/Drugs are polymeric molecules comprising natural and synthetic derivatives of nucleic acids.

As used herein, the term "pharmacology" refers to studying how of an oligonucleotide-based medicine (OBM) affects a biological system, for example, by studying its tolerability, functionality, activity, efficacy, pharmacokinetics, pharmacodynamics, absorption, distribution, metabolism, and extraction (ADME), and its tolerability in in vitro and in vitro.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, synthetic or derivatized nucleotide bases. "Oligonucleotide" generally refers to polynucleotides of between about 5 and about 100 nucleotides of single- or double-stranded DNA or RNA. For the purposes of this disclosure, there is no upper limit to the length of an oligonucleotide. Oligonucleotides are also known as oligomers or oligos. In some embodiments, oligonucleotides of the present disclosure comprise base modifications, chemical modifications, or combinations thereof. In some embodiments, oligonucleotides of the present disclosure comprise computer representation of the molecules in formats including but not limited to hierarchical editing language for macromolecules (HELM) or simplified molecular-input-line entry system (SMILES) strings.

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, carboxy alkyl, amino, hydroxyl, halogen (i.e., fluoro, chloro, bromo, or iodo), thiol or alkylthiol moiety. Preferred alkyl (e.g., alkyl, carboxy alkyl, etc.) moieties comprise of about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenosine, a N,N-dimethylaniline, an azaadenines, a 8-bromoadenine, a 8-hydroxyadenine, a 6-hydroxy aminopurine, a 6-thiopurine, a 4-(6-aminohexyl/cytosine), and the like. Other examples are well known to those of skill in the art.

A nucleobase may be composed in a nucleoside or nucleotide, using any chemical or natural synthesis method described herein or known to a person of ordinary skill in the art. Such nucleobase may be labeled or it may be part of a molecule that is labeled and contains the nucleobase.

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar.

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

As used herein, "message passing" refers to a family of algorithms which are general mathematical tools to efficiently compute marginal probability distributions on graphical models. These algorithms are exact for tree-like graphs and are often called loopy belief propagation (loopy-BP) for graphs with loops, for which these are approximate methods. These work remarkably well on such graphs however, provided the number of loops are few (the graph is sparsely connected).

It is understood in the art that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A subject polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining non-complementary nucleotides may be clustered or interspersed with complementary nucleotides and need not be contiguous to each other or to complementary nucleotides. As such, an antisense polynucleotide which is 18 nucleotides in length having 4 (four) noncomplementary nucleotides which are flanked by two regions of complete complementarity with the target nucleic acid would have 77.8% overall complementarity with the target nucleic acid. Percent complementarity of an oligomeric compound with a region of a target nucleic acid can be determined routinely using BLAST programs (basic local alignment search tools) and Power-BLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a biophysical effect" includes a plurality of such biophysical effects and reference to "the compound" includes reference to one or more compounds and equivalents thereof known to those skilled in the art, and so forth. It is further noted that the claims may be drafted to exclude any optional element. As such, this statement is intended to serve as an antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

II. OVERVIEW OF METHOD

Aspects of the present disclosure provide methods for optimizing pharmacological compound development for reducing the number of experiments needed to be performed to determine the safety and efficacy of various compounds. Aspects of the present disclosure provide methods for optimizing modifications of a compound for reducing the number of experiments needed to be performed to optimize the compound for treating a disease.

In one aspect, the methods of the present disclosure include optimizing pharmacological compound development. In some embodiments, optimizing pharmacological compound development includes accessing, for each compound of a plurality of compounds, information describing an effect of the compound. In certain embodiments, the method includes determining, for each compound, a corresponding minimum amount of the compound required to produce an above-threshold effect and a maximum amount of the compound that can be administered to a subject. In certain embodiments, the method includes training an initial compound model based on the accessed information, the initial compound model identifying a first set of compound combinations, each compound combination including a subset of compounds, the number of compounds in each subset of compounds based on the minimum amount and maximum amount corresponding to each compound in step (b). In certain embodiments, for each compound combination in the first set of compound combinations: the method includes accessing a set of effects caused by an application of the subset of compounds included in the compound combination; and determining an association, for each effect of the subset of effects, between the effect and the compound of the subset of compounds that caused the effect. In certain embodiments, the method includes retraining the initial compound model based on the determined association between effects and compounds. In some embodiments, the method includes determining a target set of effects. In certain embodiments, the method includes selecting one or more compounds of the plurality of compounds for administering to a target subject by applying the retrained compound model to the target set of effects.

In some embodiments, the association comprises quantitative mapping between effects and compounds. The term "association", as used in the present disclosure, can refer to a quantitative mapping or other quantitative relationship between compound and effect. In some embodiments, a quantitative mapping between the effects and the compounds is the interaction between each of the plurality of compounds that produce a positive or negative biophysical effect on the safety or efficacy of combined compounds.

In some embodiments, methods of the present disclosure include methods for optimizing pharmacological compound development, comprising: accessing, for each compound of a plurality of compounds, effect information describing an effect of the compound. In certain embodiments, the method includes iteratively training a composite experiment model until a threshold criterion is satisfied by: generating, for each of a plurality of experiments, a corresponding set of compounds to combine together in the experiment using the effect information; performing, for each of the plurality of experiments, the experiment by applying the corresponding set of compounds in a subject; determining, for each of the plurality of experiments, a resulting set of effects of the applied set of compounds within the subject; determining, for each of the plurality of experiments, an association between each effect of the resulting set of effects and a compound of the applied set of compounds to which the effect is attributed; and updating the effect information based on the determined associations between effects and compounds. In certain embodiments, the total number of experiments performed while training the compound experiment model is less than a total number of possible combinations of the plurality of compounds. In certain embodiments, the method includes retraining the trained composite experiment model until the threshold criterion is satisfied. In some embodiments, a composite experimental model is a set of iterative experiments whose measurement matrix is updated by the results of one or more previous iterations, including the calibration step. One non-limiting example of threshold criteria is when the accuracy of the recovered signal is within the signal to noise ratio of the measurement noise (instrumental, biological, physiological, physical, biophysical, chemical, biochemical etc. in origin) of the measurement quantifying an effect of a compound.

In some embodiments, the threshold criterion is a confidence threshold. In some embodiments, the confidence threshold can include a criteria that can be satisfied, such as a performance limitation of the model. For example, when the accuracy of the recovered signal is within the signal to noise ratio of the measurement noise (instrumental, biological, physiological, physical, biophysical, chemical, biochemical etc. in origin) of the measurement quantifying an effect of a compound. Such threshold criteria include but are not limited to accuracy of learning, within measurement noise, of individual and synergistic/antagonistic parameters. In certain embodiments, the confidence threshold can include a criteria that can be satisfied, such as, but not limited to, a number of iterations. In certain embodiments, the number of iterations includes at least 1 iteration, at least 2 iterations, at least 3 iterations, at least 4 iterations, at least 5 iterations, at least 6 iterations, at least 7 iterations, at least 8 iterations, at least 9 iterations, or at least 10 iterations.

II.A. Example Sensing System

Figure 2A:
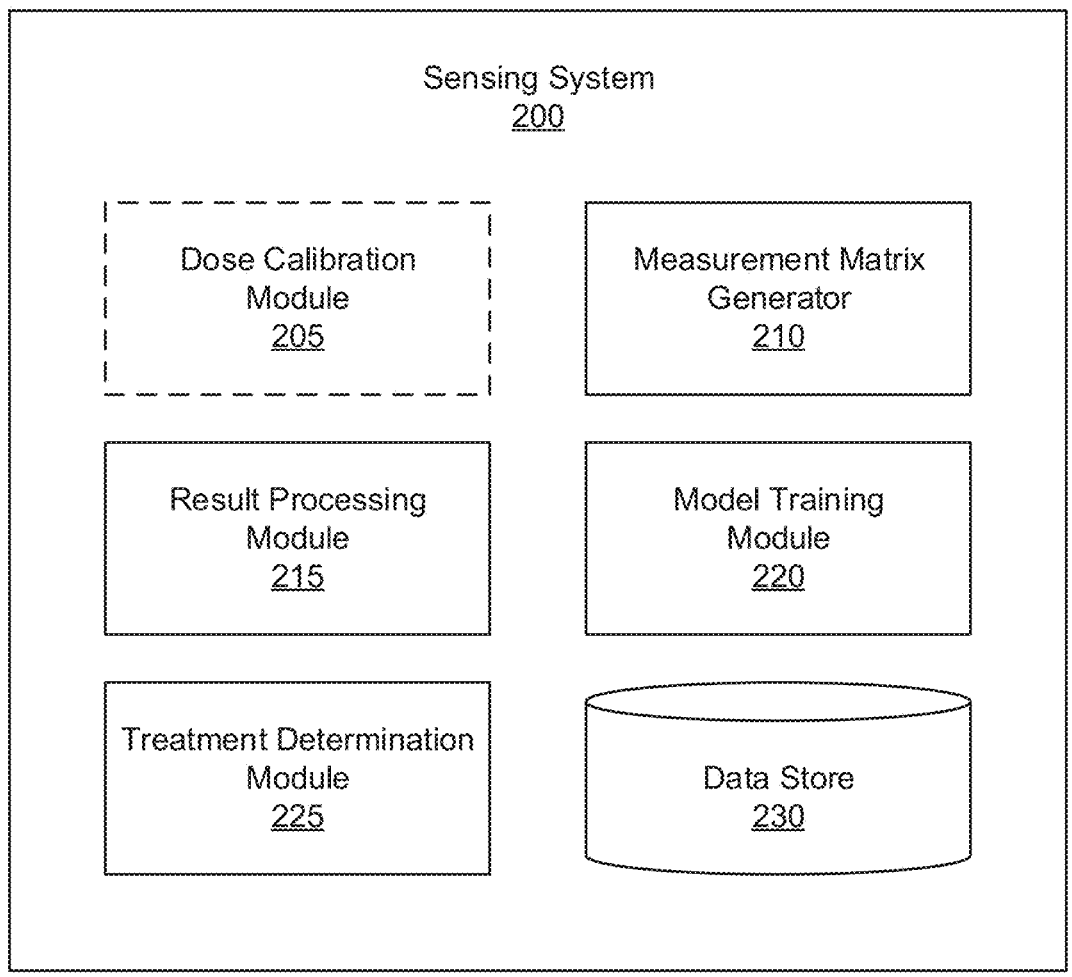
FIG. 2A illustrates an example sensing system, according to one or more embodiments.

FIG. 2A illustrates an example sensing system 200, according to one or more embodiments. The sensing system 200 may be implemented on a general computing system. The sensing system 200 may perform any of the methods described herein this disclosure, e.g., relating to optimizing treatment based on compressed sensing of limited clinical data. The sensing system 200 includes at least a measurement matrix generator 210, a result processing module 215, a model training module 220, a treatment optimization module 225, and a data store 230. The sensing system 200 may include other modules such as a dose calibration module 205. The sensing system 200 operates in conjunction with one or more scientists that perform the clinical trials. The clinical data is provided to the sensing system 200 which generates predictive models based on the clinical data. The sensing system 200 may optimize treatment based on the predictive models.

Figure 1B:
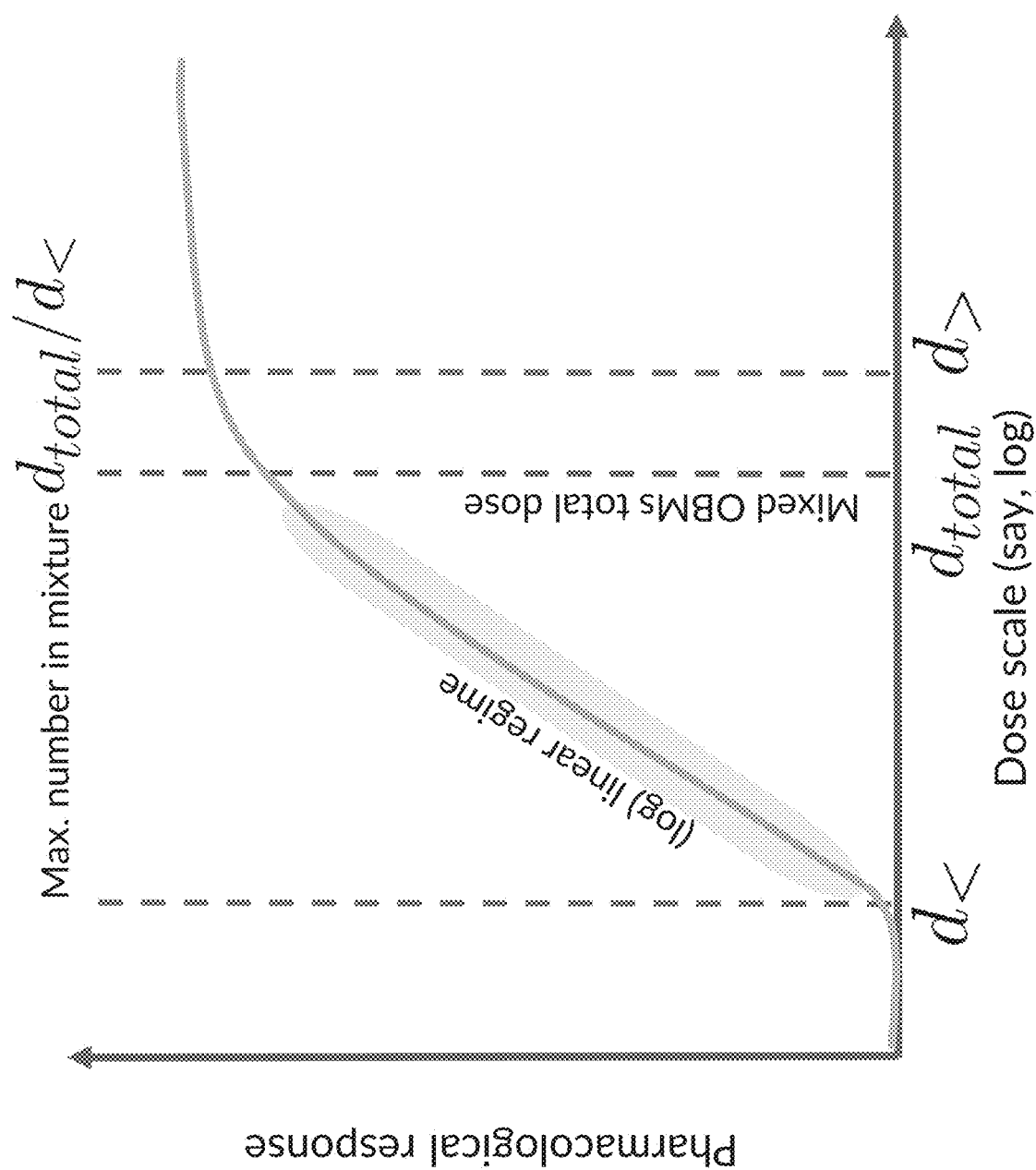
FIG. 1B is an exemplary depiction of the maximum number of OBMs that can be mixed in any experiment to reduce the number of, by way of a non-limiting example, animals needed to study pharmacology, and is determined by the (transformed) linear regime of the dose vs. response curve characterized by calibration experiments. The range of (transformed) dose regime of linear response is denoted as $[d_<, d_>]$. Beyond $d_>$ either response is non-linear or the system is highly overdosed. In one non-limiting example the optimal total dose is $d_{total}/d_<$. Below $d_<$ the OBMs either under-dosed or the sensitivity of the response measurement is very low. Therefore, the maximum number of OBMs that can be mixed in an experiment is $d_{total}/d_<$, where $d_{total} \leq d_>$. In the linear regime with such choices, the expected response of the mixture is simply the additive response of individual OBMs we wish to infer, and none of the OBMs in the mixture are under-dosed and overall the mixed dosing is not overdosed. A safe amount of the treatment (e.g., OBMs, or therapies, etc.) that may be administered to an individual may be determined through clinical settings, e.g., determining levels that cause detrimental responses (e.g., toxicity, other symptoms, etc.). In one or more embodiments, the safe amount is determined based on the dose response curve, for example, the safe amount threshold is $d_>$. The sparsity space of interest is in deviation from such a well-calibrated expected response—we need to have calibration to a reasonable degree of confidence before embarking on a compressed sensing readout.

In some embodiments, the dose calibration module 205 calibrates a dose response curve (one example of which is shown in FIG. 1B). In some embodiments, the dose response curve is provided by a compound manufacturer. The dose response curve graphs pharmacological response against dose scale. The dose response curve may be unique to humans and to each animal tested in clinical trial settings. In some embodiments, the dose calibration module 205 may generate and/or update the dose response curve based on clinical trial data. For example, the dose calibration module 205 may receive clinical data wherein pharmacological response is recorded after one or more test animals are dosed at varying dose levels. In generating a dose response curve, the dose calibration module 205 may regress the clinical data to determine the dose response curve. In updating a dose response curve, the dose calibration module 205 may adjust the dose response curve based on the clinical data, e.g., by shifting a point along the curve, etc.

The measurement matrix generator 210 generates a measurement matrix comprising candidate compound mixtures for clinical trials. Based on the dose response curve, the measurement matrix generator 210 determines a maximum number of compounds that may be combined in one mixture to be dosed in an organism. For example, as shown in FIG. 1B, the dose response curve has a $d_{total}$ point which indicates a total dose of a mixture. The maximum number of compounds may be determined by dividing the total dose by the minimum dose needed to achieve a pharmacological effect (e.g., rounded down to the nearest whole number), denoted as $d_<$ in FIG. 1B. The measurement matrix generator 210 may consider other factors in generating the measurement matrix, including ensuring each compound is selected for approximately the same number of compound mixtures as other compounds, ensuring two or more compounds are not selected for two or more mixtures, optimizing for a maximum number of mixtures that may be tested. Two compounds can have different doses in the mixture, whereby the sensing matrix entries for each row will become real positive numbers corresponding to the proportions of compounds in the mixture corresponding to that row of the matrix, or become weights for each compound determined by a calibration step. The compressed sensing method can identify synergistic or antagonistic effects of two compounds even though they have not been tested together, as long as their individual pharmacology is known in clinical settings.

The result processing module 215 processes clinical data. The result processing module 215 may perform statistical analyses to process the clinical data. Analyses may include normalizing the clinical data based on characteristics of the trial participants (e.g., body weight), identifying outliers (e.g., through statistical analysis), performing a mathematical transformation of the data (e.g., changing to a different unit of measurement, or scaling the data). Clinical data generally includes data received from clinical trials on living organisms. The clinical data may, in some embodiments, be represented as a quantitative observation of a pharmacological response in the living organism followed by the dosing of a compound mixture. For example, the pharmacological response may be liver toxicity, blood sugar level, etc. In some other embodiments, the clinical data may include qualitative observations.

The model training module 220 trains one or more predictive models based on the clinical data. A trained predictive model may be configured to input a compound mixture including some combination of compounds and to output a predicted pharmacological response. In training the predictive models, the model training module 220 generates a feature vector for each data sample. The data sample describes a compound mixture dosed in the organism and a pharmacological response observed in response to the dosing. The model training module 220 generates the feature vector based on the compound mixture dosed in the organism. In one example, the feature vector may be sized according to the number of compounds that may be mixed. The feature vector may retain information relating to the dose amount for each compound. In other embodiments, the feature vector may be binarized as to whether a compound at a set dose is included.

Generally, many different algorithms can be used to train the predictive models. With the clinical data collected for the tested compound mixtures, the model training module 220 may perform supervised training of the predictive models. Supervised training entails inputting training samples with known label or value and training the model to predict the label or value based on a feature vector representing the training sample. For instance, the model can include a neural network algorithm, a support vector machine algorithm, a Naive Bayes algorithm, a nearest neighbor algorithm, a boosted trees algorithm, a random forest algorithm, a decision tree algorithm, a regression algorithm, a multinomial logistic regression algorithm, a linear model, or a linear regression algorithm. The regression algorithm can be logistic regression with lasso, L2 or elastic net regularization.

In one or more embodiments, the model training module 220 may identify additional compound mixtures for clinical trials to refine the predictive models. The model training module 220 may seek to identify relations between compounds that are unknown or uncertain. For example, compound A and compound B have never been clinically tested such that their relational effect on pharmacological response is relatively unknown or uncertain. The model training module 220 may increase robustness of the predictive models by selecting compound A and compound B to be clinically tested. The relations between compounds to be tested may be provided to the measurement matrix generator 210 to determine a measurement matrix for testing additional compound mixtures.

The treatment determination module 225 determines a treatment based on the predictive models. The treatment determination module 225 may consider a variety of constraints in developing a treatment. Example constraints may include: minimizing a total number of compounds included in the treatment, optimizing pharmacological response, manufacturing costs of each compound, side effects of each compound, known synergistic or antagonistic interactions between a subset of compounds, dose response of each compound, pharmacokinetics and pharmacodynamics of each compound, ADME of each compound, other known characteristics of the compounds, constraints on other characteristics of the treatment, etc. The treatment determination module 225 may determine a plurality of candidate compound mixtures to test based on one or more of the constraints. With each candidate compound mixture, the treatment determination module 225 may determine a feature vector of the candidate compound mixture for use with the predictive models. The treatment determination module 225 inputs the feature vector into one or more of the predictive models to generate a predicted pharmacological response for the candidate compound mixture. The treatment determination module 225 may rank the candidate compound mixtures based on the predicted pharmacological responses and select one of the candidate compound mixtures for use as the treatment based on the ranking. The determined treatment may be provided to a manufacturer for formulation of the treatment comprising the selected compound mixture.

The data store 230 stores data used by the sensing system 200. The data is stored on storage medium and accessible by the various components of the sensing system 200. The data may include dose response curves associated with each compound considered. The dose response curves may be obtained by another system or determined by the dose calibration module 205. The data may include prior measurement matrices utilized for clinical trials along with the clinical data collected for the measurement matrix. The data also includes the predictive models trained by the model training module 220. The predictive models, according to one or more embodiments, may generally be described with one or more functions with one or more weights associated between variables of the functions. The weights may be trained by the model training module 220. The data may also include treatments determined by the treatment determination module 225.

Figure 2B:
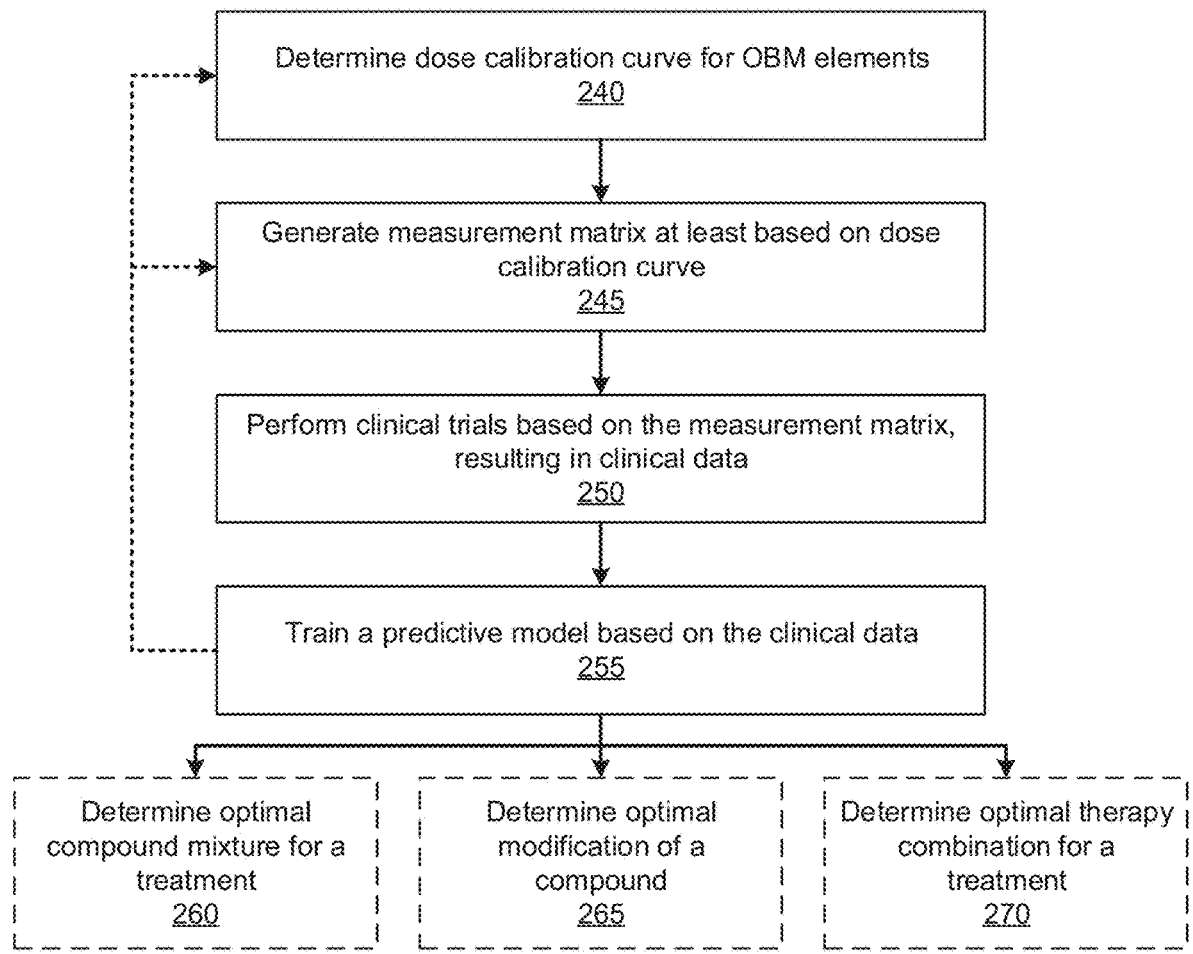
FIG. 2B illustrates a method of determining a treatment using compressed sensing of compound mixtures (i.e., deconvoluting of individual compound properties from compound mixtures), according to one or more embodiments.

FIG. 2B illustrates a method of determining a treatment using compressed sensing of compound mixtures, according to one or more embodiments. The sensing system 200 may perform some or all of the steps of the method illustrated in FIG. 2B. In one or more embodiments, the various components of the sensing system 200 perform each of the steps of the method. Generally speaking, the method involves determining a measurement matrix for clinical trials of various compound mixtures. According to the clinical data, the sensing system 200 generates one or more predictive models to predict pharmacological response of untested compound mixtures. With the predictive models, the sensing system 200 determines a treatment with a compound mixture according to one or more constraints. Advantages of this method include reduced clinical trials by training and utilizing a predictive model. The predictive model can be used directly to determine treatments and/or determine candidate compound mixtures to test in clinical settings. Although the method is described in terms of OBM elements, the method could be readily applied to other types of chemical therapy.

The sensing system 200 determines 240 a dose calibration curve for OBM elements. The sensing system 200 may determine the dose calibration curve based on some clinical data measuring the varying pharmacological responses in a clinical setting according to various dose amounts. The sensing system 200 may interpolate the dose calibration curve based on clinical data. For example, an OBM element is dosed in 5 mg, 10 mg, 15 mg, 20 mg, 25 mg, 30 mg, 35 mg, 40 mg, 45 mg, 50 mg, 55 mg, and 60 mg in clinical trials. The pharmacological response at each of those dose amounts is collected and then used to interpolate the dose calibration curve. In other embodiments, the dose calibration curve is generated by an OBM manufacturer (e.g., based on approved FDA dose amounts). The sensing system may update the dose calibration curve as new clinical data is retrieved.

The sensing system 200 generates 245 a measurement matrix at least based on the dose calibration curve. In other embodiments, there are additional considerations that may weigh into the measurement matrix determination. Example considerations include number of organisms included in the clinical trial, how many OBM elements under consideration, ensuring each compound is selected for approximately the same number of compound mixtures as other compounds, ensuring two or more compounds are not selected for two or more mixtures, optimizing for a maximum number of mixtures that may be tested. For example, how many organisms are included in the clinical trial may limit how many compound mixtures may be tested.

The sensing system 200 performs 250 clinical trials based on the measurement matrix, resulting in clinical data. In reality, the sensing system 200 may provide the compound mixtures to be dosed in the clinical setting to a clinical lab, where its technicians and/or scientists may perform the clinical trials. The clinical trials involve dosing based on the compound mixtures determined via the measurement matrix and recording pharmacological response of the organisms in response to the dosed compound mixtures. Some clinical trials may involve dosing an organism with different compound mixtures from the measurement matrix at different time periods. Other clinical trials may involve rotating the compound mixtures among a set of organisms to ensure each organism is dosed by each compound mixture.

The sensing system 200 trains 255 a predictive model based on the clinical data. As described above, the predictive model may be trained according to machine learning algorithms. In one embodiment of supervised training, the sensing system 200 generates a feature vector for each sample based on the dosed compound mixture. The sensing system 200 trains the predictive model to predict the observed pharmacological response based on the feature vector.

With the predictive model, the sensing system 200 may repeat steps of the method. For example, the sensing system 200 may update the dose calibration curve based on the predictive model and perform additional trials. In another example, the predictive model may be used to generate a new measurement matrix for additional clinical trials.

In one embodiment, the sensing system 200 determines 260 an optimal compound mixture for a treatment. The sensing system 200 may have one or more constraints used to identify a set of candidate compound mixtures that satisfy the constraints. The sensing system 200 may generate a feature vector for each candidate compound mixture and apply the predictive model to determine a predicted pharmacological response. Based on the predicted pharmacological responses, the sensing system 200 may identify one of the candidate compound mixtures as the treatment. Clinical trials may be used to validate the optimal compound mixture. Additional details are below in Section III.A (Optimizing Pharmacological Compound Development).

In another embodiment, the sensing system 200 determines 265 an optimal modification of a compound. In this embodiment, the OBM elements include various modifications to a compound. Some of the modifications may be tested in clinical trials. The predictive model may be used to determine an optimal modification of the compound. Additional details are below in Section III.B (Optimizing Compound Modifications).

In other embodiments, the sensing system 200 determines 270 an optimal therapy combination for a treatment. Under this embodiment, the sensing system 200 may consider different types of therapy for use in a treatment. The OBM elements may instead include the different types of therapy. Measurement matrix is generated to combine various types of therapy, trials are performed, and predictive model is trained based on the clinical data. The sensing system 200 then determines the optimal therapy combination. Additional details are below in Section III.C (Designing Treatments for a Disease or Condition).

II.B. Compounds

The compounds of the present disclosure include any compound for treating a disease or condition. For example, the compound can be any agent for treating a disease or condition.

In some embodiments, the number of compounds in a subset of compounds of the present methods include 2 or more compounds, 3 or more compounds, 4 or more compounds, 5 or more compounds, 6 or more compounds, 7 or more compounds, 8 or more compounds, 9 or more compounds, 10 or more compounds, 11 or more compounds, 12 or more compounds, 13 or more compounds, 14 or more compounds, or 15 or more compounds. In some embodiments, the number of compounds in a subset of compounds of the present methods include 2 or more compounds, 5 or more compounds, 10 or more compounds, 20 or more compounds 30 or more compounds, 40 or more compounds, 50 or more compounds, 60 or more compounds, 70 or more compounds, 80 or more compounds, 90 or more compounds, or 100 or more compounds. In some embodiments, the number of compounds in a subset of compounds of the present methods include 125 or more compounds, 150 or more compounds, 200 or more compounds, 225 or more compounds, 250 or more compounds, 275 or more compounds, 300 or more compounds, 325 or more compounds, 350 or more compounds, 375 or more compounds, 400 or more compounds, 425 or more compounds, 450 or more compounds, 475 or more compounds, or 500 or more compounds. In some embodiments, the number of compounds in a subset of compounds of the present methods include 550 or more compounds, 600 or more compounds, 650 or more compounds, 700 or more compounds, 750 or more compounds, 800 or more compounds, 850 or more compounds, 900 or more compounds, 950 or more compounds, or 1000 or more compounds. In some embodiments, the number of compounds in a subset of compounds of the present methods include 1000 or more compounds, 1500 or more compounds, or 2000 or more compounds.

In some embodiments, the number of compounds in a corresponding set of compounds of the present methods include 2 or more compounds, 3 or more compounds, 4 or more compounds, 5 or more compounds, 6 or more compounds, 7 or more compounds, 8 or more compounds, 9 or more compounds, 10 or more compounds, 11 or more compounds, 12 or more compounds, 13 or more compounds, 14 or more compounds, or 15 or more compounds. In some embodiments, the number of compounds in a corresponding set of compounds of the present methods include 2 or more compounds, 5 or more compounds, 10 or more compounds, 20 or more compounds 30 or more compounds, 40 or more compounds, 50 or more compounds, 60 or more compounds, 70 or more compounds, 80 or more compounds, 90 or more compounds, or 100 or more compounds. In some embodiments, the number of compounds in a corresponding set of compounds of the present methods include 125 or more compounds, 150 or more compounds, 200 or more compounds, 225 or more compounds, 250 or more compounds, 275 or more compounds, 300 or more compounds, 325 or more compounds, 350 or more compounds, 375 or more compounds, 400 or more compounds, 425 or more compounds, 450 or more compounds, 475 or more compounds, or 500 or more compounds. In some embodiments, the number of compounds in a corresponding set of compounds of the present methods include 550 or more compounds, 600 or more compounds, 650 or more compounds, 700 or more compounds, 750 or more compounds, 800 or more compounds, 850 or more compounds, 900 or more compounds, 950 or more compounds, or 1000 or more compounds. In some embodiments, the number of compounds in a corresponding set of compounds of the present methods include 1000 or more compounds, 1500 or more compounds, or 2000 or more compounds.

In some embodiments, the compound is an OBM. In some embodiments, OBMs of the present disclosure are oligonucleotides designed to engage with native DNA or RNA sequences in the cell by Watson Crick hybridization. In some embodiments, such hybridization results in enzymatic recruitment post-hybridization to achieve a biophysical function (e.g. desired function). In some embodiments, the biophysical function includes, but is not limited to, one or more of gene editing, gene express knock-down, gene expression upregulation, RNA splicing modulatory behavior, RNA-editing, protein specific targeting, receptor specific targeting, enzymatic substrate specific targeting, and distribution and update into tissues or cells.

In some embodiments, the oligonucleotide has a length ranging from 10 nucleotides to about 100 nucleotides. In some embodiments, the oligonucleotide has a length ranging from about 10 nucleotides to about 20 nucleotides, about 20 nucleotides to about 30 nucleotides, about 30 nucleotides to about 40 nucleotides, about 40 nucleotides to about 50 nucleotides, about 50 nucleotides to about 60 nucleotides, about 60 nucleotides to about 70 nucleotides, about 70 nucleotides to about 80 nucleotides, about 80 nucleotides to about 90 nucleotides, or about 90 nucleotides to about 100 nucleotides. In certain embodiments, the oligonucleotide has a length ranging from about 10 nucleotides to about 15 nucleotides, about 15 nucleotides to about 20 nucleotides, about 20 nucleotides to about 25 nucleotides, about 25 nucleotides to about 30 nucleotides, about 30 nucleotides to about 35 nucleotides, about 35 nucleotides to about 40 nucleotides, about 40 nucleotides to about 45 nucleotides, or about 45 nucleotides to about 50 nucleotides. In some embodiments, the length of the oligonucleotide ranges from 12 nucleotides to 22 nucleotides. In certain embodiments, the oligonucleotide has a length of from 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. In some embodiments, the oligonucleotide has a length of 12 nucleotides. In some embodiments, the oligonucleotide has a length of 13 nucleotides. In some embodiments, the oligonucleotide has a length of 14 nucleotides. In some embodiments, the oligonucleotide has a length of 15 nucleotides. In some embodiments, the oligonucleotide has a length of 16 nucleotides. In some embodiments, the oligonucleotide has a length of 17 nucleotides. In some embodiments, the oligonucleotide has a length of 18 nucleotides. In some embodiments, the oligonucleotide has a length of 19 nucleotides. In some embodiments, the oligonucleotide has a length of 20 nucleotides. In some embodiments, the oligonucleotide has a length of 21 nucleotides. In some embodiments, the oligonucleotide has a length of 22 nucleotides.

In some embodiments, an oligonucleotide includes, but is not limited, to an antisense oligonucleotide (ASO), anti-gene oligonucleotides, CpG oligonucleotides, single-guide RNA (sgRNA), dual-guide RNA, targeter RNA (e.g., targeted coding RNA such as a protein-encoding gene or targeted non-coding RNA), activator RNA, ribozymes, tracr RNA, CRISPR RNA (crRNA), ADAR RNA, and the like. Targeted non-coding RNA includes, but is not limited to, tRNA, rRNA, snoRNA, siRNA, miRNA, long ncRNA, etc). In some embodiments, the final set of oligonucleotides comprises a set of antisense oligonucleotides (ASO). In some embodiments, the final set of oligonucleotides comprises a set of anti-gene oligonucleotides. In some embodiments, the final set of oligonucleotides comprises a set CpG oligonucleotides. In some embodiments, the final set of oligonucleotides comprises a set of single-guide RNAs. In some embodiments, the final set of oligonucleotides comprises a set of dual-guide RNAs. In some embodiments, the final set of oligonucleotides comprises a set of ADAR guide RNAs. In some embodiments, the final set of oligonucleotides comprises a set of CRISPR guide RNAs. In some embodiments, the final set of oligonucleotides comprises a set of targeter RNAs. In some embodiments, the final set of oligonucleotides comprises a set of activator RNAs.

In some embodiments, the oligonucleotide is an antisense oligonucleotide (ASO). In some embodiments, ASO can bind to a messenger RNA (mRNA) produced by a gene and inactivate it, effectively turning that gene "off". In some embodiments, the strand may be targeted to bind to a splicing site on pre-mRNA and modify the exon content of an mRNA. In some embodiments, the ASO is an ASO gapmer.

In some embodiments, the oligonucleotide is a siRNA. In some embodiments, the oligonucleotide is a sgRNA. In some embodiments, the oligonucleotide is a dual-guide RNA. In some embodiments, the oligonucleotide is an anti-gene oligonucleotide. In some embodiments, the oligonucleotide is a CpG oligonucleotide. In some embodiments, the oligonucleotide is a targeter RNA. In some embodiments, the targeter RNA is a protein-encoding gene. In some embodiments, the targeter RNA is a non-coding RNA, such as, but not limited to, a tRNA, a rRNA, a snoRNA, an miRNA an siRNA, an RNAi, or a long ncRNA. In some embodiments, the oligonucleotide is a CRISPR RNA (crRNA). In some embodiments, the oligonucleotide is an ADAR RNA. In some embodiments, the oligonucleotide is an activator RNA. In some embodiments, the oligonucleotide is a ribozyme. In some embodiments, the oligonucleotide is an aptamer.

In some embodiments, the oligonucleotide is a sgRNA. In some embodiments, the sgRNA is a targeting sequence that hybridizes to a target sequence of a target DNA. In some embodiments, the sgRNA comprises a targeting sequence that hybridizes to a target sequence of a target DNA, and a protein-binding domain that interacts with a Cas9 protein. In some embodiments, the desired sgRNA increases site-specific modification of the target DNA, e.g., for example, by homologous directed repair (HDR), or non-homologous end joining (NHEJ). In some embodiments, the sgRNA comprises a targeting sequence that hybridizes to a target sequence of a target RNA, and facilitates interactions with an ADAR protein. In some embodiments, the desired sgRNA increases site-specific editing of the target RNA, e.g., for example, by A-to-I mediated ADAR editing.

In some embodiments, the oligonucleotide is a dual-guide RNA. A dual guide RNA can be designed using the method of the present disclosure to allow for controlled (i.e., conditional) binding of a targeter-RNA with an activator-RNA. Because a dual guide RNA is not functional unless both the activator-RNA and the targeter-RNA are bound in a functional complex with Cas9, a dual guide RNA can be inducible (e.g., drug inducible) by rendering the binding between the activator-RNA and the targeter-RNA to be inducible. As one non-limiting example, RNA aptamers can be used to regulate (i.e., control) the binding of the activator-RNA with the targeter-RNA. Accordingly, the activator-RNA and/or the targeter-RNA can include an RNA aptamer sequence.

In some embodiments, the oligonucleotide is an aptamer. In some embodiments, the oligonucleotide is an RNA aptamer. Aptamers are known in the art and are generally a synthetic version of a riboswitch. The terms "RNA aptamer" and "riboswitch" are used interchangeably herein to encompass both synthetic and natural nucleic acid sequences that provide for inducible regulation of the structure (and therefore the availability of specific sequences) of the nucleic acid molecule (e.g., RNA, DNA/RNA hybrid, etc.) of which they are part. RNA aptamers usually comprise a sequence that folds into a particular structure (e.g., a hairpin, stem-loop, pseudoknot, etc), which specifically binds a particular target molecule. In some embodiments, binding of the target molecule causes a structural change in the folding of the RNA, which changes a feature of the nucleic acid of which the aptamer is a part.

In some embodiments, the compound is a small molecule. In some embodiments, the compound is a biologic drug. In some embodiments, biologic drugs include, but are not limited to, vaccines, blood, blood components, cells, allergens, genes, tissues, and recombinant proteins.

In some embodiments, the compound is a polypeptide. In some embodiments, the polypeptide is an antibody. In some embodiments, the antibody is a complete antibody. In some embodiments, the antibody is a monoclonal antibody. In some embodiments, the antibody is a monoclonal antibody. In some embodiments, the polypeptide is an antibody fragment. In some embodiments, the antibody fragment is selected from the group consisting of: a Fab fragment, a F(ab')2 fragment, a single chain variable fragment (scFv), a scFv-Fc, an intrabody, a diabody, a triabody, a bispecific antibody or a chimeric antibody.

In some embodiments, the compound is an antigen-binding derivative. In some embodiments, the compound is a drug-antibody complex.

II.C. Effects

In some aspects, methods of the present disclosure include optimizing pharmacological compound development. In some aspects, the methods of the present disclosure include optimizing modifications of a compound.

In some embodiments, the methods of the present disclosure include accessing, for each compound of a plurality of compounds, information describing an effect of the compound. In some embodiments, the methods of the present disclosure include accessing, for each compound of a plurality of compounds, effect information describing an effect of the compound.

In some embodiments, the effect is of each individual compound. In some embodiments, the effect is between the compounds within the subset of compounds. In some embodiments, the effect is between the compounds within the corresponding set of compounds.

In some embodiments, the effect is selected from: a biophysical effect, a synergistic or antagonistic effect, and a combination thereof. In some embodiments, the effect information is selected from: a biological effect, a chemical effect, and a pharmacological effect, in combination with synergistic or antagonistic effects between compounds of the corresponding set of compounds. In some embodiments, the biophysical effect is a biological effect, a chemical effect, or a pharmacological effect. In certain embodiments, the pharmacological effect is a pharmacodynamic interaction between the compounds within the subset of compounds. Synergistic or antagonistic effects, used in its conventional sense, are interactions that cannot be quantified by parameters for additive weights of effect of individual compounds alone, but require additional parameters quantifying non-additive interactions between the compounds for the effect.

In some embodiments, a synergistic or antagonistic effect is a positive or negative interaction between two or more drugs that causes the total effect of the compounds to be greater or lesser than the sum of the individual effects of each compound, respectively. For example, a mechanism underlying synergies is the effect of the drugs on the same receptor but on distinct binding sites and causing distinct molecular biology processes. An example is greatly enhancing GABAergic neurotransmission with two drugs which have distinct binding sites on the GABAA receptor. The GABAA receptor is a ligand-gated-ion channel; the ligand is GABA and the important ion is chlorine. Benzodiazepines increase the frequency of the receptor's chloride channel opening, whereas barbiturates increase the duration of the chloride channel opening on being GABA-bound. These two drugs have distinct binding sites, and produce distinct effects when bound, but together they have much stronger effects (hence synergy) than the sum of individual effects. A mechanism of antagonistic effect is competitive binding to the same receptor site by drugs of opposite effects. Antagonism may also occur owing to direct interactions between the drugs leading to neutralizing their active sites to the receptor. Antagonistic interaction can also occur at physiological response level: for example, digoxin and furosemide interactions. Digoxin, used in the treatment of heart conditions, has an increased effect at low levels of potassium in blood plasma. Furosemide, used as a diuretic, used to treat fluid build-up due to heart failure, lowers arterial tension but favours the loss of potassium. Administered together, the drugs could lead to hypokalemia (low levels of potassium in the blood), which could increase the toxicity of digoxin, and therefore are physiologically antagonistic. Recently, synergistic and antagonistic drug interactions in the treatment of systemic fungal infections (in immunocompromised individuals) were studied in mice using the common antifungal fluconazole in two-drug-combination drawn from a library of 2000 other drugs. Notably, both antagonistic and synergistic combinations were discovered from such a screening, with dicyclomine and fluconazole being synergistic, whereas nafcillin and fluconazole being antagonistic in effect. In some embodiments, the biophysical effect is a toxicity or an immune response of the subset of compounds.

In some embodiments, biophysical effect is a toxicity or an immune response of each individual compound. In some embodiments, the biophysical effect is a toxicity or an immune response between compound modification combinations. In some embodiments, biophysical effect is a toxicity or an immune response of each individual modification of the compound.

In some embodiments, the effect is a synergistic or antagonistic effect between two or more compounds of the corresponding set of compounds.

In some embodiments, the pharmacological effect is a pharmacodynamic interaction between the compounds within the subset of compounds. In some embodiments, the pharmacological effect is a pharmacodynamic interaction between compound modification combinations.

In some embodiments, an association between the effects is the interaction between each of the plurality of compounds that produce a positive or negative biophysical effect on the safety or efficacy of the combined compounds. The term "association", as used in the present disclosure, can refer to a quantitative mapping or other quantitative relationship between compound and effect. In some embodiments, the interaction is a chemical interaction, a molecular interaction, a toxic interaction, a synergistic or antagonistic interaction, or a combination thereof.

In some embodiments, the effect is a synergistic or antagonist effect between compound modification combinations. In some embodiments, the effect is of each individual modification on the compound. In some embodiments, the effect is between the modifications within the compounds. In but one, non-limiting example, consider that 2'-OMe (2'-O-Methyl, a sugar modification) modification of phosphorothioate (PS, a backbone modification)-modified oligonucleotides have antagonistic effects in cytotoxicity; the latter increases cytotoxicity while the former decreases toxicity when applied to specific positions in the oligonucleotide sequence. In another non-limiting example, a chiral-controlled PS (Rp or Sp) can be synergistic or antagonistic in antisense oligonucleotides (ASO), depending on the position of such modification in the ASO, with respect to the cleavage efficiency by RNase H and thereby its mechanism of drug action. In yet another non-limiting example, 2'-OMe and 2'-Fluoro modifications have sequence-positions dependent antagonistic or synergistic effects in siRNA drug design, as measured by a wide-range of pharmacological endpoints.

In some embodiments, the effect is affinity maturation of the compound. In some embodiments, the effect is a stability of the compound. In some embodiments, the effect is a conjugation reaction of the compound to a moiety.

In some embodiments, the biophysical effect is a tolerability measure. In some embodiments, tolerability, used in its conventional sense, refers to the degree to which an adverse effect of the oligonucleotide can be tolerated. In some embodiments, the tolerability includes toxicity. In some embodiments, toxicity comprises cytotoxicity. In some embodiments, toxicity comprises membrane toxicity. In some embodiments, toxicity comprises immunotoxicity. For example, tolerability can include the degree to which toxicity can be tolerated.

In some embodiments, the toxicity is membrane toxicity. As used herein, and in its conventional sense, "membrane toxicity" refers to the ability of a toxicity-induced change to occur to the cell membrane. Such changes to the cell membrane can include, but are not limited to, a change in the normal flux of ions, a change related to cell membrane fluidity, a change related to ion channels in the cell membrane, and the like. In some embodiments, the biophysical effect is tolerability. In some embodiments, the tolerability is one or more of: an effect that inhibits the normal flux of ions and an effect that inhibits membrane fluidity. In some embodiments, the tolerability is the effect that inhibits the normal flux of ions. In some embodiments, the tolerability comprises an effect that inhibits membrane fluidity. In some embodiments, a biophysical effect comprises a membrane fusion and fission event. In some embodiments, the membrane fusion and fission event result in loss of cellular signaling activity.

In some embodiments, membrane toxicity or membrane tolerability is measured by dysregulation of neuronal depolarization. Neuronal depolarization includes, but is not limited to, pre-synaptic, post-synaptic, and channel-related action potentials. In some embodiments, membrane toxicity comprises one or more of: pre-synaptic, post-synaptic, and channel-related action potential dysregulations by the oligonucleotide. In some embodiments, membrane toxicity includes, but is not limited to, depolarization by compounds, such as presynaptic, post-synaptic, channel relation action potential dysregulations by compounds in electrically excitable cells. In some embodiments, electrically excitable cells include, but are not limited to, neurons, muscle cells, such as skeletal, and cardiac cells. In some embodiments, membrane toxicity or tolerability includes, but is not limited to, membrane potential events. In some embodiments, membrane potential events can occur in electrically excitable cells. In some embodiments, membrane toxicity or tolerability comprises membrane potential dysregulation in the kidneys. In some embodiments, membrane toxicity or tolerability comprises membrane potential dysregulation in hepatocytes.

In some embodiments, toxicity comprises cytotoxicity. In some embodiments, cytotoxicity is measured by an apoptotic response in a cell. In some embodiments, cytotoxicity comprises metabolic toxicity. In some embodiments, cytotoxicity comprises cell organelle toxicity, for example in systemic and neuronal tissues. In some embodiments, cytotoxicity comprises receptor-specific toxicity, for example, in systemic and neuronal tissues. In some embodiments, cytotoxicity comprises mitochondrial toxicity. In some embodiments, cytotoxicity comprises cell-surface receptor-mediated toxicity. In some embodiments, cytotoxicity is measured by mis-localization, accumulation, granules/paraspeckles associated with toxicity. In some embodiments, the cytotoxicity is one or more selected from a liver toxicity measured, for example, a an amount of ALT, an amount of AST, or a ratio of ALT to AST; a kidney toxicity measured by, for example, an amount of blood urea nitrogen (BUN), creatinine, or a ratio of BUN to creatinine; and a neurotoxicity measured by microglia activation, for example, gene expression, neuronal cell loss, or histology, and a combination thereof. Cytotoxicity can be measured using any conventional method known in the art.

In some embodiments, toxicity comprises immunotoxicity. In some embodiments, the toxicity is an immunotoxicity.

In some embodiments, toxicity comprises membrane toxicity. In some embodiments, the toxicity is a membrane toxicity.

In some embodiments, the biophysical effect is an immunostimulatory and/or immunogenic modulation. In some embodiments, an immunostimulatory effect is measured by an immune response. In some embodiments, the immunostimulatory modulation is an increase in an immune response. In some embodiments, an immunostimulatory modulation is a decrease in an immune response. In some embodiments, the immune response is sequence dependent. In some embodiments, the immune response is chemistry dependent. In some embodiments, the immune response is sequence and chemistry dependent. In some embodiments, the immune response includes cytokine stimulation and/or release. In some embodiments, an immune response is determined by cytokine stimulation and/or release. In some embodiments, an immune response is determined by platelet effects. In some embodiments, an immune response is determined by macrophage activation. In some embodiments, macrophage activation is in response to innate nonself and/or danger signals that are patient-specific. In some embodiments, an immune response is determined by microglial activation in the brain. In some embodiments, an immune response is determined by activation of resident macrophages, such as, but not limited to liver kupffer cells, lung macrophages, and the like. In some embodiments, an immunostimulatory effect or immunogenic effect is determined by adaptive immune system related effects. In some embodiments, immunostimulatory modulation and/or immunogenic modulation is determined by one or more of: immune system related effects, stimulating the effect of anti-drug antibodies, and triggering anti-drug antibody inflammatory signaling. In some embodiments, the biophysical effect is an immune-mediated response. In some embodiments, the biophysical effect is an increase in immune-mediated response. In some embodiments, a biophysical effect is a reduction of immune-mediated inflammation.

In some embodiments, the biophysical effect is a measure of absorption, distribution, metabolism, or excretion of the oligonucleotide. In some embodiments, the biophysical effect is a measure of absorption, distribution, metabolism, or excretion of the oligonucleotide in one or more of: a tissue, cell, intracellular space, and extracellular space. The intracellular space can include any intracellular fluid within the cell. In some embodiments, the extracellular space includes any extracellular fluidic between the cells. In some embodiments, the intracellular fluid includes, but is not limited to, blood or cerebrospinal fluid (CSF). In some embodiments, the extracellular fluid includes, but is not limited to, interstitial fluid, plasma, lymph, cerebrospinal fluid (CSF), and milk. In some embodiments, the biophysical effect is a measure of pharmacokinetics or pharmacodynamics, and comprises one or more of: substrate-target processing, dynamics, accessibility, inter-cellular distribution, intra-cellular distribution, and time-dependent availability.

In some embodiments, the biophysical effect is absorption. In some embodiments, absorption is determined by the amount of cellular uptake and accumulation of oligonucleotides generally into cells. In some embodiments, absorption is determined by the amount of cellular uptake and accumulation into a desired cellular compartment, such as membrane bound (e.g. nucleus, cytoplasm, mitochondria) and non-membrane bound organelles (e.g., ribosomes, P-bodies, paraspeckles, nucleoli, stress granules). In some embodiments, absorption is determined by optimization of the time it takes for an oligonucleotide to absorb into tissue beds, cells, or eventual subcellular localization.

In some embodiments, the biophysical effect is distribution. In some embodiments, the distribution is determined by the transportation of the oligonucleotide from the site of dosing to cells, tissues, or other structures either selectively or generally. In some embodiments, the site of dosing includes the site of delivery of the oligonucleotide. In some embodiments, the oligonucleotide is administered by, for example, oral delivery, systemic delivery, intravenous delivery, or intrathecal injection. In some embodiments, the oligonucleotide is delivered via local administration, such as, but not limited to aerosol exposure, topical or dermal ointments, or tumor injections, to cells, tissues or other structures either selectively or generally. In some embodiments, distribution is determined by binding to and subsequent release from proteins or cells that facilitate transportation of oligonucleotides from one place in the organism to another (e.g. binding to a protein or cell that transits OBMs from the blood to the CSF).

In some embodiments, the biophysical effect is metabolism. In some embodiments, metabolism is controlled by the stability of the oligonucleotide (e.g. as a whole, in partial form, or in a specific confirmation). Non-limiting examples include, but are not limited to: controlling of how long an oligonucleotide persists in the cell, blood, CSF or other biofluid; targeting moieties, such as aptamers, may be optimized to degrade at a differential rate, or at a different time, or place than the oligonucleotide; oligonucleotide conformational changes may be desired and facilitated by differential metabolism of the oligonucleotide that would activate the oligonucleotide by exposing/releasing an active substructure, or separate oligonucleotide; and control of what metabolites are produce. In some embodiments, controlling what breakdown products are created by the oligonucleotide enhances the safety of the oligonucleotide.

In some embodiments, the biophysical effect is excretion. In some embodiments, excretion is determined by controlling how either whole or metabolites of the source oligonucleotides are removed from the organism. In some embodiments, the biophysical effect of excretion is optimized to enhance bile or urine removal.

In some embodiments, the biophysical effect is a biological activity of the oligonucleotide (e.g., functionality). Accordingly, it should be noted that in some embodiments, the terms "biological activity" and "biophysical functionality" can refer to a type of biophysical effect described herein. In some embodiments, the biophysical effect is selectivity of the oligonucleotide to the target. In some embodiments, the biophysical effect is inactivity of the oligonucleotide. In some embodiments, the biophysical effect is lack of selectivity to the target.

In some embodiments, the biological activity comprises an off-target engagement of the oligonucleotide to a target molecule. As used herein and in its conventional sense, "off-target", refers to a lack of selectivity to a target, which, for example, causes an oligonucleotide to affect a non-target molecule (e.g. non-target gene). In some cases, the non-target molecule is a non-target gene. In some cases, lack of selectivity to a target is caused by the same on-target mechanism for on-target engagement (e.g., RNAse H1-mediated mechanism, and the like). In some cases, lack of selectivity to a target is caused by a different mechanism than the intended on-target mechanism for on-target engagement. In some embodiments, the off-target engagement causes the oligonucleotide to perform an effective amount of one or more of: non-target gene expression knock-down, non-target RNA splicing modulatory behavior, non-target gene expression upregulation, non-target gene-editing, non-target RNA-editing, non-target protein specific targeting, non-target receptor specific targeting, non-target enzymatic substrate specific targeting, non-target distribution and uptake into tissues or cells, and non-target interaction with a specific protein or receptor. In some embodiments, off-target engagement is measured by transcriptome-wide gene expression readouts. In some embodiments, off-target engagement of the oligonucleotide to the target is measured by unintended splicing modulation readouts transcriptome-wide. In some embodiments, off-target engagement is measured by biophysical readouts of sequence/edit tolerance of relevant enzymes RNaseH, Ago2 spliceosome factors, and the like.

In some embodiments, the biological activity comprises an on-target engagement of the oligonucleotide to a target molecule. In some embodiments, the on-target engagement causes the oligonucleotide to perform an effective amount of one or more of: gene expression knock-down, RNA splicing modulatory behavior, gene expression upregulation, gene-editing, RNA-editing, interaction with a specific protein or receptor, protein specific targeting, receptor specific targeting, enzymatic substrate specific targeting, and distribution and uptake into tissues or cells.

In some embodiments, the on-target engagement comprises an amount (e.g. %) of gene expression knock-down. In some embodiments, gene expression knock-down can be measured using conventional methods known in the art. In some embodiments, gene expression knock-down is measured by RNAse H1 dependent RNA cleavage. In some embodiments, gene expression knock-down is measured by RNA-Induced Silencing Complex (RISC)-dependent RNA cleavage. In some embodiments, the biophysical effect is RNase H-mediated degradation in the nuclease.

In some embodiments, the on-target engagement comprises an amount of splicing modulatory behavior. RNA mis-splicing causes a large array of human diseases due to hereditary and somatic mutations. In some embodiments, the biophysical effect comprises recognition of specific RNA splicing regulatory elements to modulate splicing. In some embodiments, the biophysical effect is the amount of splicing modulatory behavior that drives preferential expression of an alternative splice isoform. In some embodiments, the biophysical effect is the amount of splicing modulatory behavior that drives preferential co-transcriptional induction of nonsense-mediated decay.

In some embodiments, the on-target engagement comprises the amount (e.g. %) of gene expression up-regulation. In some embodiments, on-target engagement is the amount of gene expression upregulation determined by stabilization of RNA through reduction of endogenous RNA degradation pathways, such as, but not limited to, miRNA directed RISC cleavage, protracted maintenance of polyA tails, and stabilization of RNA structures, including polysome formation. In some embodiments, on-target engagement is the amount of gene expression upregulation determined by enhanced translation through blockage of non-productive uORFs. In some embodiments, on-target engagement is the amount of gene expression upregulation determined by OBM-directed recruitment of nuclear factors. In some embodiments, OBM directed recruitment of nuclear factors is determined by directly binding DNA. In some embodiments, OBM directed recruitment of nuclear factors is determined by indirectly binding DNA through interactions that orchestrate productive chromatin organization or dynamics.

In some embodiments, on-target engagement comprises an amount of gene-editing. In some embodiments, gene-editing is achieved by CRISPR (Clustered Regularly Interspaced Short Palindromic Repeats)/Cas and CRISPR-like enzymatic processes. In some embodiments, gene editing is achieved by engagement with other endogenous DNA repair and editing mechanisms, such as, but not limited to, zinc-finger nucleases (ZFNs) and transcription activator-like effector nucleases (TALENs). Using a guide RNA, Cas9 can modify (e.g. cleave) double-stranded DNA at any site, defined by the guide RNA sequence, and including a protospacer-adjacent (PAM) motif. A Cas9/guide RNA complex (i.e.g a Cas9 targeting complex) constitutes a simple and versatile RNA-directed system for modifying target DNA, or modifying proteins associated with target DNA, in any desired cell or organism. Additionally, a Cas9 targeting complex having a mutated Cas9 protein with reduced or removed nuclease activity can still bind to target DNA.

In some embodiments, the biophysical effect is an amount of RNA-editing achieved. In some embodiments, the amount of RNA-editing is determined by engagement with adenosine deaminase acting on RNA (ADAR) or other RNA editing enzyme systems conventionally known in the art.

In some embodiments, the biophysical effect is interaction with a specific protein or receptor. In some embodiments, the biophysical effect is one or more of: protein specific targeting, receptor specific targeting, or enzymatic substrate specific targeting.

In some embodiments, the biophysical effect is one or more nucleotide sequences and/or chemical mutations configured to improve its biophysical function. In some embodiments, the biophysical effect is 2 or more, 3 or more, 4 or more, 5 or more, 6 or more, 7 or more, 8 or more, 9 or more, or 10 or more nucleotide sequence or chemical mutations configured to improve its biophysical function. In some embodiments, the biophysical effect is 1 to 3 mutations, 3 to 5 mutations, 5 to 10 mutations, 10 to 15 mutations, 15 to 20 mutations, 20 to 25 mutations, or 25 to 30 mutations.

In some embodiments, the biophysical effect is the efficacy of aptamers. In some embodiments, the efficacy of aptamers is measured by the binding activity to a target molecule (e.g. a synthetic protein, natural protein or nucleic acid). In some embodiments, the efficacy of the aptamer is measured by, for example, non-specific (e.g. intra and inter-) tissue-specific distribution and/or uptake; non-specific cellular-specific distribution and/or uptake, and/or non-specific cell organelle-specific distribution and/or uptake. In some embodiments, the efficacy of the aptamer is measured by binding affinity to miRNAs, ncRNAs/regulatory RNAs, and the like. In some embodiments, the efficacy of the aptamer is measured by the aptamer tertiary structure interaction with a target molecule (e.g. OBM). In some embodiments, the biophysical property of the aptamer comprises the amount of cellular uptake and trafficking of the aptamer. In some embodiments, the biophysical effect of the aptamer comprises OBM-aptamer interactions. In some embodiments, the biophysical effect of the aptamer comprises the folded structures of the aptamer. In some embodiments, the folded structures are secondary and/or tertiary structures. In some embodiments, the folded structure comprises one or more of a bulge, an apical loop, a stem-loop, a 3-way junction, a form helix, an internal loop, a pseudoknot, a hairpin, G-quadruplexes, and a combination thereof. In some embodiments, the biophysical effect of the aptamer is the electrostatic interactions of the aptamer. In some embodiments, the biophysical effect of the aptamer is the hybridization energetics and biophysics of the aptamer.

In some embodiments, the biophysical effect is one or more of: cellular uptake and trafficking of the aptamer, binding affinity to the OBM, OBM-aptamer interactions, folded (e.g. secondary, tertiary) structures of the aptamer, electrostatic interactions, and hybridization energetics and biophysics.

In some embodiments, the biophysical function comprises a reduction of immune-mediated inflammation. In some embodiments, the biophysical function comprises an increase in immune-mediated responses.

In some embodiments, the biophysical function is an on-target engagement of the oligonucleotide to a target. In some embodiments, the on-target engagement causes the oligonucleotide to perform an effective amount of one or more of: gene expression knock-down, RNA splicing modulatory behavior, gene expression upregulation, gene-editing, RNA-editing, protein specific targeting, receptor specific targeting, enzymatic substrate specific targeting, and distribution and uptake into tissues or cells.

In some embodiments, the target is a gene product. In some embodiments, the gene product is one or more of: an mRNA, a splicing site on a pre-mRNA, a truncated transcript, an aborted transcription product, or an antisense transcript. In some embodiments, the gene product is a divergent antisense transcript. In some embodiments, the gene product is a convergent antisense transcript.

In some embodiments, the biophysical function is a toxicity threshold (e.g. cytotoxicity, immunotoxicity, membrane toxicity) that is lower than a reference toxicity threshold.

In some embodiments, the biophysical function is an increase in site-specific modification of the target molecule.

In some embodiments, the biophysical function is the targeting of a gene associated with a genetic disease (e.g. common or rare genetic disease).

Aspects of the present disclosure include methods for optimizing combinatorial design and testing, wherein individual design contributions are efficiently deconvolved from a combination of two or more design elements comprising the steps of: providing a reference prior that is approximately sparse; calibrating the readout to the reference to determine the range of min to max for each individual design element; generating a custom measurement matrix specification using the parameters determined in step (b) and loading the generated positive measurement matrix into a computing device; physically combining the design elements in the proportions determined in step (c); collecting measurements for each mixture experiment as determined in step (c); reconstructing individual measurements from the mixture experiment; and optimizing the measurement matrix based on the determined measurements of step (e) and repeating steps (d)-(f). In some embodiments, the total number of experiments are fewer than the total number of design elements combined, or fewer than the number of total parameters to be learned.

Aspects of the present disclosure include methods for deconvoluting individual pharmacological properties of a therapeutic intervention from testing combinations comprising two or more independent therapeutic interventions, comprising the steps of: providing a reference prior that is approximately sparse; calibrating the readout to the reference to determine the range of min to max dosing and mixing number for each therapeutic intervention; generating a custom measurement matrix specification using the parameters determined in step (b) and loading the generated positive measurement matrix into a computing device; physically combining the therapeutic intervention in the proportions determined in step (c); determining measurements of each combination experiment as determined in step (c); reconstructing individual measurements from the combination experiment; and updating and extending the measurement matrix based on the determined measurements of step (e) and repeating steps (d)-(f) until individual measurements are reconstructed for each therapeutic intervention in the mixture. In some embodiments, wherein the total number of experiments are fewer than the total number of drugs combined, or fewer than the number of total parameters to be learned.

Aspects of the present disclosure includes methods for deconvoluting synergistic or antagonistic pharmacological properties of therapeutic intervention from testing one or more combinations comprising two or more independent therapeutic interventions, comprising the steps of: providing a reference prior that is approximately sparse; calibrating the readout to the reference to determine the range of min to max dosing and mixing number for each therapeutic intervention; generating a custom positive measurement matrix specification using the parameters determined in step (b) and customized to optimally detecting synergistic or antagonistic effects, and loading the generated positive measurement matrix into a computing device; physically combining the therapeutic intervention in the proportions determined in step (c); determining measurements of each combination experiment as determined in step (c); reconstructing individual measurements from the combination experiment; and updating and extending the measurement matrix based on the determined measurements of step (e) and repeating steps (d)-(f) until individual measurements are reconstructed for each therapeutic intervention in the mixture. In some embodiments, the total number of experiments are fewer than the total number of individual and synergistic and/or antagonistic parameters to be learned.

III. A. Optimizing Pharmacological Compound Development

Aspects of the present disclosure include optimizing pharmacological compound development by screening for (e.g., creating data information for) mixtures of compounds and building predictive models of pharmacology to reduce the number of experiments required to test during compound development.

In some embodiments, the method comprises accessing, for each compound of a plurality of compounds, information describing an effect of the compound.

In some embodiments, the effect is of each individual compound. In some embodiments, the effect is between the compounds within the subset of compounds. In some embodiments, the effect is selected from: a biophysical effect, a synergistic or antagonistic effect, and a combination thereof. In some embodiments, the biophysical effect is a biological effect, a chemical effect, or a pharmacological effect. In some embodiments, the pharmacological effect is a pharmacodynamic interaction between the compounds within the subset of compounds. In some embodiments, the biophysical effect is a toxicity or an immune response of the subset of compounds. In some embodiments, biophysical effect is a toxicity or an immune response of each individual compound.

In some embodiments, for each of the one or more effects of a compound, a distribution of compounds in the plurality of compounds that cause an above-threshold measure of the effect is sparse.

In some embodiments, the accessed information comprises a qualitative prior configured to estimate a sparsity level and determine the matrix size. In some embodiments, the accessed information comprises in vivo, in vitro, and/or in silico experiments based on pharmacological, medicinal chemistry, biophysics, and synthesis constraints of the plurality of compounds.

In certain embodiments, accessing information describing the effect of the compound comprises accessing qualitative and/or quantitative priors. In some embodiments, qualitative priors include any data information constraints about the compounds, such as, but not limited to, its biological activity, pharmacology, pharmacodynamics, toxicity, immunoactivity, tolerability, synergistic or antagonistic activities, and the like. In some embodiments, the qualitative prior can include known, safe, concentration range constraints of each compound.

In some embodiments, qualitative priors can be used in the present methods to estimate the sparsity level and decide upon the measurement matrix size accordingly (i.e., number of experiments to be done). In some embodiments, the qualitative prior is a synergistic or antagonistic activity between the mixture of compounds within the subset of compounds.

In some embodiments, the qualitative prior is a in vivo, ex-vivo, in vitro, and/or in silico prior. In some embodiments, in vivo priors include in vivo data information that were performed on, for example, non-human mammals, mammals, rodents, rats, mice, humans, e.g. rats, mice, pigs, cows, goats, sheep, non-human primates, fish, frogs, vertebrates, and the like.

In some embodiments, the in vitro data information includes in vitro data information that were performed in, for example, eukaryotic single-cell organism, a somatic cell, a germ cell, a stem cell, a plant cell, an algal cell, an animal cell, an invertebrate cell, a vertebrate cell, a fish cell, a frog cell, a bird cell, a mammalian cell, a pig cell, a cow cell, a goat cell, a sheep cell, a rodent cell, a rat cell, a mouse cell, a non-human primate cell, or a human cell. In some embodiments, the in vitro data information includes in vitro data information that were performed in cardiomyocytes, neurons, liver cells, pancreatic cells, blood cells, mesenchymal stem cells, skeletal muscle cells, glial cells, spinal cord cells, cardiac cells, skin cells, lung cells, epithelial cells, and combinations thereof. In some embodiments, the in vitro data information includes in vitro data information that were performed in CHO cells, BHL-21, AHL-1, MA-104, Vero, OK, AB9, and combinations thereof.

In some embodiments, the in vitro data information includes in vitro data information that were performed in human cell lines. In some embodiments, human cell lines include, but are not limited to, A431, A549, A172, A2780, A875, BCP-1, BJAB, Caco-2, Cal-27, Calu-3, CML T1, COR-L23, COV-434, DAOY, DU145, DuCaP, EM-2, EM-3, FM3, H1299, HaCaT, HCA2, HEK 293, HEK 2931, HL-60, HL-1080, HT-29, JU, K562, KBM-7, KCL-22, KG1, Ku812, KYO-1, LNCaP, Ma-Mel cell lines, MCF-7, MCF-10A, MDA cell lines, MG63, MIA PaCa-2, MQR/0.2R, Mono-Max-6, MRC-5, NCI cell lines, NALM-1, NK-92, NTERA-2, NW-145, OPCN/OPCT cell lines, PANC-1, PC-3, PNT1A, Raji, SaOS-2, SH-SY5Y, AiHa, SK (Sloan Kettering cancer cell lines), T2, T-47D, T84, T98G, THP-1, U205, U373, U87, U937, VCaP, VG-1, WM39, WT-49, YAR, and combinations thereof.

In some embodiments, the in vitro data information includes in vitro data information that were performed in mouse cell lines. In some embodiments, mouse cell lines include, but are not limited to, 3T3-L1, 4T1, A20, ALC, B16, bEND.13, C2C12, C3H-10T1/2, CGR8, CT26, E14Tg2a, EL4, EMT6 cell lines, GL261, Hepa1c1c7, J558L, L1210, L243, MA2.1, MC-38, MTD-1A, MyEND, Neuro-2a, NIH-3T3, Px63Ag8, RenCa, RIN-5F, RMA-S, YAC-1, and combinations thereof. In some embodiments, the in vitro data information includes in vitro data information that were performed in rat cell lines. In some embodiments, rat cell lines include, but are not limited to, A-10, 9L, B35, C6, PC-12, RBL-1, L2, L6, S16, BRL3A, S16Y, S42, F98, R4-6A2, RL-65, N1-S1, RFL-6, NRK, R2C, MH1C1, CA-77, Rat2, CTX TNA2, RIN-5F, UMR-106, RSC96, XC, RG2, GH4C1, GH3, AR42J, 2.43, RC-4B/C, NBT-II, RLE-6TN, GK1.5, R1-2, D1 TNC1, A7r5, 1D3, PC-12, RIN-m, NR8383, S42, RIN-14B, H9c2, RK3E, and combinations thereof.

In some embodiments, the in vitro data information includes in vitro data information that were performed in primary culture, including but not limited to, primary culture of cortical neurons, hippocampal neurons, iPSC derived differentiated cells, and combinations thereof.

In some embodiments, the method includes (a) determining, for each compound, a corresponding minimum amount of the compound required to produce an above-threshold effect and a maximum amount of the compound that can be administered to a subject. In some embodiments, the above-threshold effect is a toxicity threshold effect, a biological activity threshold effect, a distribution threshold effect, a metabolism threshold effect, an excretion threshold, a pharmacokinetics/pharmacodynamic threshold effect, or an absorption threshold effect. In some embodiments, the maximum amount is determined by the maximum concentration of the compound of the subset of compounds that can be administered to the subject. A non-limiting example of determining, for each compound, a corresponding minimum amount of the compound required to produce an above-threshold effect and a maximum amount of the compound that can be administered to a subject, is described in FIG. 1B.

In some embodiments, the method includes training an initial compound model based on the accessed information, the initial compound model identifying a first set of compound combinations, each compound combination including a subset of compounds, the number of compounds in each subset of compounds based on the minimum amount and maximum amount corresponding to each compound in step (b).

In some embodiments, the method includes, for each compound combination in the first set of compound combinations: accessing a set of effects caused by an application of the subset of compounds included in the compound combination; and determining an association, for each effect of the subset of effects, between the effect and the compound of the subset of compounds that caused the effect; retraining the initial compound model based on the determined association between effects and compounds; determining a target set of effects; and selecting one or more compounds of the plurality of compounds for administering to a target subject by applying the retrained compound model to the target set of effects.

In some embodiments, the compound model includes a matrix. In certain embodiments, the matrix is based on the accessed information, each column of the matrix corresponding to a compound that can be included in the subset of compounds, and each row of the matrix corresponding to an experiment associated with each subset of compounds.

In some embodiments, the experiment associated with a subset of compounds comprises a concentration of each compound within the subset of compounds. In some embodiments, the matrix comprises a plurality of experiments. In certain embodiments, the plurality of experiments comprises 2 or more experiments, 3 or more experiments, 4 or more experiments, 5 or more experiments, 10 or more experiments, 15 or more experiments, 20 or more experiments, 50 or more experiments, or 100 or more experiments. In certain embodiments, the plurality of experiments comprises 125 or more experiments, 150 or more experiments, 175 or more experiments, 200 or more experiments 225, or more experiments, 250 or more experiments, 275 or more experiments, 300 or more experiments, 325 or more experiments, 350 or more experiments, 375 or more experiments, 400 or more experiments, 425 or more experiments, 450 or more experiments, 475 or more experiments, or 500 or more experiments. In some embodiments, the plurality of experiments comprises 550 or more experiments, 600 or more experiments, 650 or more experiments, 700 or more experiments, 750 or more experiments, 800 or more experiments, 850 or more experiments, 900 or more experiments, 950 or more experiments, or 1000 or more experiments. In some embodiments, the plurality of experiments comprises 1000 or more experiments, 1500 or more experiments, or 2000 or more experiments.

In some embodiments, every compound in the subset of compounds is included in an identical number of experiments. In some embodiments, every experiment in the matrix has a fixed number of compounds.

Figure 13:
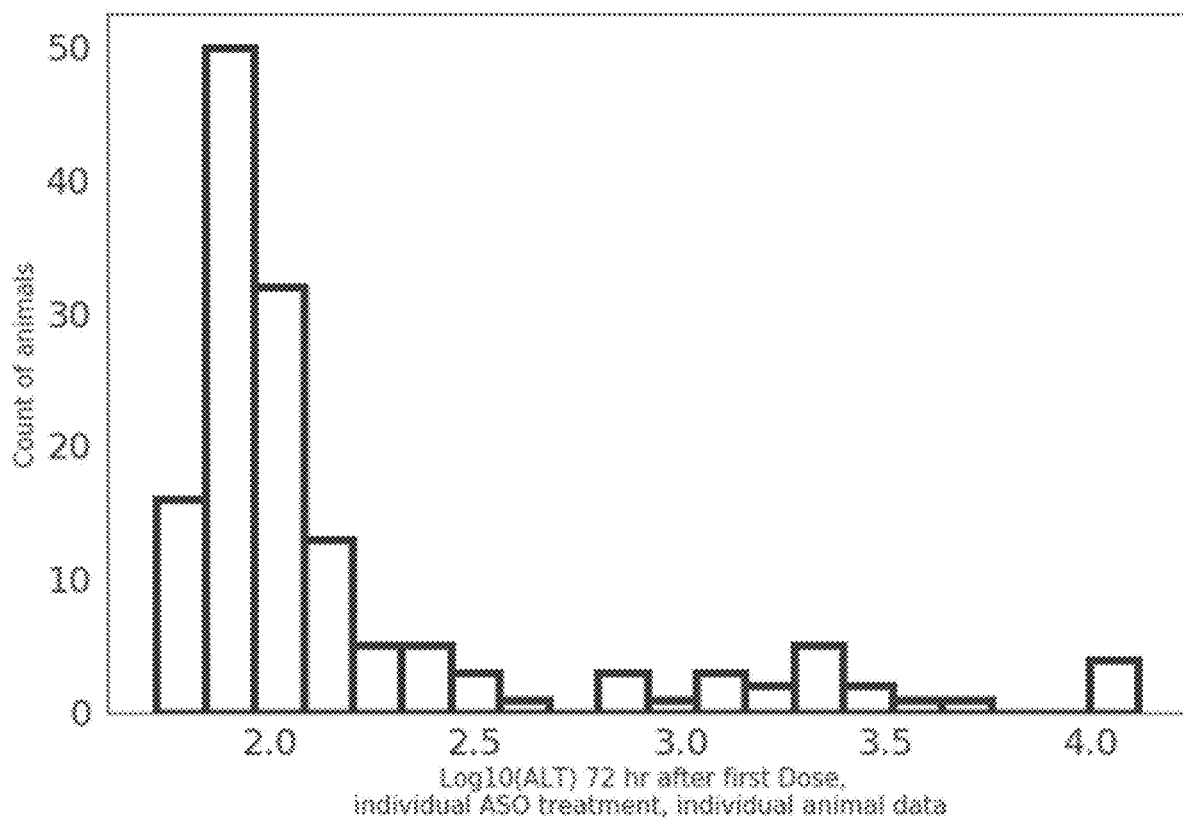
FIG. 13 illustrates liver toxicity in response to dosing. The frequency distribution of ALT (Alanine Aminotransferase, in u/L, a common measure of liver toxicity) measures in mice 72 hrs after first dose (at 75 mg/kg of each of the 48 ASOs, in 3 animal replicates, individual animal level data shown), measured in blood. "Safe" ALT levels are 50-100 u/L. Notice that the distribution is approximately sparse (in deviation from safe values).

In some embodiments, the method comprises a constraint such that no two compounds are in more than 1 experiment. In a non-limiting example, the methods can incorporate the prior distribution of measurements, modelled as a mixture distribution of (a) Gaussian dense components approximately, and not exactly, zero and (b) an arbitrary distribution of sparse components. The algorithm as described in FIG. 13 makes a maximum a posteriori estimate (MAP estimate) of the recovered signal deduced from mixture measurements. In some embodiments, the algorithm described in FIG. 13 is infeasible for the typical scenario of compressed sensing of a large measurement matrix because the integral in Equation 7 of Example 1 is very high-dimensional in that case. In this example, the small measurement matrices, along with the constraint of 5-10 compounds in any mixture (non-zero elements in each row of the measurement matrix) makes such an approach feasible. In some embodiments, the integral in this example is correspondingly 5-10 dimensional. The algorithm is approximate in the sense of being loopy-BP, but no other approximations are made. In contrast, in existing methods for using such an algorithm for approximate sparse recovery, further approximations (for example, Gaussian distribution of posterior) need to be made to make progress. The problem is, such approximations are incorrect in this construction.

In some embodiments, the method further comprises selecting compound combinations in the first set of compound combinations to reduce overlap between compounds in different compound combinations.

Aspects of the present disclosure further include methods optimizing pharmacological compound development, comprising accessing, for each compound of a plurality of compounds, effect information describing an effect of the compound. In some embodiments, the method includes iteratively training a compound experiment model until a threshold criterion is satisfied by: generating, for each of a plurality of experiments, a corresponding set of compounds to combine together in the experiment using the effect information; performing, for each of the plurality of experiments, the experiment by applying the corresponding set of compounds in a subject; determining, for each of the plurality of experiments, a resulting set of effects of the applied set of compounds within the subject; determining, for each of the plurality of experiments, an association between each effect of the resulting set of effects and a compound of the applied set of compounds to which the effect is attributed; and updating the effect information based on the determined associations between effects and compounds.

In some embodiments, the total number of experiments performed while training the compound experiment model is less than the total number of possible combinations of the plurality of compounds. In some embodiments, the method comprises retraining the trained compound experiment model until the threshold criterion is satisfied, for example, when the accuracy of the recovered signal is within the signal to noise ratio of the measurement noise (instrumental, biological, physiological, physical, biophysical, chemical, biochemical etc. in origin) of the measurement quantifying an effect of a compound. Such threshold criteria include but are not limited to accuracy of learning, within measurement noise, of individual and synergistic/antagonistic parameters.

In some embodiments, the accessed information comprises a qualitative prior configured to estimate a sparsity level and determine the matrix size. In some embodiments, the accessed information comprises in vivo, in vitro, and/or in silico experiments based on pharmacological, medicinal chemistry, biophysics, and synthesis constraints of the plurality of compounds.

In certain embodiments, accessing effect information describing the effect of the compound comprises accessing qualitative and/or quantitative priors. In some embodiments, qualitative priors include any data information constraints about the compounds, such as, but not limited to, its biological activity, pharmacology, pharmacodynamics, toxicity, immunoreactivity, tolerability, synergistic or antagonistic activities, and the like. In some embodiments, the qualitative prior can include known, safe, concentration range constraints of each compound.

In some embodiments, qualitative priors can be used in the present methods to estimate the sparsity level and decide upon the measurement matrix size accordingly (i.e., number of experiments to be done). In some embodiments, the sparsity level is In some embodiments, the qualitative prior is a synergistic or antagonistic activity between the mixture of compounds within the subset of compounds.

In some embodiments, the qualitative prior is an in vivo, ex-vivo, in vitro, and/or in silico prior. In some embodiments, in vivo priors include in vivo data information that were performed on, for example, non-human mammals, mammals, rodents, rats, mice, humans, e.g. rats, mice, pigs, cows, goats, sheep, non-human primates, fish, frogs, vertebrates, and the like. In some embodiments, the in vivo prior includes in vivo data information that were performed in, for example, eukaryotic single-cell organism, a somatic cell, a germ cell, a stem cell, a plant cell, an algal cell, an animal cell, an invertebrate cell, a vertebrate cell, a fish cell, a frog cell, a bird cell, a mammalian cell, a pig cell, a cow cell, a goat cell, a sheep cell, a rodent cell, a rat cell, a mouse cell, a non-human primate cell, or a human cell. In some embodiments, the in vivo prior includes in vivo data information that were performed in cardiomyocytes, neurons, liver cells, pancreatic cells, blood cells, mesenchymal stem cells, skeletal muscle cells, glial cells, spinal cord cells, cardiac cells, skin cells, lung cells, epithelial cells, and combinations thereof.

In some embodiments, the in vitro data information include in vitro data information that were performed in, for example, eukaryotic single-cell organism, a somatic cell, a germ cell, a stem cell, a plant cell, an algal cell, an animal cell, an invertebrate cell, a vertebrate cell, a fish cell, a frog cell, a bird cell, a mammalian cell, a pig cell, a cow cell, a goat cell, a sheep cell, a rodent cell, a rat cell, a mouse cell, a non-human primate cell, or a human cell. In some embodiments, the in vitro data information includes in vitro data information that were performed in cardiomyocytes, neurons, liver cells, pancreatic cells, blood cells, mesenchymal stem cells, skeletal muscle cells, glial cells, spinal cord cells, cardiac cells, skin cells, lung cells, epithelial cells, and combinations thereof. In some embodiments, the in vitro data information includes in vitro data information that were performed in CHO cells, BHL-21, AHL-1, MA-104, Vero, OK, AB9, and combinations thereof.

In some embodiments, the in vitro data information includes in vitro data information that were performed in human cell lines. In some embodiments, human cell lines include, but are not limited to, A431, A549, A172, A2780, A875, BCP-1, BJAB, Caco-2, Cal-27, Calu-3, CML T1, COR-L23, COV-434, DAOY, DU145, DuCaP, EM-2, EM-3, FM3, H1299, HaCaT, HCA2, HEK 293, HEK 2931, HL-60, HL-1080, HT-29, JU, K562, KBM-7, KCL-22, KG1, Ku812, KYO-1, LNCaP, Ma-Mel cell lines, MCF-7, MCF-10A, MDA cell lines, MG63, MIA PaCa-2, MQR/0.2R, Mono-Max-6, MRC-5, NCI cell lines, NALM-1, NK-92, NTERA-2, NW-145, OPCN/OPCT cell lines, PANC-1, PC-3, PNT1A, Raji, SaOS-2, SH-SY5Y, AiHa, SK (Sloan Kettering cancer cell lines), T2, T-47D, T84, T98G, THP U205, U373, U87, U937, VCaP, VG-1, WM39, WT-49, YAR, and combinations thereof.

In some embodiments, the in vitro data information includes in vitro data information that were performed in mouse cell lines. In some embodiments, mouse cell lines include, but are not limited to, 3T3-L1, 4T1, A20, ALC, B16, bEND.13, C2C12, C3H-10T1/2, CGR8, CT26, E14Tg2a, EL4, EMT6 cell lines, GL261, Hepa1c1c7, J558L, L1210, L243, MA2.1, MC-38, MTD-1A, MyEND, Neuro-2a, NIH-3T3, Px63Ag8, RenCa, RIN-5F, RMA-S, YAC-1, and combinations thereof. In some embodiments, the in vitro data information includes in vitro data information that were performed in rat cell lines. In some embodiments, rat cell lines include, but are not limited to, A-10, 9L, B35, C6, PC-12, RBL-1, L2, L6, 516, BRL3A, S16Y, S42, F98, R4-6A2, RL-65, N1-S1, RFL-6, NRK, R2C, MH1C1, CA-77, Rat2, CTX TNA2, RIN-5F, UMR-106, RSC96, XC, RG2, GH4C1, GH3, AR42J, 2.43, RC-4B/C, NBT-II, RLE-6TN, GK1.5, R1-2, D1 TNC1, A7r5, 1D3, PC-12, RIN-m, NR8383, S42, RIN-14B, H9c2, RK3E, and combinations thereof.

In some embodiments, the in vitro data information includes in vitro data information that were performed in primary culture, including but not limited to, primary culture of (for example, rodent or other mammalian model organisms) cortical neurons, hippocampal neurons, striatal neurons, midbrain neurons, hindbrain neurons, dorsal root ganglion neurons, spinal cord neurons etc., iPSC derived differentiated cells, and combinations thereof.

In some embodiments, the in vivo data information include in vivo data information that were performed in, for example, eukaryotic single-cell organism, a somatic cell, a germ cell, a stem cell, a plant cell, an algal cell, an animal cell, an invertebrate cell, a vertebrate cell, a fish cell, a frog cell, a bird cell, a mammalian cell, a pig cell, a cow cell, a goat cell, a sheep cell, a rodent cell, a rat cell, a mouse cell, a non-human primate cell, or a human cell. In some embodiments, the in vivo data information includes in vivo data information that were performed in cardiomyocytes, neurons, liver cells, pancreatic cells, blood cells, mesenchymal stem cells, skeletal muscle cells, glial cells, spinal cord cells, cardiac cells, skin cells, lung cells, epithelial cells, and combinations thereof.

In some embodiments, the effect is a synergistic or antagonistic effect between two or more compounds of the corresponding set of compounds. In some embodiments, the effect information is selected from: biological effect, a chemical effect, a pharmacological effect, and a combination thereof. In some embodiments, the effect is selected from: a biological effect, a chemical effect, and a pharmacological effect, in combination with synergistic or antagonistic effects between compounds of the corresponding set of compounds. In some embodiments, the pharmacological effect is a pharmacodynamic interaction between the compounds within the subset of compounds. In some embodiments, the biophysical effect is a toxicity or an immune response of the subset of compounds. In some embodiments, the biophysical effect is a toxicity or an immune response of each individual compound.

In some embodiments, the trained compound experiment model comprises a matrix.

In some embodiments, the association between the effects is the interaction between each of the plurality of compounds that produce a positive or negative biophysical effect on the safety or efficacy of the combined compounds.

In some embodiments, the interaction is a chemical interaction, a molecular interaction, a toxic interaction, a synergistic or antagonistic interaction, or a combination thereof.

In some embodiments, the subject is an animal. In some embodiments, the subject is a mammal or a rodent. In some embodiments, the subject is a human.

In some embodiments, steps of the method are repeated until a threshold criteria is satisfied by the iteratively updated trained compound experiment model based on one or more desired effects.

A non-limiting example of optimizing compounds for pharmacological development is shown using Algorithm 1 of FIG. 13 in a method of the present disclosure. For example, Algorithm 1 describes that the construction of a measurement matrix can be mapped to a constrained bipartite graph creation problem, with constraints on how the edges are created. On a bipartite graph, an edge can only connect members from distinct node types. In some cases, there are "experiment" nodes (E) and "OBM" nodes (B). An edge connecting node E to node B represents that compound B will be featured in the mixture for the experiment E. A good measurement matrix will sample the compounds equitably, and minimize redundancy in measurement. This implies wanting to create edges such that 1) every compound appears in an identical number of experiments; 2) every experiment has a fixed number of compounds mixed (pharmacological constraint in mixture capacity); and 3) no two compounds both appear in more than one experiment (minimal possible redundancy). Algorithm 1 starts with a random choice of E and B nodes and fills the graph in maintaining the constraint. However, this is suboptimal and depends on initial conditions, and often leads to unsatisfiability for poor initial conditions, hence the need for a deterministic algorithm.

In some embodiments, retraining, refining, or changing the compound matrix model as described herein is performed by a controller. In some embodiments, the controller is a feedback controller. In some embodiments, the feedback controller retrains and/or changes the compound matrix model based on a threshold criterion (e.g., confidence threshold).

In some embodiments, the method comprises calibrating noise in model readout to quantify the level of accuracy achievable in learning factors and stopping criteria of the methods described herein.

In some embodiments, the method comprises predictive models determining the number of experiments to be performed with a mixture of compounds provided into the feedback controller.

III. B. Optimizing Compound Modifications

Aspects of the present disclosure include methods for optimizing modifications of a compound.

In some embodiments, the method includes accessing information describing one or more effects of the compound associated with one or more modifications to the compound. In some embodiments, the method includes determining a minimum number of modifications to the compound required to produce an above-threshold effect and a maximum number of modifications of each modification that can be administered to a subject.

In some embodiments, the method includes training an initial compound modification model based on the accessed information identifying a first set of compound modification combinations, each compound modification combination including a subset of compound modifications, and the number of compound modifications in each subset based on the determined minimum amount and maximum number.

In some embodiments, for each compound modification combination in the first set of compound modification combinations: the method includes accessing a set of effects caused by an application of the subset of compound modifications included in the compound modification combination; and determining an association, for each effect of the subset of effects, between the effect and the compound modification of the subset of compound modifications that caused the effect.

In some embodiments, the method includes retraining the initial compound modification model based on the determined associations between effects and compound modifications; determining a target set of effects; and selecting one or more compound modifications of the plurality of compound modifications for administering to a target subject by applying the retrained compound modification model to the target set of effects. In some embodiments, for example, such a retraining involves refining the initial set of drugs tested in combination to a reduced set of drugs with high synergy or antagonism between some of them, and designing a new measurement matrix which may reduce the total number of drugs tested (the parameter N, see later) in any specific number of combinations (the parameter K, see later) and/or change the number of tests performed (parameter M, see later) to refine the accuracy of the parameters quantifying synergy/antagonism. Additionally, such iterative retraining involves designing a completely new measurement matrix that takes into account an updated estimate of sparsity (parameter p, see later) in synergy/antagonism (meaning, what fraction of all possible pairwise synergy/antagonism is non-zero for the reduced set of drugs) analyzing the measurements of the last iteration, and results in an updated estimates of the parameters quantifying synergy/antagonism after the new set of testings are conducted.

In certain embodiments, retraining comprises repeating the steps of the method until a threshold criterion is reached.

In some embodiments, the application of the subset of compound modifications comprises in vitro experiments, in vivo experiments, in-silico experiments, or a combination thereof.

In some embodiments, the one or more modifications comprises chemical modifications. In some embodiments, the chemical modifications allow for the compound to attach to a moiety. In some embodiments, chemical modifications include, but are not limited to protein covalent modifications, residue-specific modifications, specific modification of N and C termini, organometallic catalysis-based covalent modifications, photochemically induced bioconjugations, protein crosslinking, and combinations thereof. In some embodiments, the one or more modifications comprises sequence-specific modifications. In some embodiments, sequence specific modifications include, but are not limited to, one or multiple, position-dependent or position independent, presence of kmers (q-grams) in the original sequence, and combinations thereof. In certain embodiments, the sequence-specific modifications comprise an amino acid substitution and/or a nucleotide substitution. In certain embodiments, the sequence-specific modifications are amino acid modifications. In certain embodiments, the amino acid modification is a substitution or mutation. In some embodiments, sequence-specific modifications are nucleotide modifications. In certain embodiments, the nucleotide modification is a substitution. Non-limiting examples of nucleic acid modifications include three broad categories: backbone/linkage modifications, sugar modifications, and nucleobase-modifications. Non-limiting examples of backbone/linkage modifications include, but are not limited to phosphorothioate, phosphorodithioate, methylphosphonate, methoxy propyl phosphonate (MOP), mesyl phosphoramidate ($\mu$), phosphoramidate, morpholino, peptide nucleic acid, amino-alkylated phosphoramidates, guanidine-linked, methylthio-urea linked, nucleosyl amino-acid-modified, phosphotriester, boranophosphate, formacetal, thioformacetal, methylene-(methylimino) (MMI), C3-amide, methylene phosphonate, and combinations thereof. Non-limiting examples of sugar modifications include, but are not limited to 2'-O-Methyl (2'-OMe), 2'-O-Methoxyethyl (MOE), 2'F-RNA (FRNA), 4'-thio, LNA, cEt (2'-4'-constrained ethyl), cMOE (2',4' constrained MOE), 2-thio LNA, 2-amino LNA, seLNA, cProp-BNA, 5'-Me-LNA, Oxyamino-BNA, aminooxy-BNA, methoxy-aminoLNA, GuNA, AmNA, suNA, Urea-BNA, HxNA, carba-ENA, carba-LNA, Me cLNA, Fluro cLNA, methylene cLNA, ENA, PrNA, DpNA, BNA COC, ethyleneoxy BNA, Disulfide BNA, AmNA, GuNA, scpBNA, c-ANA, bsNA, LceNA and other Bridged nucleic acid (BNA) analogies, α-L-LNA and analogues, α-β constrained nucleic acid (CNA) analogues, dual constrained nucleic acids and analogues, HNA, tcDNA, and combinations thereof. Non-limiting examples of nucleobase modifications and analogues include, but are not limited to 5-Methyl pyrimidines, 5-substituted pyrimidine analogies, 2-Thio-thimine, Purine modifications, universal bases, abasic sites, degenerate bases, and combinations thereof.

In some embodiments, the effect is of each individual modification on the compound. In some embodiments, the effect is between the modifications within the compounds. In some embodiments, the effect is selected from: a biophysical effect, a synergistic or antagonistic effect, and a combination thereof.

In some embodiments, the pharmacological effect is a pharmacodynamic interaction between compound modification combinations.

In some embodiments, the biophysical effect is a toxicity or an immune response between compound modification combinations. In some embodiments, the biophysical effect is a toxicity or an immune response of each individual modification of the compound.

In some embodiments, the effect is affinity maturation of the compound. In some embodiments, the effect is a stability of the compound. In some embodiments, the effect is a conjugation reaction of the compound to a moiety.

In some embodiments, the one or more modifications comprises 2 or more modifications, 3 or more modifications, 4 or more modifications, or 5 or more modifications. In some embodiments, the one or more modifications comprises 5 or more modifications, 6 or more modifications, 7 or more modifications, 8 or more modifications, 9 or more modifications, or 10 or more modifications. In some embodiments, the one or more modifications comprises 10 or more modifications, 12 or more modifications, 16 or more modifications, 18 or more modifications, 20 or more modifications, 24 or more modifications, 26 or more modifications, 28 or more modifications, 30 or more modifications, 32 or more modifications, 34 or more modifications, 36 or more modifications, 38 or more modifications, 40 or more modifications, 42 or more modifications, 44 or more modifications, 46 or more modifications, 48 or more modifications, or 50 or more modifications.

In some embodiments, the effect is a synergistic or antagonistic effect between compound modification combinations.

In some embodiments, the synergistic or antagonistic effect between sequence-specific modifications is calculated by explicitly coding the interaction term in the measurement paradigm. For example, taking an outer product of the binary vector of each experiment (a row of the measurement matrix) to create an (upper triangular) matrix. In some embodiments, a diagonal element of the matrix is the independent contribution. In some embodiments, off diagonals are pairwise contributions. In some embodiments, the method includes unravelling this matrix to create a vector, and concatenating these vectors row wise to create a new "measurement matrix", which is sparse and binary, and which acts upon the vector space of the parameters quantifying individual and pairwise contributions (the diagonal elements are individual and the off-diagonal elements are pairwise). In some embodiments, the "signal" is simply the other product in the same manner, it is assumed sparse for only the off diagonals. In some embodiments, the recovery is a standard l1-sparsity algorithm.

In some embodiments, the synergistic or antagonistic effects of between two or more modifications in the compound are sparse. In some embodiments, the individual effect of the compound is not sparse. In some embodiments, the method includes a l1-sparsity convex optimization approach. The l1-sparsity convex optimization approach is a class of algorithms well known to a practitioner of the art of convex optimization. It uses a l1 (the sum of magnitude of parameters) regularizer for a (possibly under-determined) cost function, solved using convex optimization, for example, a least square fit of linear response (measured) to an signal (unknown, where the response is modelled as a linear transformation of the signal with a known measurement matrix). The l1-sparsity regularizer has been shown to result in sparse signal recovery, meaning, several components of the signal are exactly zero. Several well-known methods and software packages (CVXOPT, MOSEK, Gurobi etc.) can solve such a convex optimization problem.

In some embodiments, the compound modification model comprises a matrix. In some embodiments, the matrix is based on the accessed information, each column of the matrix corresponding to a compound modification that can be included in the first set of compound modification combinations, and each row of the matrix corresponding to an experiment associated with the first set of compound modification combinations.

In some embodiments, the subject is an animal. In some embodiments, the subject is a mammal or a rodent. In some embodiments, the subject is a human.

A non-limiting example describing a compound modification optimization method of the present disclosure is shown as Algorithm 2 of FIG. 14 and Example 2.

Aspects of the present disclosure include methods for optimizing chemical modification of compounds, wherein two or more independent chemical modifications are simultaneously tested in the same physical system and the independent contributions for each independent chemical modification are deconvolved, said method comprising the steps of: providing a reference prior that is approximately sparse; calibrating the readout to the reference to determine the range of min to max dosing and mixing number for each compound and chemical modification; generating a custom measurement matrix specification using the parameters determined in step (b) and loading the generated positive measurement matrix into a computing device; physically combining the compounds in the proportions determined in step (c); determining measurements of each mixture experiment as determined in step (c); reconstructing individual measurements from the mixture experiment; and applying one or more transformations to the measurement matrix, including optimization and deterministic extension of said matrix, based on the determined measurements of step (e) and repeating steps (d)-(f) until individual measurements are reconstructed for each compound in the mixture. In some embodiments wherein, where the total number of experiments are fewer than the total number of compounds combined, or fewer than the number of total parameters to be learned.

III. C. Designing Treatments for a Disease or Condition

Aspects of the present disclosure include methods for designing treatments for a disease or condition.

In some embodiments, the method includes accessing, for each of a plurality of therapies, information describing an effect of the therapy on a subject.

In some embodiments, the method includes determining a number of therapies that can be combined such that the combination is safe to apply and such that an effect of each therapy in the combination can be detected when applied.

In some embodiments, the method includes generating a matrix based on the accessed information, each column of the matrix corresponding to a therapy of the plurality of therapies and each row of the matrix corresponding to an experiment associated with a set of the therapies.

In some embodiments, for each experiment, the method includes determining a set of effects caused by an application of the set of therapies associated with the experiment and determining which therapy in the set of therapies corresponds to each effect in the set of effects.

In some embodiments, the method includes modifying the matrix by additional rows corresponding to additional experiments, each associated with a different set of the therapies.

In some embodiments, the method includes treating the disease with a set of therapies selected using the modified matrix.

In some embodiments, the effect is of each individual therapy. In some embodiments, the effect is between the therapies within the set of therapies.

In some embodiments, the effect is selected from: a biophysical effect, a synergistic or antagonistic effect, and a combination thereof. In certain embodiments, biophysical effect is a biological effect, a chemical effect, or a pharmacological effect. In certain embodiments, the pharmacological effect is a pharmacokinetics and pharmacodynamic interaction between the set of therapies. In certain embodiments, the biophysical effect is a toxicity or an immune response of the set of therapies. In some embodiments, the biophysical effect is a toxicity or an immune response of each individual therapy.

In some embodiments, the effect is the synergistic or antagonistic effect between the set of therapies. In some embodiments, the effect is a side effect of each individual therapy. In some embodiments, the effect is a side effect caused by the combination of therapies within the set of therapies.

In some embodiments, the set of therapies comprises two or more therapies, three or more therapies, four or more therapies, or five or more therapies.

In some embodiments, the combination of therapies includes, but is not limited to photodynamic therapy, gene therapy, oxygen supply, physical therapy, surgical procedures, radiation and chemotherapy, hormone treatments, and combinations thereof. In some embodiments, the combination of therapies is selected from the group consisting of photodynamic therapy, gene therapy, oxygen supply, physical therapy, surgical procedures, radiation and chemotherapy, and hormone treatments. In some embodiments, the combination of therapies is a treatment for a genetic, chronic or acute condition. In some embodiments combination of treatment comprises drug treatments (for example, a small-molecule, antibody, peptide, nucleic-acid drug etc.) in combination with biologics, a medical procedure or other medical interventions. In some embodiments, medical interventions include, but are not limited to vaccination, blood transfusion, gene therapy, oxygen supply, physical therapy, surgical procedures, radiation and chemotherapy, hormone treatments, and combinations thereof. In some embodiments, the chronic condition is selected from group consisting of Alzheimer's disease, Parkinson's disease, Dementia, Arthritis, Asthma, Cancer, Chronic obstructive pulmonary disease (COPD), Crohn's disease, cystic fibrosis, Diabetes, Epilepsy, heart disease, Multiple Sclerosis, and human immunodeficiency virus (HIV). In certain embodiments, the oxygen supplied to the subject is from a ventilator.

In some embodiments, the virus is an influenza virus selected from the group consisting of: parainfluenza virus 1, parainfluenza virus 2, influenza A virus, and influenza B virus. In some embodiments, the virus is a coronavirus. In some embodiments, the coronavirus is selected from the group consisting of: coronavirus OC43, coronavirus 229E, coronavirus NL63, coronavirus HKU1, middle east respiratory syndrome beta coronavirus (MERS-CoV), severe acute respiratory syndrome beta coronavirus (SARS-CoV), and SARS-CoV-2. In some embodiments, the coronavirus is SARSCoV-2.

III. D. Computer-Implemented Methods

Aspects of the present disclosure include computer-implemented methods for training a model for pharmacological compound design. In some embodiments, the method includes accessing a first set of data comprising physiological or pharmacological characteristics of each of a set of compounds from one or more databases.

In some embodiments, the method includes generating a first training set of data based on the accessed first set of data describing, for each compound of the set of compounds, a toxicity and an efficacy of the compound.

In some embodiments, the method includes training a machine-learned model in a first stage using the first training set of data.

In some embodiments, the method includes accessing a second training set of data describing an updated toxicity and updated efficacy of each compound in a set of compounds. In some embodiments, the method includes training the machine-learned model in a second stage using the second training set of data.

In some embodiments, the machine-learned model comprises one of: an Ising model, a Potts model, a hidden Markov model, a continuous random field model, and a directed acyclic graphical model.

In some embodiments, the machine-learned model is selected from one or more of: a stochastic model, a model algorithm, an ML model, a Bayesian model, and a message passing model.

In some embodiments, the machine-learned model comprises one of: a random forest classifier, a logistic regression, a linear regression, a neural network, a sparsity-driven convex optimization fit, and a support vector machine.

Aspects of the present disclosure include a computer-implemented method of training a model for pharmacological compound design.

In some embodiments, the method includes generating a first training set of data comprising, for each of a first set of compounds, information describing a composition of the compound, a toxicity of the compound, and a biophysical effect of the compound.

In some embodiments, the method includes training a machine-learned model using the first training set of data, the machine-learned model configured to map a composition of a compound to a toxicity and biophysical effects of the compound.

In some embodiments, the method includes generating a second training set of data describing an updated toxicity and updated biophysical effects of each compound in a second set of compounds, the second set of compounds selected using the machine-learned model. In some embodiments, the method includes retraining the machine-learned model using the second training set of data.

In some embodiments, the machine-learned model comprises one of: an Ising model, a Potts model, a hidden Markov model, a continuous random field model, and a directed acyclic graphical model.

In some embodiments, the machine-learned model is selected from one or more of: a stochastic model, a model algorithm, an ML model, a Bayesian model, and a message passing model.

In some embodiments, the machine-learned model comprises one of: a random forest classifier, a logistic regression, a linear regression, a neural network, a sparsity-driven convex optimization fit, and a support vector machine.

Aspects of the present disclosure include a computer-implemented method for optimizing chemical modification of pharmacological compounds.

In some embodiments, the method includes collecting data associated with one or more modifications to one or more pharmacological compounds and describing a resulting toxicity or effect of the modifications.

In some embodiments, the method includes comparing a resulting toxicity or effect of the modification to a predefined threshold. In some embodiments, a predefined threshold may be an in vitro or/and in vivo safety criteria of measurements of cytotoxicity, membrane toxicity, immunotoxicity, mitotoxicity, and combinations thereof.

In some embodiments, the method includes generating a model using the collected data, the model including combinations of 1) the pharmacological compounds, and 2) a set of pharmacological compounds modified by the one or more chemical modifications.

In some embodiments, the method includes collecting additional data associated with a toxicity or effect of the combinations included in the model when the resulting toxicity or effect of the chemical modification exceeds the predefined threshold.

Aspects of the present disclosure include a computer-implemented method of training a model for optimization of chemical modification of oligo-based medicines (OBMs) comprising: collecting a set of physiological or pharmacology observations recorded in a experiment or medical record in a database; applying one or more transformations to each digital OBM toxicity record including normalization and pre-processing to create a modified set of digital OBM toxicity records; creating a first training set comprising the collected set of digital OBM toxicity records, the modified set of digital OBM toxicity records, and a third set of digital OBM toxicity records; training the model in a first stage using the first training set; creating a second training set for a second stage of training comprising the first training set and digital non-toxic OBMs that are incorrectly detected as toxic after the first stage of training; and training the model in a second stage using the second training set.

Aspects of the present disclosure include a computer-implemented method of training a model for optimization of chemical modification of oligo-based medicines (OBMs) comprising: collecting a set of physiological or pharmacology records from a database; applying one or more transformations to each record including normalization and pre-processing to create a modified set of physiological or pharmacology records; creating a first training set comprising the collected set of physiological or pharmacology records, the modified set of physiological or pharmacology records, and a third set of non-physiological or non-pharmacology records; training the model in a first stage using the first training set; creating a second training set for a second stage of training comprising the first training set and non-physiological or non-pharmacology that are incorrectly detected as having one or more of a physiological or pharmacological effect after the first stage of training; and training the model in a second stage using the second training set.

Aspects of the present disclosure include a computer-implemented method for optimizing chemical modification of oligonucleotide-based medicines (OBMs) comprising: collecting, by a computing device, OBM data related to one or more chemical modifications, the data comprising at least one of toxicity, nucleotide position of chemical moiety, and OBM sequence; comparing, by a computing device, at least one of the collected data to a predefined threshold; and generating a custom measurement matrix specification using the parameters determined in steps (a) and (b) and loading the generated positive measurement matrix into a computing device; and collecting additional OBM data relating to efficacy or toxicity when the collected data is greater than the predefined threshold, the additional data comprising combinatorial mixing data as specified by the measurement matrix specification.

IV. EXAMPLES

IV. A. Example 1—Compressed Sensing: Setup

For the sake of clarity, the methods described herein are now described in the context of a particular example. It should be noted, however, that the subject matter described herein is applicable far more broadly. The methods described in the particular examples can be applied to any drug combinations, including OBMs as a non-limiting example.

This example is constructed to provide an example of algorithmic methods to reduce the burden of in vivo screening, without compromising the quality of data and the granularity and certainty with which the pharmacology is learned.

A central concept in compressed sensing is that for a sparse signal x of dimension N, where sparsity implies that only elements of x are non-zero, x can be measured/sensed with M<<N linear measurements to obtain measured values y=Φx, and still recover the signal x exactly. In the usual description of the problem, the sparsity fraction is defined as ρ=K/N and the under-sampling fraction as α=M/N. For given ρ, there is a critical $α_c$ which is a function of ρ, such that if $α(ρ)>α_c(ρ)$ exact recovery is possible using l1-sparsity. The transition line $α_c(ρ)$ is called the Donoho-Tanner phase transition line. The recovery problem has a first order phase transition at this line. The l1-sparsity solution is a convex optimization method minimizing the function, $$\min_x \|y - \Phi x\|^2 + \lambda |x| \quad (1)$$

where λ is the sparsity parameter. The solution recovery does not depend strongly on k, as long as λ is positive.

In this example, a Bayesian approach is of interest to the problem because the typical signals we will be dealing with are not exactly, but only approximately, sparse. But before presenting the Bayesian approach, the signal transformations first need to be defined for which we expect the transformed signal to be approximately sparse. See. FIG. 1B as an illustration of the linear regime is a (transformed) scale of dose.

2.1 Sparse Signal Space

Non-limiting examples of scenarios that may be encountered with, in this example, OBM pharmacology, for which the transformed signal space is sparse are:

(1) Dose-response data is gathered for, for example, cytotoxicity in a number of cell lines, all for individual OBMs. Dose-response data is gathered, for, for example, liver toxicity in rodents for the same OBMs. The correspondence of in vitro to in vivo pharmacology was then mapped as a (noisy) fit, $\gamma=f(X)+\in$, where E captures random noise level. Here X is the (vector) of scaled in vitro measurements, for example, Caspase activation etc., and y is the corresponding scaled in vivo measurement, say, Alanine aminotransferase (ALT) level in rodents on suitable allometric dose scaling. In general, $\gamma=f(X| d_{in\ vitro}, d_{in\ vivo})+\in$, where d is dose.

The expectation when a large batch of OBMs is dosed individually in animals (making sure all of the OBMs are above the minimum dose within the log-linear regime of calibrated dose response for ALT) is that a sizeable proportion of OBMs will follow the in vitro to in vivo mapping we calibrated, i.e., f(X). In this context, the sparse signal transformation is $\hat{\gamma}$–f(X), where $\hat{\gamma}$ is the observed in vivo response. The expectation is that, $\hat{\gamma}$–f(X) is close to zero (noise level of fit) more often than a large deviation (when liver toxicity measurement for the OBM does not agree at all with cytotoxicity assays in cell lines).

Data was gathered on a set of sequences for a class of chemical modifications, for example, 3-10-3 LNAs, 2-10-4 LNAs, 3-10-3 cEts, 4-10-2 cEts etc. This allowed for mapping the impact on chemistry, for example, activity, for those sequence contexts. Next, the impact on chemistry was explored for a broader class of sequences. The data was used to create a map from sequence and chemistry to activity, $\gamma=f(s,c)+\in$, where E is again noise level, and s, c are sequence and chemistry respectively. Again, the expected measurements on new sets of sequences to be sparse in deviation from expectation, i.e., $\gamma$–f(s,c) is approximately sparse.

Predictive models were built for an association of compound to biophysical effects, but wanted to refine these models with more data. The deviation from model prediction is therefore sparse—the sparsity is in the space of prediction error.

These examples motivate the following approximately sparse definition of signal, which is a vector of individual responses of N OBMs, denoted by x as $$P(x) = \prod_{i=1}^{N} [\rho\psi(x_i) + (1-\rho)N(0,\sigma)] \quad (2)$$

Here, the vector of signal was modeled as independent and identically distributed, drawn from a mixture of approximately sparse components. The parameter p defined before is the sparsity fraction, $N(0, \sigma)$ is a Gaussian distribution with zero mean and small standard deviation a capturing the noise (approximate sparsity) and $\psi(x_i)$ is an arbitrary distribution of sparse components with values typically large compared to noise level σ.

2.1 Sparse Learning as a Bayesian Problem

M measurements were made of the N components signal x using linear projection of measurements. The linear projection was written as $$y_\mu = \sum_{j}^{N} \Phi_{\mu j} x_j \quad (3)$$

where Φ in an M×N measurement matrix. The peculiarities of the measurement matrix is discussed later. The goal of compressed sensing was to recover the best estimate of x given y. The Bayes optimal way to estimate true signal from y was to compute the mean over the posterior distribution of x given y and Φ, see [2]. In other words, the best estimate was $$x_j^* = \int dx_j x_j p(\Phi, y) \quad (4)$$

$$p(\Phi, y) := \int_{k \neq j} P(y, \Phi) \prod_{k \neq j} dx_k \quad (5)$$

where p(φ, γ) is the marginal posterior probability over $x_j$ given y and Φ. The posterior distribution P(γ, Φ) is given by, $$P(y, \Phi) = \frac{1}{Z(y, \Phi)} P(x) \prod_{\mu=1}^{M} \delta\left(y_\mu - \sum_{j=1}^{N} \Phi_{\mu j} x_j\right) \quad (6)$$

where P(x) is given by Eq. 2, δ is the Dirac Delta function, and Z (y, Φ) is the normalization to ensure that probabilities sum to unity. It was mathematically easier, and also of practical interest, to introduce noise in the measurement y, with variance Δ, i.e., $\gamma_i = \Sigma_j^N \Phi_{ij} x_j + \in$, where $\in$ is Gaussian noise. Then the δ-function was replaced by a Gaussian term and we obtained, $$P(y, \Phi) = \frac{1}{Z(y, \Phi)} P(x) \prod_{\mu=1}^{M} \frac{1}{\sqrt{2\pi\Delta}} \exp\left[-\frac{\left(y_\mu - \sum_{j}^{N} \Phi_{\mu j} x_j\right)^2}{2\Delta}\right] \quad (7)$$

$$= \frac{1}{Z(y, \Phi)} \prod_{i=1}^{N} [\rho\psi(x_i) + (1-\rho)N(0,\sigma)] \quad (8)$$

$$\prod_{\mu=1}^{M} \frac{1}{\sqrt{2\pi\Delta}} \exp\left[-\frac{\left(y_\mu - \sum_{j}^{N} \Phi_{\mu j} x_j\right)^2}{2\Delta}\right]$$

In order to ease the notation, the following rules were followed. Greek subscripts like μ, γ were used for the smaller dimension, $\mu, \gamma \in [1, M]$. The Latin subscripts like j, k were used for the larger dimension j, $k \in [1, N]$. The marginal p(φ, γ) was computed. This was done using approximate belief propagation (message passing).

In the general case, if $P(x) = 1/z\Pi_{\alpha=1}^{Q} \psi_\alpha(x_\alpha)$ where $\psi_\alpha$ are the Q factors, and $x_\alpha$ is the subset of all variables $x_j$ the factor depends on. In that case, the marginal $p(x_j)$ of $P(x)$ was computed by iterative updating these pair of messages, $$M_{b \to i}(x_i) = \sum_{x_{b \setminus i}} \Psi_b(x_b) \prod_{j \in b \setminus i} M_{j \to b}(x_j) \quad (9)$$

$$M_{i \to b}(x_i) = \prod_{b \in i \setminus a} M_{b \to i}(x_i) \quad (10)$$

where $x_{b \setminus i}$ implies "all $x_i$ variables in set b except i" etc. Message passing was exact on tree graphs and chains, but was approximate on graphs with loops. The iterations were paused once the messages saturated, and $P(x_i) \propto \Pi_{\alpha \in i} M_{\alpha \to i}(x_i)$. The proportionality, as opposed to equality, was because there was a need to normalize the probabilities.

In this case, message passing was approximate because the $P(\gamma, \Phi)$ has factors, but the factors are dependent on a sparse subset of variables, and not disjoint subsets. However, message passing worked remarkably well in practice, for reasons discussed later. The messages were, $$M_{\mu \to j}(x_j) = \frac{1}{Z_{\mu \to j}} \int \prod_{k \neq j} dx_k \, \exp\left[-\frac{\left(y_\mu - \sum_{k \neq j}^N \Phi_{\mu k} x_k - \Phi_{\mu j} x_j\right)^2}{2\Delta}\right] M_{k \to \mu}(x_k) \quad (11)$$

$$M_{j \to \mu}(x_j) = \frac{1}{Z_{j \to \mu}} [\rho \psi(x_j) + (1-\rho)N(x_j \mid 0, \sigma)] \prod_{\gamma \neq \mu} M_{\gamma \to j}(x_j) \quad (12)$$

The present inventors took advantage of the sparsity of the measurement matrix $\Phi_{\mu j}$, which was unique to this case. The measurement matrix was binary (discussed later) and had a (typically fixed) small number K entries in every row of $\Phi_{\mu j}$ to be nonzero. Also, any pair of columns had at most one row position where both columns had non-zero entry. This was then used in the message passing algorithm without any further approximations, contrary to the approximations needed when $\Phi$ is dense.

Figure 3:
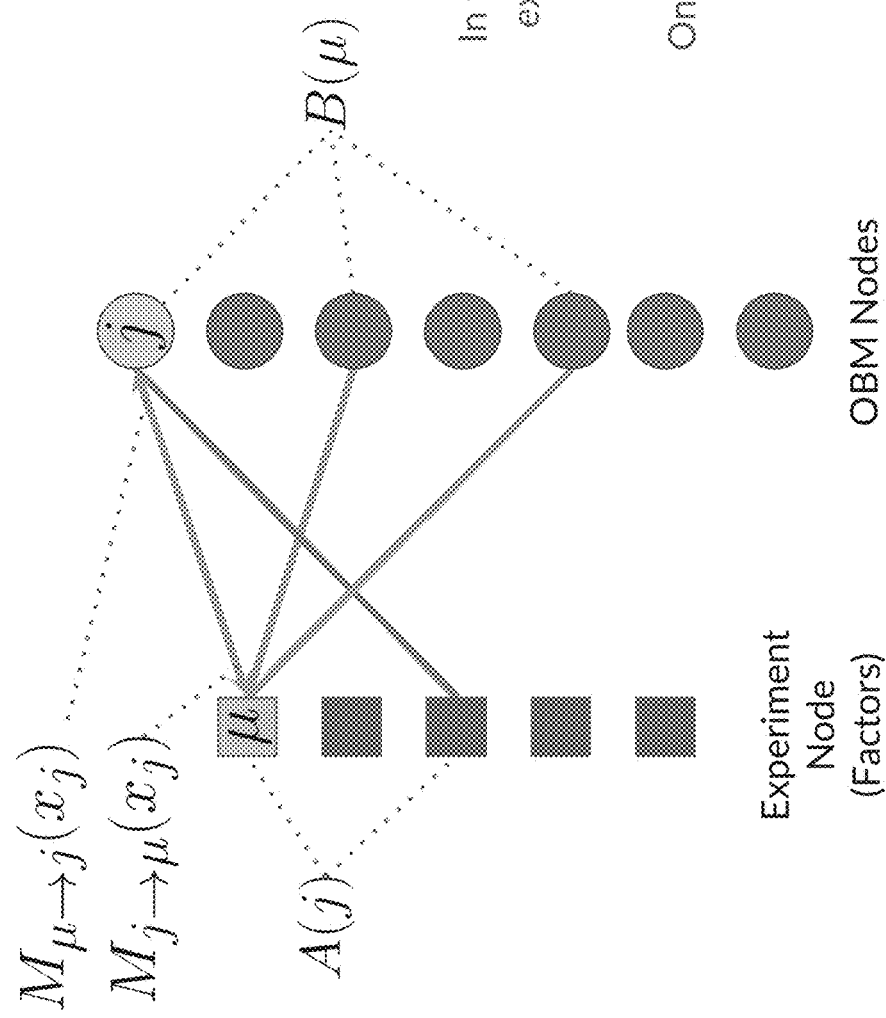
FIG. 3 is an exemplary depiction of a Factor graph corresponding to the message passing (belief propagation) algorithm. An edge exists between an experiment node and an OBM node if the OBM appears in the experiment. The experiment nodes become factors in this factor graph because the probability distribution function over the OBM response $(x_j)$ is joined over the OBMs that appear in an experiment. $B(\mu)$ is the set of all OBM nodes j present in the experiment (connected to the experiment node) $\mu$. Similarly, $A(j)$ denotes all the experiment nodes sharing the OBM node j.

The factor graph corresponding to the message passing is shown in FIG. 3. The iterative steps, denoted by the time index t, of the message passing algorithm whereas follows:

1. Initialization: $M_{j \to \mu}(x_j | t=0) = P(x_j)$, where $P(x_j | t=0)$ is simply the prior given by Eq. 2. It is useful to denote the pdf of $x_j$ at every iterative step t as, $P(x_j | t)$. Therefore, $$P(x) = \prod_{i=1}^N [\rho \psi(x_i) + (1-\rho)N(0, \sigma)]$$

2. Consider all OBMs j that appear in an experiment $\mu$ and call it the set B ($\mu$), see FIG. 3. For each j denote the random variable:

$$z_{\mu \to j} = \sum_{k \in B(\mu) \neq j} \Phi_{\mu k} x_k$$

i.e., the mixture of OBMs in the experiment $\mu$ except the OBM node j under consideration. Denote the pdf of $z_{\mu \to j}$ as $P(z_{\mu \to j} | t)$. Notice that, $$M_{\mu \to j}(x_j | t) = \frac{1}{Z_{\mu \to j}} \int dz_{\mu \to j} \, \exp\left[-\frac{(y_\mu - z_{\mu \to j} - \Phi_{\mu j} x_j)^2}{2\Delta}\right] P(z_{\mu \to j} | t) \quad (13)$$

The computation of $P(z_{\mu \to j} | t)$ is a K—1 dimensional numerical integration problem, where K is the number of OBMs we are mixing in an experiment, $$P(z_{\mu \to j} | t) = \int \prod_{k \in B(\mu) \neq j} dx_k P(x_k | t) \delta\left(z - \sum_{k \in B(\mu) \neq j} \Phi_{\mu k} x_k\right) \quad (14)$$

3. Now $M_{j \to \mu}(x_j | t)$ is ready to be computed. Denote by A(j) the set of experiment nodes that the OBM mode j is connected to. Then, $$M_{j \to \mu}(x_j | t) = \frac{1}{Z_{j \to \mu}} [\rho \psi(x_j) + (1-\rho)N(x_j | 0, \sigma)] \prod_{\gamma \in A(j) \neq \mu} M_{\gamma \to j}(x_j) \quad (15)$$

4. Compute (update) $P(x_j | t)$, $$P(x_j | t) = \frac{1}{Z_j} [\rho \psi(x_j) + (1-\rho)N(x_j | 0, \sigma)] \prod_{\gamma \in A(j)} M_{\gamma \to j}(x_j) \quad (16)$$

1. In some embodiments, a fine grid was used and approximate pdfs as pmfs.

$$z_{\mu \to j} = \sum_{k \in B(\mu) \neq j} \Phi_{\mu k} x_k$$

3. In some embodiments, the computation of $M_{\mu \to j}(x_j | t)$ reduced to a two-dimensional numerical integration on a grid, and was the most computationally intensive step in the algorithm, but not a bottleneck.

Section 3 in the Examples describes in detail how the Bayesian approach compared to l1-sparsity recovery.

2.3 the Measurement Matrix

In this section the constraints that were imposed on the measurement matrix $\Phi$ are discussed. These constraints were unique to the problem. Recall that the rows of $\Phi$, corresponding to each experiment, are fractions of total dose D that were mixed in that experiment. In this case, this matrix itself is sparse, as is explained below.

Only up to a certain maximum number of drug combinations (e.g., OBMs) can be mixed, see FIG. 1B. This is because (transformed) response is approximately linear only over a range of (say, logarithm) dose, a lower and upper threshold of dose we denote by $[d_<, d_>]$ Sensing is needed within this dose range, otherwise there is either severe overdosing or under-dosing the OBMs. Calibrating the dose response is needed for the pharmacology that is being studied using individual OBM experiments before performing any mixture experiments.

To simplify the compressed sensing problem, all OBMs were mixed in equal dose, which leads to a binary $\Phi$ matrix, $\Phi_{\mu j} \in \{0, 1\}$. However, the dose range of sensitivity $[d_<, d_>]$ limits the maximum number of non-zero values in rows of $\Phi_{\mu j}$: maximum number of OBMs that can be studied in a mixture is $[d_>/d_<]$. For compressed sensing, the measurement matrix should also obey the Restricted Isometric Property (RIP), otherwise the measurements are mutually coherent and poorly powered to sense the original signal in a linear subspace. A RIP achieves guarantees for recovery of sparse signal. This property dictates that the eigenvalues of $\Phi_S^T \Phi_S$ are all within $[1-\eta, 1+\eta]$, where $\eta$ is a small number, for all sub-matrix $\Phi_S$ of $\Phi$ of size M×S where $1 \leq S \leq N$. RIP essentially requires that every set of columns with cardinality less than or equal to N behaves like an orthonormal system. RIP is a sufficient condition, but NP-hard to guarantee for a deterministic matrix construction.

A more accessible criteria for robust sparse recovery is the minimal mutual coherence. Mutual coherence C (Φ) is defined as, $$C(\Phi) = \max_{1 \leq i,j \leq N} \frac{|\langle \phi_i, \phi_j \rangle|}{\|\phi_i\|\|\phi_j\|}$$

where φ is the i-th column of matrix Φ. In other words, C (Φ) is the absolute inner product between different normalized columns of Φ. The criteria allows for determining the minimum coherence one can achieve.

For example, a mutual coherence in a non-limiting example of the present application can be 1/square root (number of compounds mixed) because we are working with a positive definite matrix. It has been shown that mutual coherence is equivalent to RIP criteria to guarantee efficient recovery of sparse signals.

The Welch bound dictates that:

$$C(\Phi) \geq \sqrt{\frac{N-M}{M(N-1)}} = \sqrt{\frac{1-\rho}{\rho(N-1)}}$$

where in the last equality we have used the definition of sparsity fraction, ρ=M/N. It is also known that exact recovery is possible using C-coherent matrices, as long as the number of sparse elements K in the signal follows:

$$K < \frac{1}{2}\left(1 + \frac{1}{C}\right)$$

If coherence is small, signals were recovered with lower sparsity. In the lower limit of the Welch bound, the best case scenario was obtained. For large N the Welch bound $$C(\phi) \gtrsim \frac{1}{\sqrt{M}}$$

results in, K<½(1+√M), which implies that for large N, signals of sparsity K were recovered with at least M measurements dictated by the above equation, if measurement matrices were constructed with close to lowest possible coherence.

2.4 Generalizing Construction to Stochastic Methods: Insight from Graph Theory

Figure 4:
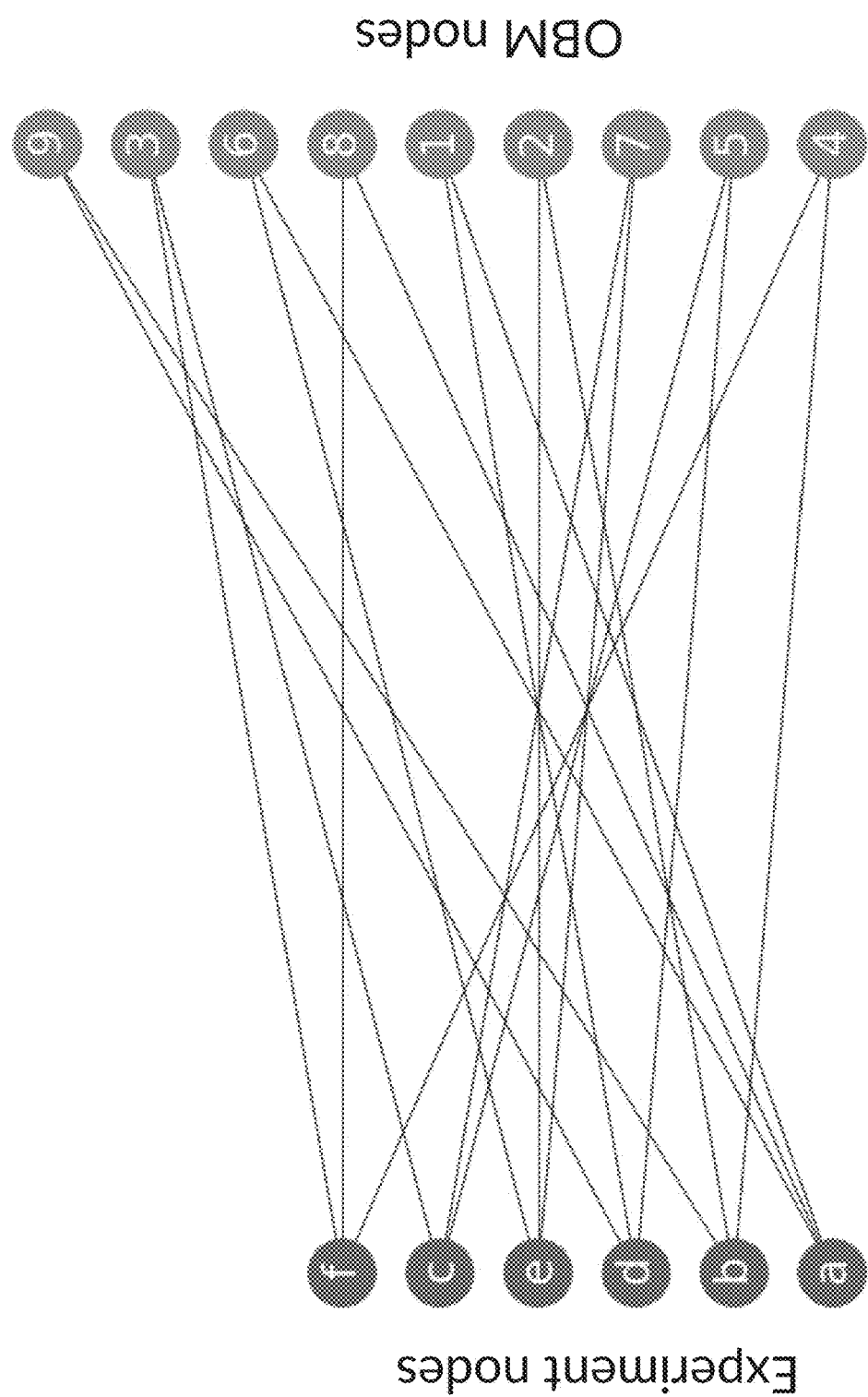
FIG. 4 depicts a non-limiting example of the measurement matrix mapped to a graph. The measurement matrix is treated as the adjacency matrix of a bipartite graph connecting experiment nodes to OBM notes.
Figure 6A:
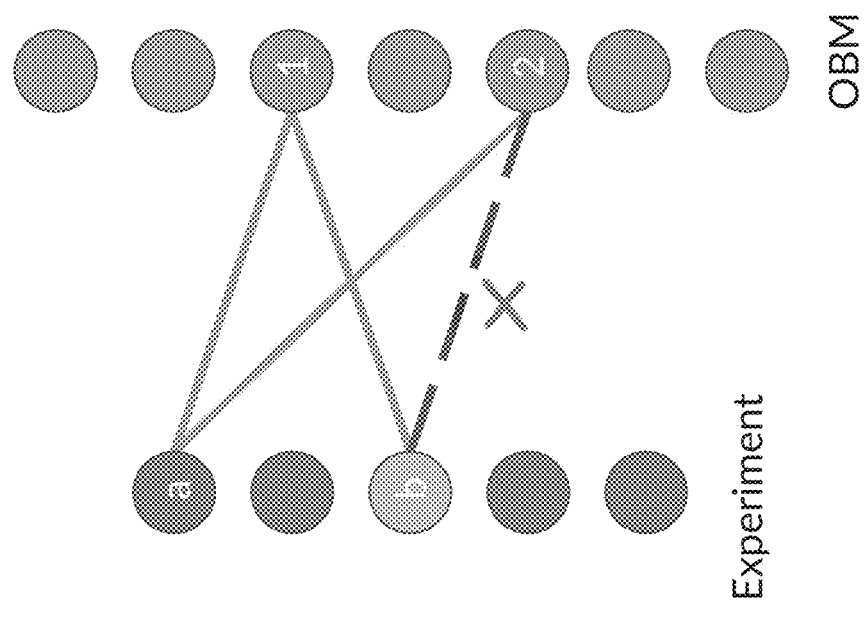
FIG. 6A The rows and the columns of the measurement matrix 1 are constrained. If an experiment (row a) uses two OBMs (columns OBM1 and OBM2) present in the mixture, then another experiment (another row b) cannot share the same set of OBMs. If it did, then the overlap would be greater than 1 and lead to suboptimal measurement matrix.
Figure 6B:
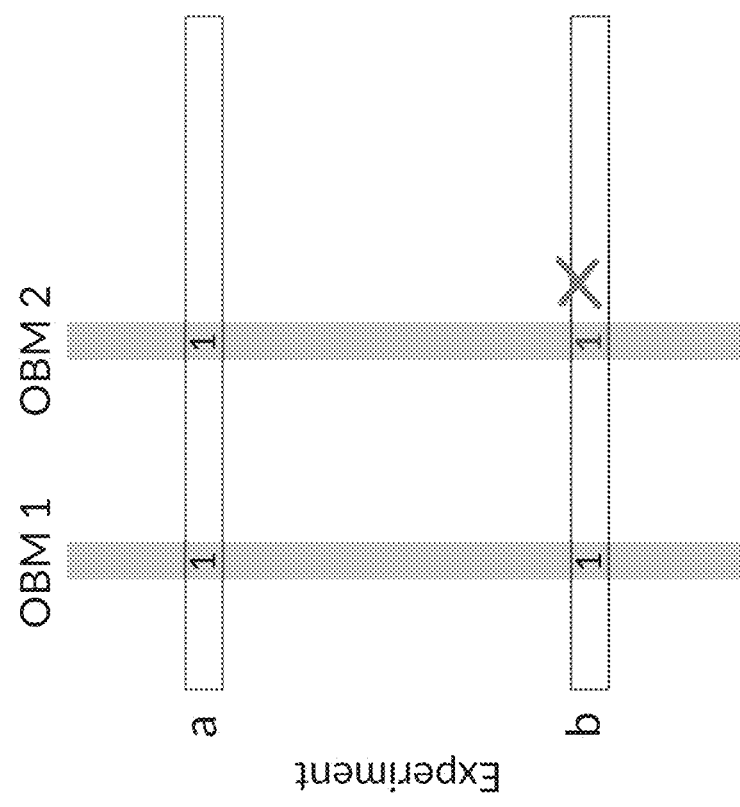
FIG. 6B The measurement matrix construction can be mapped to a graph problem, with blue nodes denoting experiments and green nodes denoting OBMs. Each experiment node is connected to OBMs and each OBM node is connected to P experiments, for a Pn×Kn matrix, when n is an integer greater than K Every non-zero element of 1 can be thought of as an edge on a bipartite graph connecting experiment nodes to OBM nodes. The constraint shown in the left can be thought of as establishing an edge to a new OBM node ("2" in B) only if the experiment node "b" is not already connected to node "2" by a length 3 path. Such a constraint must be followed by every experiment node and OBM node, in any construction of a graph to create a good measurement matrix (of minimal mutual coherence). The measurement matrix is just the adjacency matrix of this graph.

The measurement matrix construction can be mapped to a graph problem. The mapping to a graph clarifies the constraints on the measurement matrix, and leads the way to a new set of graph algorithms to that end. The measurement matrix can be mapped to a bipartite graph. see FIG. 4. Consider the rows of the matrix as "experiment nodes" in the graph, and the columns as "OBM nodes". There is an edge connecting an experiment node to an OBM node only if the OBM appears in the experiment. See FIG. 4—any construction of a graph such that every experiment node is connected to 3 OBM nodes, and any OBM node is connected to 2 experiments, must follow the constraint of edge property described in the FIG. 6 description.

Figure 5:
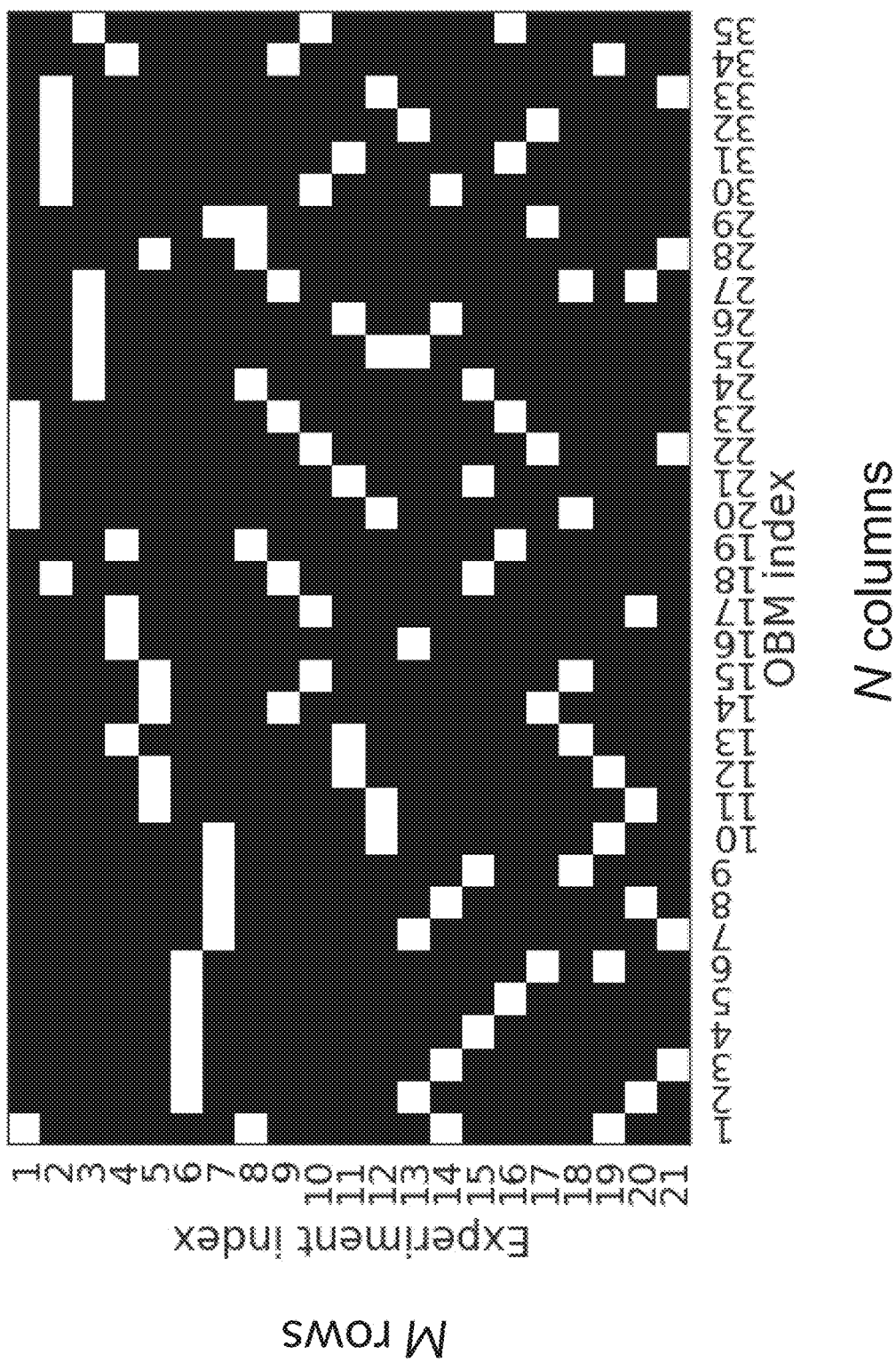
FIG. 5 is an exemplary depiction of a stochastic construction of a small measurement matrix 1 using the graph algorithm of the present disclosure.

With these preliminaries, the graph based algorithm for stochastic construction is presented in FIG. 5.

$l_1$-Sparsity Recovery: Setting the Lower Bound of Recovery

First, consider the recovery using the standard l1-sparsity convex optimization, which is not aware of the signal prior. The formalism developed in the first part of Example 1 improves this recovery.

Figure 7:
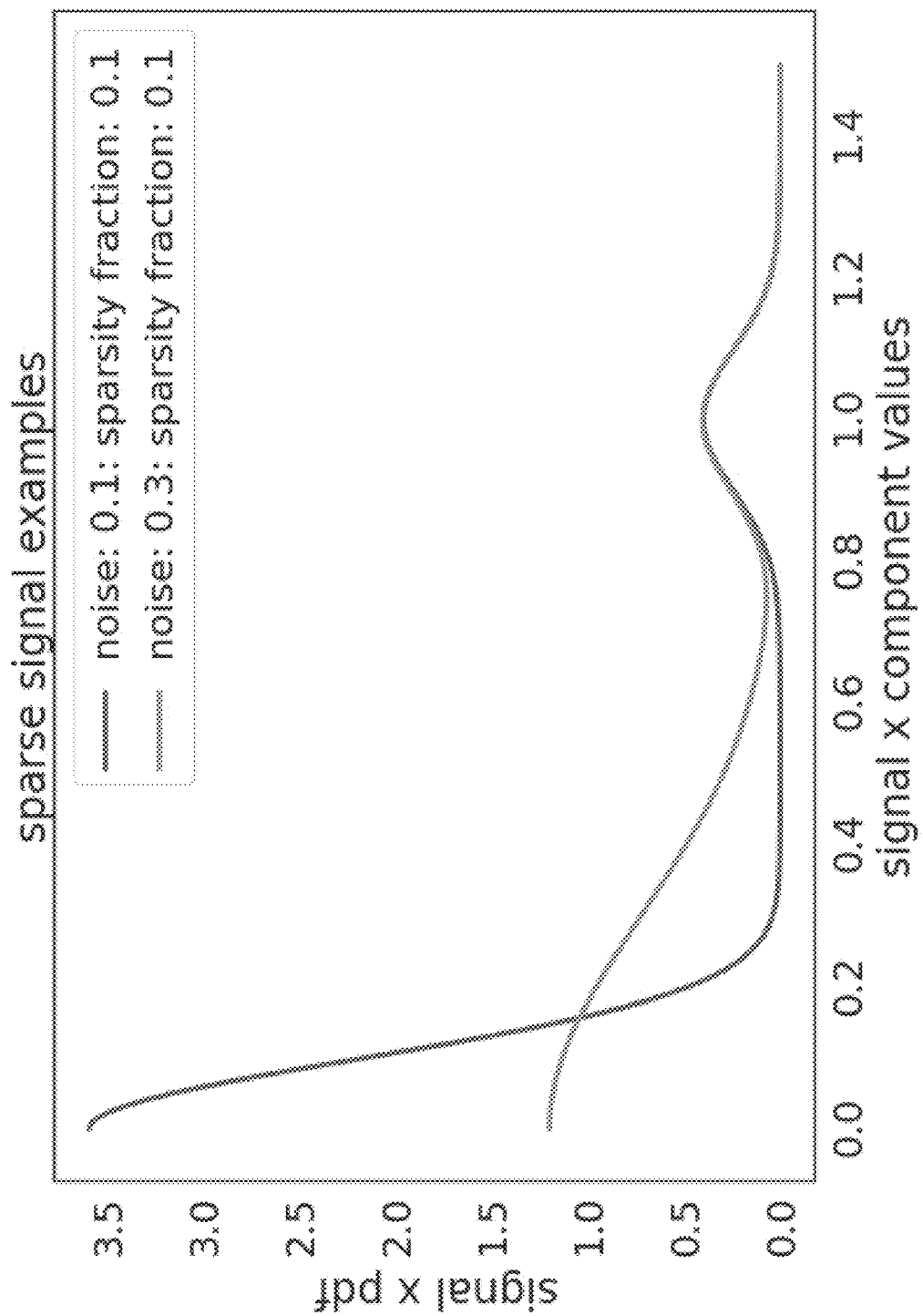
FIG. 7 shows typical examples of approximately sparse signal, modeled as a mixture of Gaussian used in simulation, where we fix sparse component standard deviation, $\sigma_s=0.1$ and mean $\mu_s=1$. The noise variance (i.e. the approximate-zero component) $\sigma$ is only changed to study robustness of the recovery using l1-sparsity, which is suboptimal, but sets the expectation for the worst-case scenario. A more optimal approach is to use the Bayesian message-passing solution.

The $l_1$-sparsity convex optimization problem is defined in Eq. 1. The algorithm is mostly insensitive to the sparsity parameter k, as long as it is greater than zero. Typical choice for us is λ=0.01. In order to check recovery, we use a approximately sparse signal model of mixture of two Gaussian, $$P(x) = \prod_{i=1}^{N} [\rho \psi(x_i) + (1-\rho)N(0, \sigma)]$$

where $\mu_s$ is the mean of the approximate sparse component, and $\sigma_s$ is the standard deviation. Example choices for the simulation, and typical examples are depicted in FIG. 7. The power of the measurement matrix construction lies in that even the sub-optimal method of using l1-sparsity leads to rather robust behavior in the presence of moderate noise.

Figure 8:
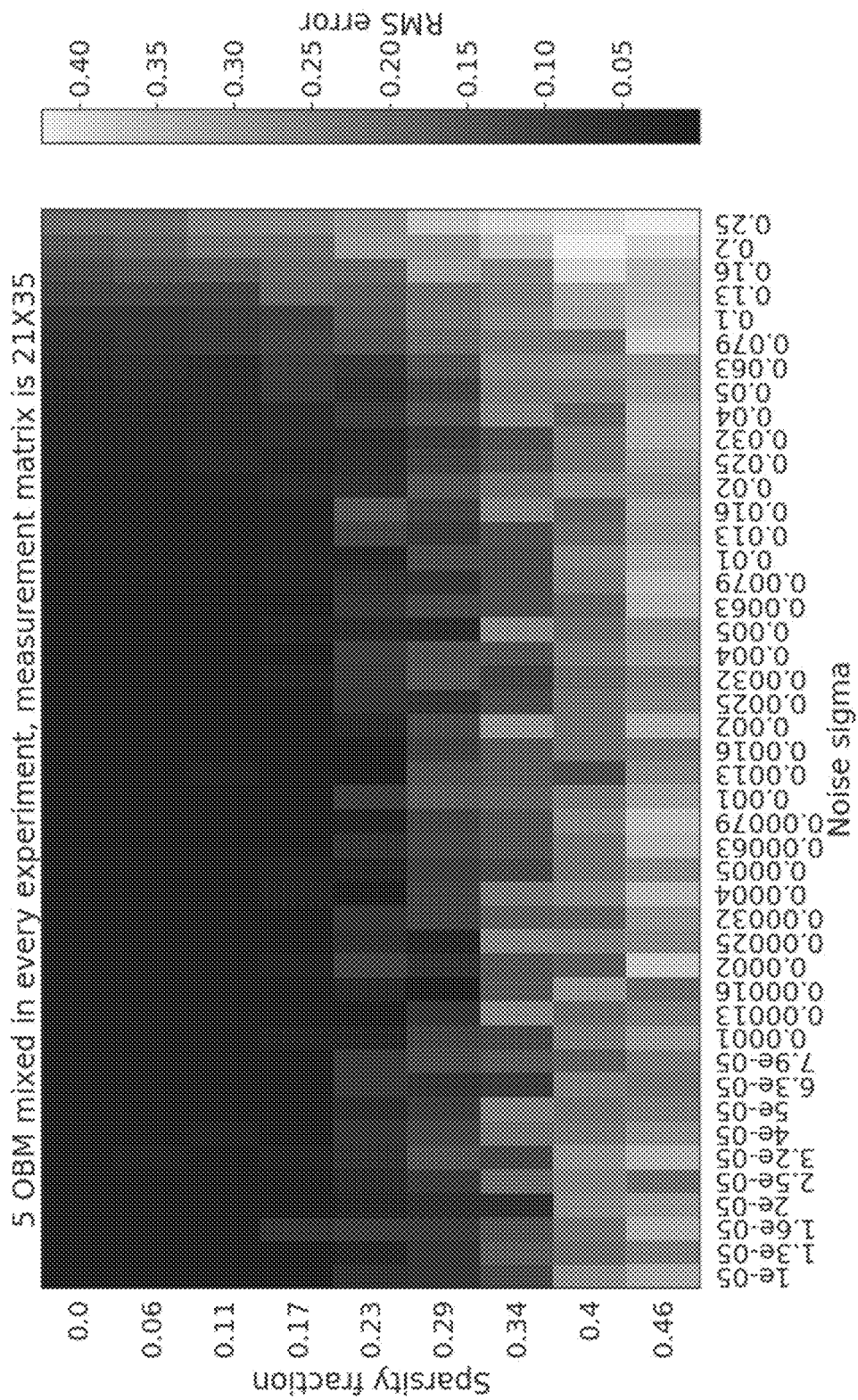
FIG. 8 is an exemplary depiction of a Phase diagram of recovery as a function of signal sparsity fraction p and noise component standard deviation $\sigma$ for a construction of $\Phi$. Note that l1-sparsity is only expected to work when signal is exactly sparse, i.e. $\sigma=0$. Sparse component mean and variance are fixed, $\sigma_s=0.1\sigma_m=1$ respectively. The sparse component parameters can be fixed without loss of generality owing to the rescaling freedom of the support x of the signal—only the ratio of variances and ratio of means of the sparse and noise components are the relevant parameters.
Figure 9:
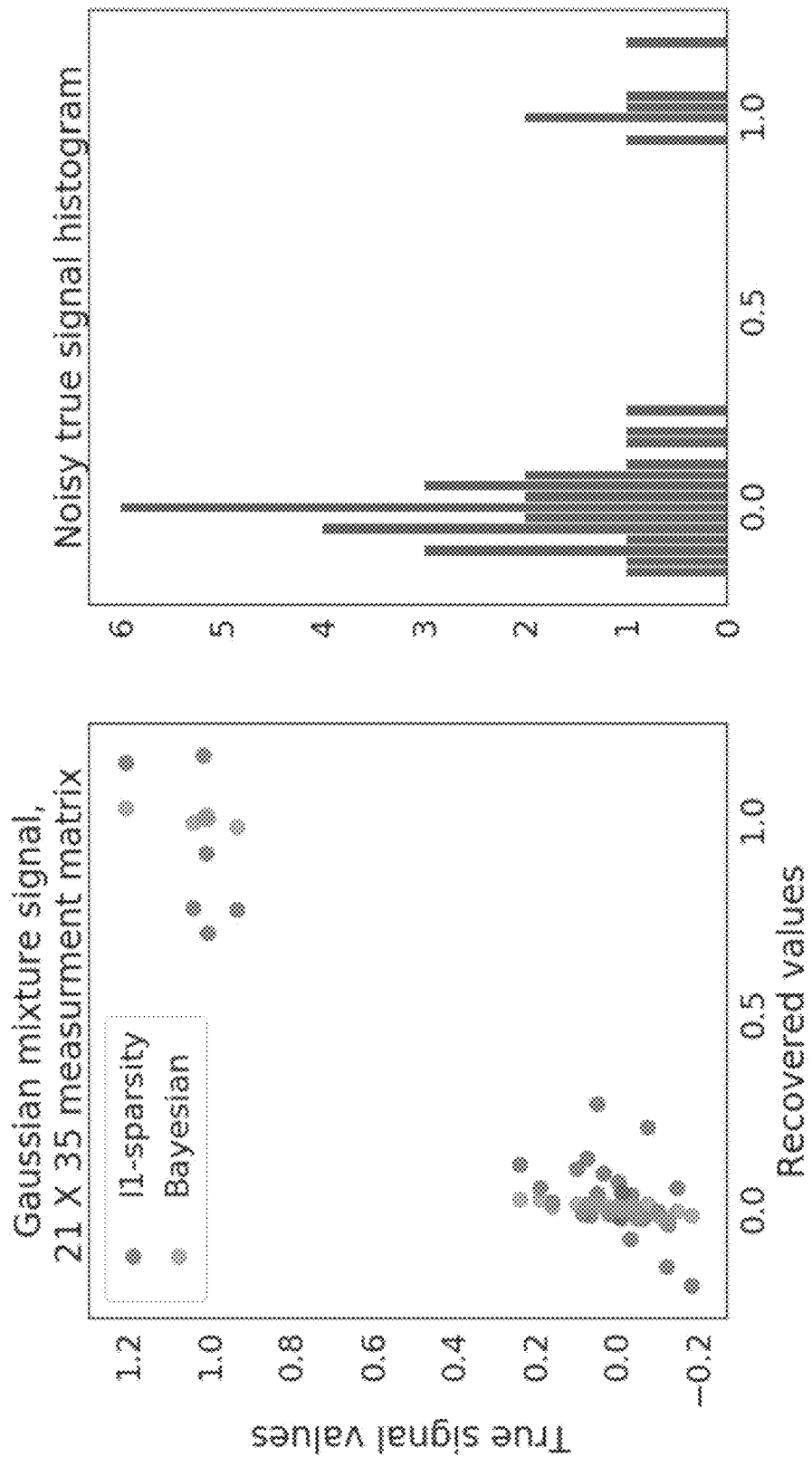
FIG. 9 For the same (unusually small) measurement matrix shown in FIG. 5, for 21 experiments using 35 OBMs, and for a Gaussian mixture model signal, with $\rho=0.16$. $\sigma=0.08$. $\sigma_s=0.1$. $\mu_s=1$, the l1-sparsity recovery was compared against our Bayesian approach. Notice the poor approximate sparsity of the signal, i.e., high $\sigma$.

FIG. 8 shows that even for such unusually small measurement matrices, recovery is surprisingly good. The dark region is where an exact signal recovery is obtained (RNS error is nearly zero), as judged by average RMS error over 10 different compressed sensing runs for each grid point of parameter choices. The parameter space is sparsity fraction p and noise of approximately sparse component, σ. See the approximate sparse signal model above. The standard deviation and mean of non-sparse component is fixed, $\mu_s$=1, $\sigma_s$=0.1, for the parameter space exploration because of the rescaling freedom of signal support, i.e., only the ratio of standard deviations and the ratio of the means of signal Gaussian components matter.

3 Bayesian Algorithm Results

The Bayesian algorithm is expected to perform better than the l1-sparsity algorithm in the regime where the noise in the signal σ, corresponding to the approximately sparsity close to zero values, is relatively large. The Bayesian algorithm is a loopy belief propagation. It is unstable for large σ and/or poor sparsity (large sparse fraction p), because of the theoretical limits (Donoho-Tanner transition) of recovery. These expectations are indeed met, similar to the recovery for l1-sparsity shown in FIG. 8.

For the same measurement matrix shown in FIG. 5, for 21 experiments using 35 OBMs, and for a Gaussian mixture model signal, with μ=0.16. σ=0.08. $\sigma_s$=0.1. $\mu_s$=1, we compare the l1-sparsity recovery against Bayesian approach. Note that a is what makes the signal approximately sparse, see FIG. 7.

The results are shown in FIG. 10. Observe that Bayesian approach leads to a clearer separation of sparse and approximately zero components.

IV. B. Example 2—Combinatorial Chemical Modifications, Combinatorial OBM Design Architectures, and Combinatorial Testing of Drugs in Clinical Trials

4.1 Problem Statement

Described herein are a diverse set of combinatorial measurement problems, fundamentally connected in the design constraints, and the description of methodologies to solve them. These combinatorial measurement problems share a common set of attributes:

1. The design is combinatorial of elements, and the goal is to learn both the independent contributions and pair-wise synergies/antagonisms/interactions of elements from measurement on mixtures of these elements optimally—we want to learn with a minimal set of combinations.
2. There are constraints on the number of combinations that can be tested together in any combinatorial mixture.
3. The combinatorial elements can be combined without any further restrictions, for example they are not mutually exclusive.

By "elements", in this example, the aspect is to capture several abstractions concrete realizations of elements are sequence motifs, chemical modifications, drugs etc. Note that if these elements violate the last assumptions of independence, for example, presence of one in a mixture precludes the presence of another, then by definition these elements cannot have synergies or antagonisms—the problem addressed herein is to infer synergies or antagonisms very efficiently. In this context, the design of the measurement matrix proposed here does not apply, however, a Markovian model where the transition matrix defines the allowed transitions can be constructed. The sparse learning paradigm proposed here still applies but the measurement matrix will be yet further customized in that case.

There are several problems where such combinatorial testing is needed. A few non-limiting examples are provided below, but the applications are broader than these specific exemplars:

1. Given the information profile of sequence (motifs) positions in an OBM for any pharmacological endpoint, we want to explore experimentally several combinations of chemical modifications and their potential in improving the pharmacology. It is expected that these modifications will be synergistic or antagonistic, both favorably or unfavorably.

In this case, the combinations of (sequence-context dependent) modifications one can include in any single OBM will typically be constrained by design criteria, position along the OBM, chemical synthesis feasibility or/and architecture of OBM. As one non-limiting example, consider we have N such (sequence-dependent) modifications we want to explore in experiments, but can only include K such modifications in any single OBM. The total number of combinations is typically huge, $$\binom{N}{K}$$

—a space unfeasible to explore exhaustively. There are N(N−1) pair-wise synergies or antagonisms to learn. It is not expected that synergies or antagonisms are somewhat sparse, but independent contributions are not. Note that these "modifications" may simply be sequence motifs at different positions in the OBM as long as they are non-overlapping, discovered as candidates to explore once the information profile in sequence-space is learned from a first set of experiments, see for example FIG. 11.

2. As another non-limiting example, consider configurations to explore are of an OBM architecture. A concrete example is "gapmer"-design architecture. Imagine the following design criteria on a background of non-cleavable regions. The gap is composed with two nucleotide units. Imagine the constraint that every OBM must have at least 5 of these two-nucleotide position-dependent "gaps" (our elements) but the OBM can be composed by placing these "gaps" in any position along the OBM. Imagine the length of the OBM is 20. Then there are 10 positions of the "gap" placement along the OBM. Obviously, the contribution of these position-dependent "gaps" to activity are synergistic or antagonistic and we want to quantify these synergies or antagonisms as well as individual contributions. The methods described in the present disclosure can determine the least number of OBMs to test.

3. As another non-limiting example, consider the challenge of the more traditional setting of combinatorial drug testing for any drugs. Typically, these combinatorial testing is constrained by the total number of drugs that can be administered in any single patient owing to practical reasons of minimal and maximal dosing, and complexity of drug-drug interactions dosing regimens.

As another non-limiting example, consider the challenge in identifying ideal drug combinations for N drugs and identify all the N (N−1)/2 synergy strengths and the N individual contributions of drug action. The methods described in the present disclosure can determine the number of patients M needed to design the combinatorial dosing to maximize learning, and minimize the cost of trial (number of patients in trial).

4.2 Highly Compact Measurement Matrix for Learning Interactions: Preamble

The properties of a measurement matrix that make querying synergistic or antagonistic interactions optimal are distinct from that which makes learning independent contributions optimal, as described previously. This is because, in the earlier construction mutual coherence was reduced to its theoretical minimum, represented by the graphical constraints in FIG. 6. Intuitively, this graphical constraint implies no pair of OBMs are tested together in more than one experiment—this statement holds for all pairs. However, this constraint implies that for learning synergies or antagonisms, such a construction will never query the synergistic or antagonistic contributions of any pair more than once! Another way of stating the problem is, in the current design, the measurement space is no longer the individual OBMs but pairs of OBMs and there is a need to design measurement matrices such that these pair-wise interactions are queried as equitably as possible. The theoretical ideal is that every pairwise interaction is queried exactly the same number of times.

4.3 Stochastic Construction

The stochastic construction is a similar graph construction, except that the constraint on edges is relaxed to, "every pair of OBM nodes must have edges to exactly B experiment nodes, and every OBM must have edges to exactly B (K+2) experiment nodes, and every experiment must have edges to exactly K experiments". This is a constrained graph construction problem, possible to achieve by brute force construction attempts, as shown in FIG. 5

4.4 Recovery

Figure 12:
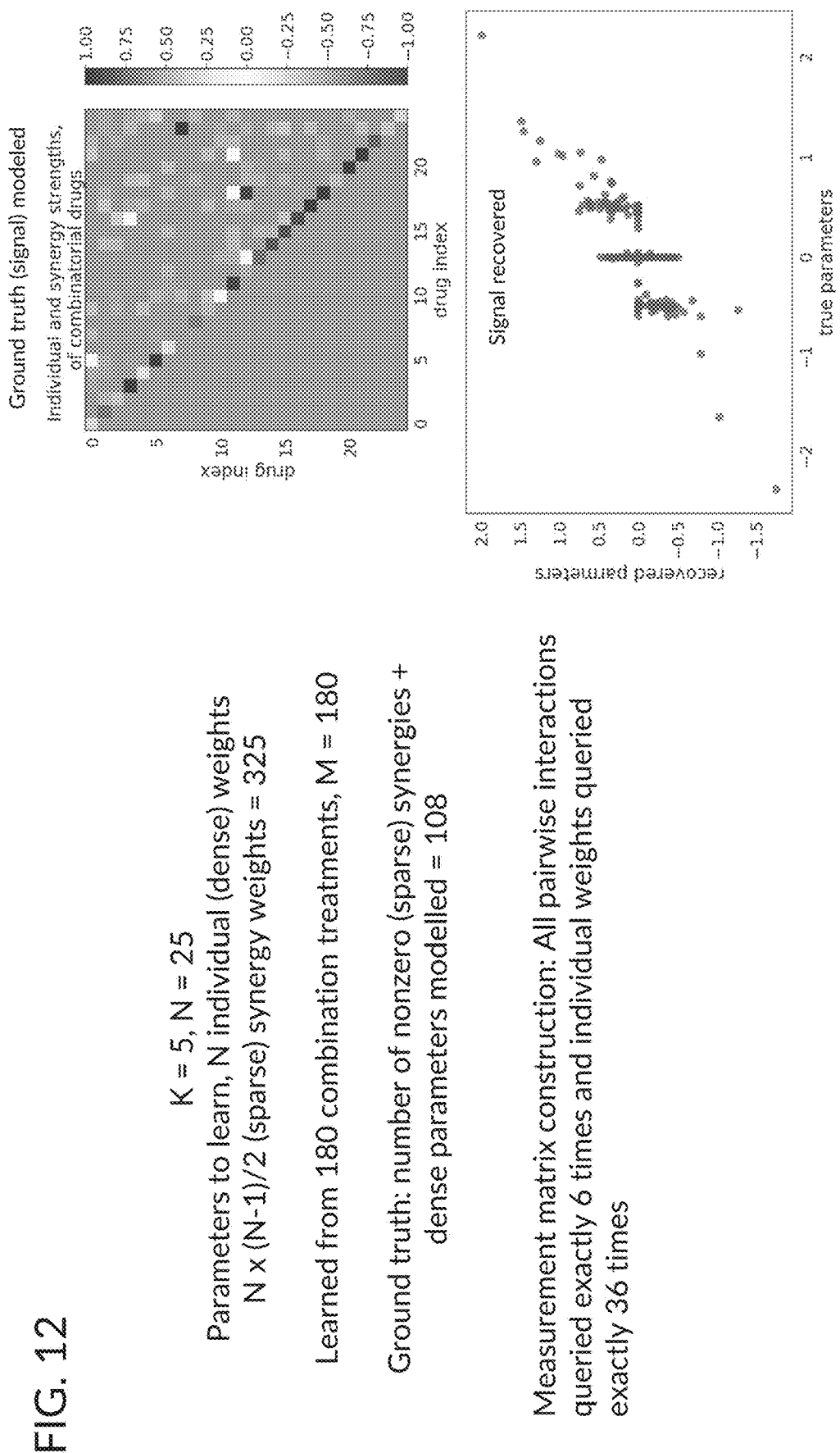
FIG. 12 is an exemplary depiction of learning (recovery of ground truth signal) of both pairwise synergistic and antagonistic interactions using data from far fewer treatments than there are parameters to learn. This is an extreme example, exigent on the performance of our model. Typically, there will be far fewer synergies/antagonisms in typical combinatorial drug testing.

FIG. 12 demonstrates example recovery where only 62% more combinations than (unknown) non-zero parameters (108 in this case), and with 55% measurements to the total number of parameters to learn (325 in this case) we reliably recover the strong synergies or antagonisms. In less extreme cases, recovery is only better. Such recovery is only possible with the extremely well-crafted measurement matrix design.

IV.C. Example 3—Validation of Compressed Sensing Recovery

In this study 35 compound mixtures were clinically tested. The rest of the design is identical to Study 2. Total animals tested in "compressed sensing" setting (Study 2 & 3 together) was 35+14=49, for 48 antisense oligonucleotides (ASOs). Reliable recovery by compressed sensing means we have reduced the number of animals required for drug testing by roughly a third.

In Vivo Methods

All animals were handled humanely and ethically with due regard for their welfare. Animals were maintained in a controlled environment with 22±3° C. temperature, 50±20% humidity, a light/dark cycle of 12 hours each and 15-20 fresh air changes per hour. Animals were housed group wise (3 animals per cage) and autoclaved corncob was used as a bedding material. The animals were fed ad libitum, with a certified irradiated laboratory rodent diet. Potable water, filtered through reverse osmosis, was autoclaved, and provided ad libitum to all animals via polycarbonate bottles fitted with stainless steel sipper tubes.

Animals were randomized into treatment groups based on their body weight. After randomization, animals were assigned a permanent number. Cages were identified by cage cards indicating the study number, study code, group number, sex, dose, cage number, number of animals and animal number details.

Preformulated ASOs were supplied at a concentration of 10 mg/ml. Animals were dosed at 50 mg/kg per ASO; total dose 200 mg/kg. An equal volume mix of 4 ASOs was made according to the measurement matrix of FIG. 17. Mice were dosed subcutaneously with the ASO mix. The volume was calculated based on animal body weight.

Animals received dose 1 of the respective antisense oligos (ASOs) on day 1 and dose 2 on day 5. The dose was calculated based on animal body weight and was approximately 390 to 480 µl.

Body weight was recorded individually, and animals were randomized into different treatment groups based on the body weight prior to dosing. Animals were observed for adverse clinical signs and mortality immediately post dosing until study termination. Bodyweight was recorded prior to each dose and before termination.

Animals were kept in fresh cages lined with aluminum foil between 6:30-7:30 a.m. and animals were placed in the cages for 6-8 hours, until sufficient urine volume was obtained. Urine was collected once every 2-3 hours to prevent contamination and evaporation and stored under appropriate conditions.

Blood was collected from the retro-orbital plexus from all animals to measure liver function parameters. 72 hours post dosing, animals were fasted for 6 hours and approximately 200 µl blood was collected into serum collection tubes under mild isoflurane anesthesia. Blood was centrifuged at 3000 g for 15 minutes at 4° C. Serum was separated into fresh, labelled Eppendorf tubes and stored at −80° C. until analysis.

On day 15 of the study, animals from all groups were subjected to mild isoflurane anesthesia and blood was collected from the retro-orbital plexus. 0.2 ml of whole blood was placed in K2-EDTA coated tubes and used to perform a complete blood count (CBC). 0.3-0.4 ml of blood was collected in serum collection tubes and centrifuged at 3000 g, 4° C. for 15 minutes. Serum was separated and stored in fresh labelled Eppendorf tubes. Samples were stored at −20° C. until analysis or transferred to −80° C. for long-term storage.

Animals were euthanized after blood collection, and liver, kidney and spleen tissue were collected. The central lobe of the liver and one kidney were placed in labelled tissue cassettes and put into 10% neutral buffered formalin (NBF). Tissues were weighed and placed in tubes containing RNA later. Samples were stored at room temperature for 24 hours and transferred to −80° C. for long-term storage.

Alanine Aminotransferase (ALT), Aspartate Aminotransferase (AST) and Serum/Urinary creatinine levels were estimated in serum using the Siemens Dimension® Xpand® Plus Clinical Chemistry System. Commercially available Siemens dimension kits were used for analysis.

Alanine aminotransferase catalyzes the transamination of L-alanine to á-ketoglutarate (á-KG), forming L-glutamate and pyruvate. The pyruvate formed is reduced to lactate by lactate dehydrogenase (LDH) with simultaneous oxidation of reduced nicotinamide-adenine dinucleotide (NADH). The change in absorbance is directly proportional to the alanine aminotransferase activity and is measured using a bichromatic (340, 700 nm) rate technique (ALTI Flex® reagent cartridge, Cat. No. DF143).

Aspartate aminotransferase (AST) catalyzes the transamination from L-aspartate to á-ketoglutarate, forming L-glutamate and oxalacetate. The oxalacetate formed is reduced to malate by malate dehydrogenase (MDH) with simultaneous oxidation of reduced nicotinamide adenine dinucleotide (NADH). The change in absorbance with time due to the conversion of NADH to NAD is directly proportional to the AST activity and is measured using a bichromatic (340, 700 nm) rate technique (AST Flex® reagent cartridge, Cat. No. DF41A).

A modification of the kinetic Jaffe reaction is employed. In the presence of a strong base such as NaOH, picrate reacts with creatinine to form a red chromophore. The rate of increasing absorbance at 510 nm due to the formation of this chromophore is directly proportional to the creatinine concentration in the sample and is measured using a bichromatic (510, 600 nm) rate technique (CRE2 Flex® reagent cartridge, Cat. No. DF33B).

Kim-1 and Cystatin-C levels were estimated in urine samples collected 24 hours post dose 1 and dose 2.

Urine samples were thawed, centrifuged and the supernatant was used for analysis. Samples were diluted 1000× for cystatin-c and 100× for Kim-1. Standards and samples were analysed in duplicates.

50 µl of diluted plasma was added to a 96 well plate and the assay was performed as per the kit protocol (R&D systems Mouse/Rat Cystatin C Immunoassay, Mouse/Rat Cystatin C Quantikine ELISA Kit MSCTC0). After the final color development, absorbance was measured by colorimetric analysis at 450 nm using Thermoscan spectrum (Plate Reader-Spark-10M, Tecan) and results were recorded. Standard curve was generated using standards provided in the kit.

To measure urinary KIM-1, 50 µl of diluted urine samples were added to a 96 well plate and the assay was performed as per the kit protocol (R&D systems Mouse immunoassay Mouse TIM-1/KIM-1/HAVCR Quantikine ELISA Kit MKM100). After final color development, absorbance was measured by colorimetric analysis at 450 nm using Thermoscan spectrum (Plate Reader-Spark-10M, Tecan) and results were recorded. Standard curve was generated by using the standards provided in the kit Formalin fixed liver and kidney tissue were embedded in paraffin and blocks were prepared. 4-5 µm sections were cut and stained with hematoxylin and eosin. Stained sections were air-dried, dehydrated and coverslipped. Sections were observed by two trained pathologists and a qualitative score was assigned to each section based on the type and extent of lesions observed.

In vitro Methods

Cells (A431, HEK-293, HeLa, HepG2, 3T3, and donor fibroblasts) were dosed with select ASOs at a variety of concentrations (40 µM to 2.5 µM) using either free-uptake or electroporation (BTX ECM 830 square wave generator with an HT 96 plate handler using 4 mm gap plates). Cells were plated at approximately 10,000 cells per well (with variations per cell line based on cell size) in a 384-well cell culture plate. Following a five hour recovery from electroporation or 24 hour incubation for free uptake, cells were washed with PBS and bathed in media (MEM-α with 10% FBS) spiked with selected reporters using a liquid handler (Integra Viaflo 96), with each well having both a fluorescent green dye and a luciferase-based luminescent enzyme and substrate. Cells were imaged with transmitted light to confirm viability and cell density. CellEvent Caspase 3/7 fluorescent green dye (ThermoFisher #C10423) was used in conjunction with the luciferase-based RealTime-Glo MT Viability Assay (Promega #G9712). RealTime-Glo Annexin V Apoptosis and Necrosis Assay (Promega #JA1012) was used in parallel and contains both the Necrosis Green fluorescent dye and an Annexin V-sensitive luciferase assay. The CellEvent Caspase 3/7 and Necrosis Green fluoresce when exposed to active caspases or nucleic acids, respectively, and accumulate over time. The RealTime-Glo MT Viability Assay and RealTime-Glo Annexin V Apoptosis Assay use a Nano-Luc luciferase enzyme that cleaves a substrate to produce light upon exposure to a reducing environment (such as in a viable cell) or when exposed to Annexin V (which become accessible when the cell membrane is disrupted), respectively. These luciferase assays are non-cumulative and provide real-time readouts. All readings were performed in 384-well white-walled tissue culture plates (Greiner #781098) and read on a BioTek Cytation 5 (fluorescence was read at 503 excitation/530 emission, bandpass).

Results

FIG. 13 illustrates liver toxicity in response to dosing. ALT (Alanine aminotransferase), a measure of liver toxicity, measured 72 hours after the first dose. Notice that that the distribution is very approximately sparse (once shifted by normal range of ALT of 50-100 u/L) and not exactly sparse, the latter being necessary for traditional compressed sensing setting—here we manage to recover signal with such distributions FIGS. 14A & 14B illustrate the typical time series of liver toxicity (column 5, ALT is black, AST is gray, x axis are the three time points (see study design), with increasing toxicity observed after the second dose for toxic ASOs, owing to accumulating toxic effects. Values of 4 are dead animals. Also shown are cytotoxicity feature space (HeLa cells, readouts of apoptosis, necrosis, cell viability and membrane integrity, see In Vitro Methods).

Figure 15:
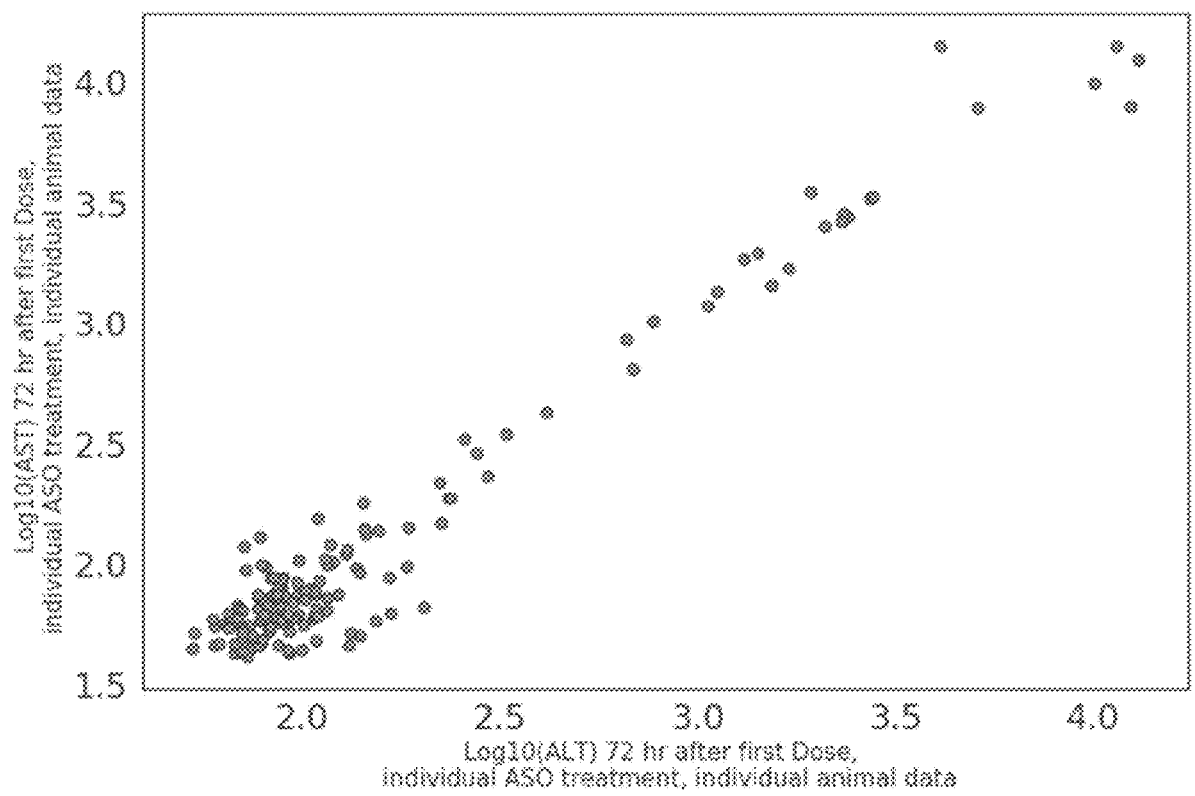
FIG. 15 plots Aspartate aminotransferase (AST) and Alanine aminotransferase (ALT) in liver toxicity response for individual ASOs tested, illustrating that the toxicity response is robust and highly correlated across the two common liver toxicity endpoints.

FIG. 15 illustrates correlation between Aspartate aminotransferase (AST) and ALT (Alanine aminotransferase) in liver toxicity response for ASOs tested.

Calibration

Before compressed sensing to recover toxicity of any set of drugs from mixture treatments, the sensing system 200 calibrates the learning paradigm.

Calibration included calibrating the minimum dose to evoke toxic response across a large collection of ASOs, which was 20-40 mg/kg for mice per week (single dose), and the maximum dose tested was 225 mg/kg per week (single dose). This calibration step determined mixes of up to 4-5 ASOs. 4 ASOs were chosen, at 50 mg/kg each, with a total mixture dose of 200 mg/kg. Both values (min dose per ASO and max total dose) were well within the experimentally determined range.

The second calibration step is determining the parameters for a linear fit of average behavior of mixtures to the naive additive expectation. This is necessary to calibrate the additive response to mixtures, and the calibration step is in fact an advantage of our innovation—unlike traditional setting, we do not need to assume that the signal in a compressed sensing scenario is strictly a sum of individual contributions. After calibration step, the parameters for the equation $y=m\ x+c$, where y is the sensed (mixture) log 10(ALT) and x is expected value from additive model, $x=M\ z$ where M is the sensing matrix and z are the true values of (individual ASO) log 10(ALT). With this calibration step we obtain m=0.43 and c=−1.34. Note that this calibration step has to be performed for each pharmacological endpoint only once; priming readiness for compressed sensing experiments. Note that though in this example, the calibration step used a linear model, a nonlinear fitting function can be employed when necessary, as long as the function is invertible.

Figure 16:
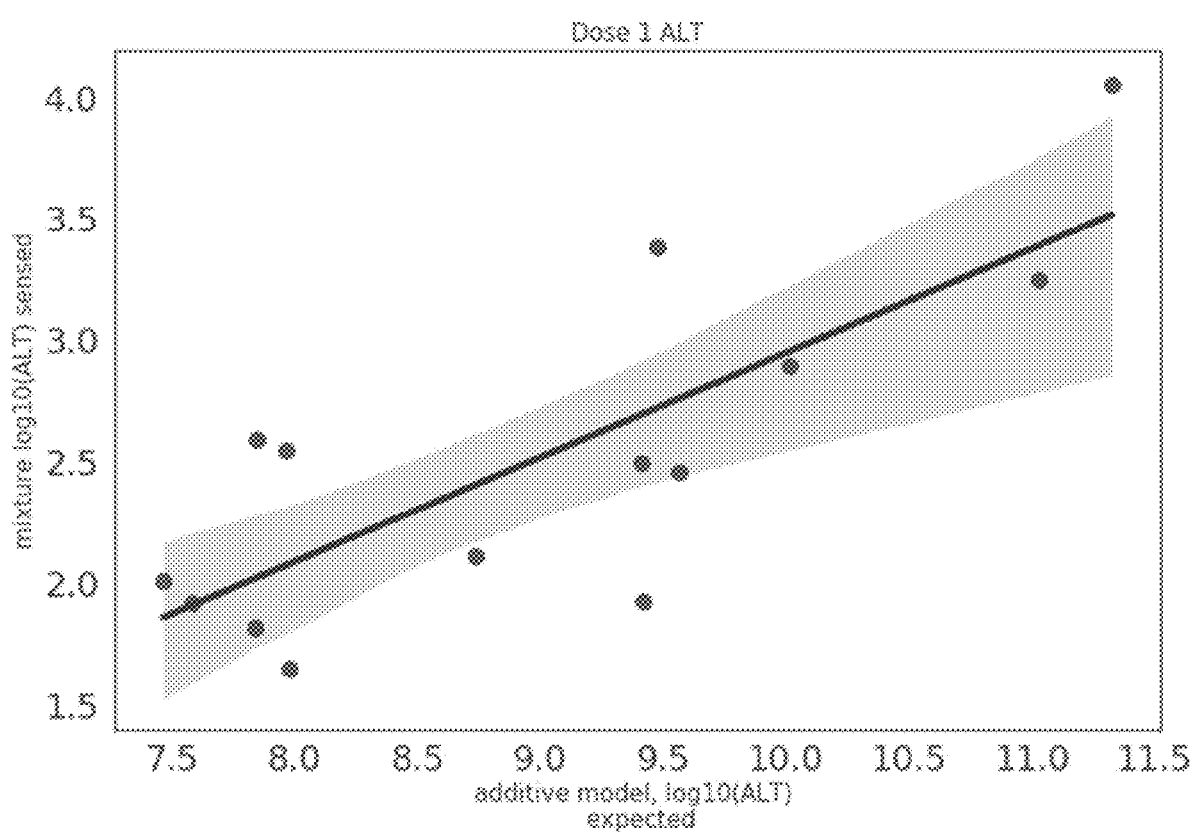
FIG. 16 illustrates the calibration step for learning additive scaling. Calibration step: A key step in compressed sensing in our setup is to calibrate the additive/approximately-additive response from mixture. Here we tested 14 mixtures, 4 ASOs in every mixture (50 mg/kg for each ASO, 200 mg/kg total dose per mixture, dosed in mice in single dose, one biological replicate). We also tested the ASOs individually (75 mg/kg per ASO, single dose, in 3 biological replicates). The x-axis is sum over the mixture-ASOs median log 10(ALT) over the three replicates for individual treatment. The y-axis is the log 10(ALT) measured for the corresponding mixture. We do not expect for any pharmacological readout on a mixture to simply be the naive sum of the individual responses obtained from individual treatments, because of the nonlinear response of physiology, and in general, any biological system. Moreover, the dose scales need not be naively additive. Here we show that in log space, ALT response of the mixture turned out to be captured well by a linear model, notwithstanding animal level noise deviating from this linearity. This linear model is invertible, and is used to scale the response from mixture experiments. This fit constitutes the calibration step. The fitting model need not be linear and, in general, the calibration step will not involve a linear fit, but a non-linear invertible fit.

FIG. 16 illustrates the calibration step for learning additivity scaling. Data in relation to dose 1 of ALT.

Compressed Sensing

In the sensing step, the measurement matrix (in FIG. 17) is used to recover the true signal (average of log 10(ALT) and log 10(AST) after the first dose. The calibration step corrects for the shift and scaling of the mixture signal. In spite of sensing in a single animal—animal-to-animal variability was observed to be high for high ALT/AST values (because the animal's response to highly toxic compounds is far away from homeostasis range). The predictive model was able to identify the toxic ASOs (ALT, AST>100 u/L) quite well. There are 4 ASOs which are toxic that the compressed sensing misidentified as safe.

Figure 17:
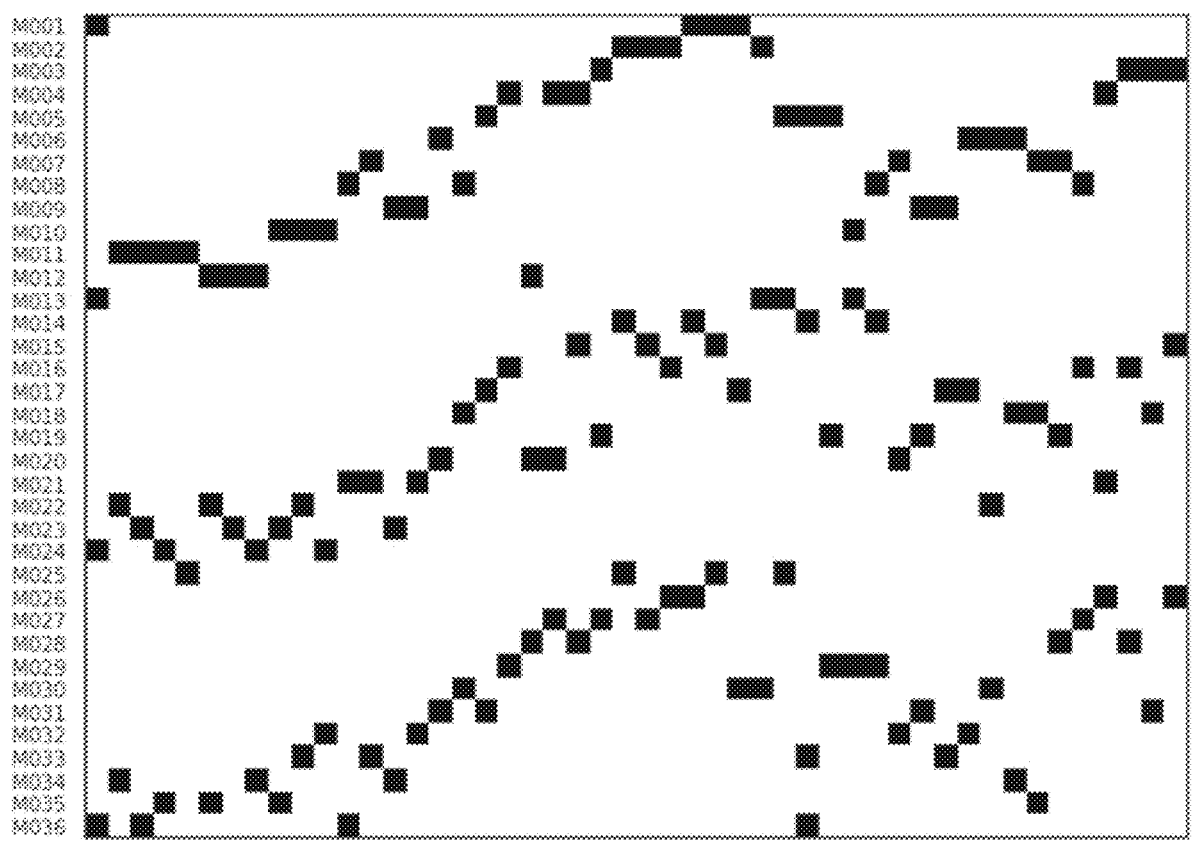
FIG. 17 illustrates the measurement matrix used for compressed sensing. The measurement matrix comprised 36 sensing mixtures of 48 ASOs. Dark boxes are values of 1.

FIG. 17 illustrates the measurement matrix. Here every mix (rows of the matrix) is equal proportion (by weight) of each ASOs (dark boxes, column index) selected for the mixture.

Note that the true signal after the first dose is only approximately sparse. Success in compressed recovery is not obvious on such signals. An approximate two-third reduction in animal usage was obtained between the 3 replicate study and compressed study (the individual ASO study utilized 108 animals whereas the compressed sensing study only utilized 36 animals.)

Figure 18:
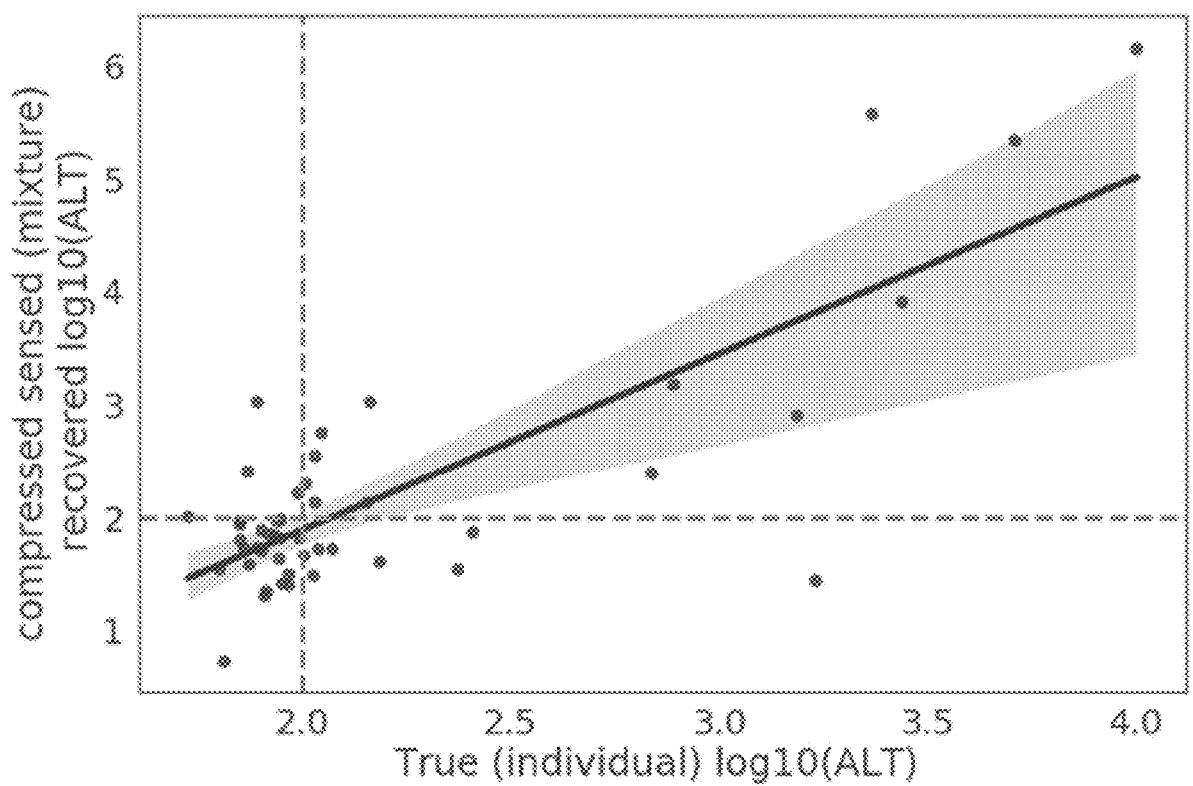
FIG. 18 illustrates the compressed sensing power of the predictive model after dose 1. Recovery from 36 mixes and 36 animals, learning 48 ASO pharmacology on 144 animals. Given the animal to animal noise/variation in readout, and that there were no biological replicates for the mixture dosing, the sensing is quite precise. Notice that almost all highly toxic ASOs (log 10(ALT)>2.5, ALT ≳300) can be identified with high precision. This is sensed only on one time point (72 hr after first dose) in a longitudinal study that collects two other timepoints (72 hr after second dose, and terminal bleed at day 15) which improves the result (FIG. 19).

FIG. 18 illustrates the compressed sensing power of the predictive models. With the clinical data collected according to the measurement matrix of FIG. 17 and performed according to the Methods discussed above, the sensing system 200 trained a predictive model (e.g., according to the method of FIG. 2B). Recovery from 35 mixes and 35 animals, learning 48 ASO pharmacology on 144 animals. Given the animal-to-animal noise/variation in readout, and that there were no biological replicates for the mixture dosing, this is quite precise and eliminates toxic compounds with high precision. Generally, log 10(ALT) greater than 2.0 was deemed to be a toxic response while below that threshold was a non-toxic response. The grey shading illustrates uncertainty of the fit, e.g., to accommodate animal variability.

Another consideration was whether the predictive model could sense the toxicity for later end point (Dose 2) where the distribution of true signal is even farther from approximate sparsity, and the signal is roughly bimodal and not very sparse, sparsity density is roughly half. For such a setting response at earlier dose and time point, and in vitro data is leveraged to create priors. The deviation from such priors is a sparse space, and the signal could again be recovered.

Figure 19:
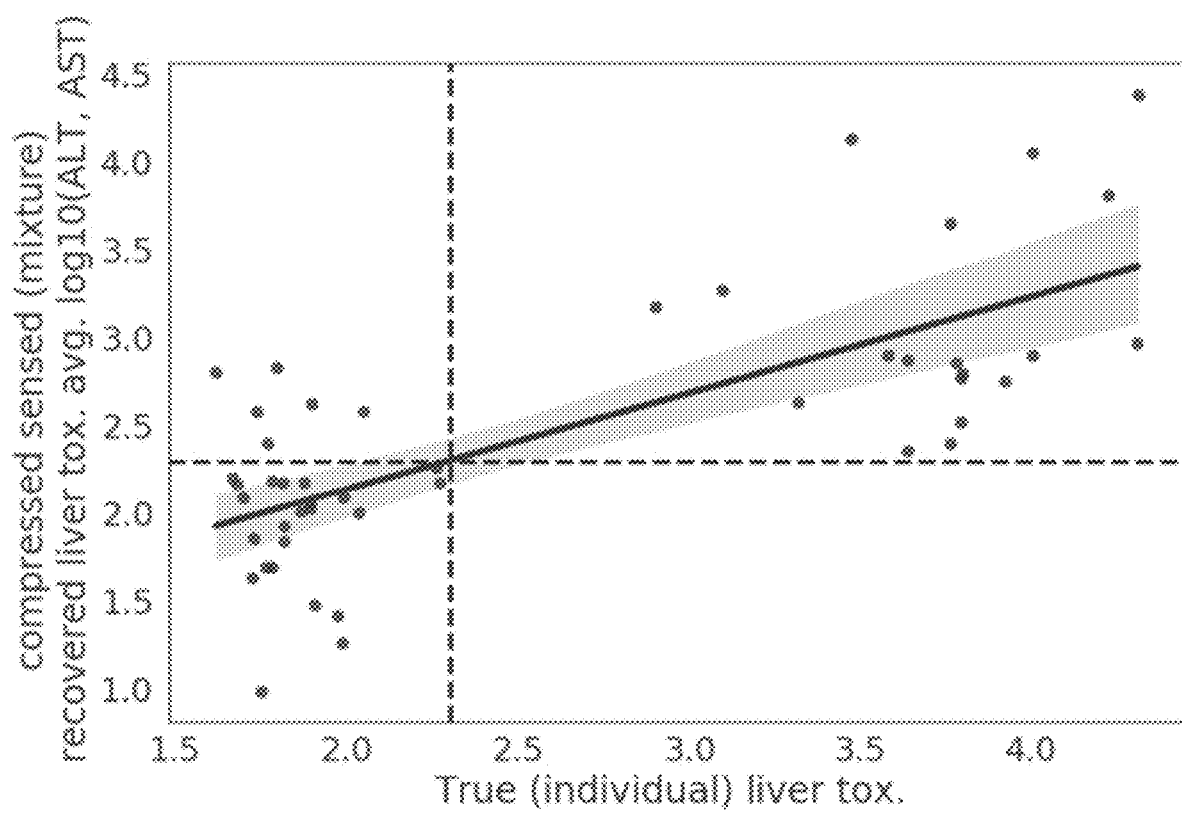
FIG. 19 illustrates the compressed sensing power of the predictive model after dose 2. Compressed sensing of toxicity after Dose 2, with average of log 10(ALT) & log 10(AST) sensed. In vitro datasets were used as priors to compute deviation from expectation. This deviation is the space in which the signal is approximately sparse. Note that for measurements around the safe threshold of 2 (ALT, AST~100), the signal is more noisy owing and so is recovery. Compressed sensing now identifies all the toxic (ALT, AST>200 u/L) ASOs correctly, and mislabels a few safe ASOs as toxic. With such severe reduction in animal numbers (from 144 to 36) one can afford to do follow up validation studies on a few ASOs after compressed sensing step, and still have plenty of reduction in animal numbers.

FIG. 19 illustrates the compressed sensing power after dose 2. Predictive machine learning models of liver toxicity along with in vitro datasets were used as priors to compute deviation from expectation. This deviation is the space in which the signal is approximately sparse. Note that for measurements around the safe threshold of 2 (ALT, AST~100), the signal is more noisy and so is recovery. Compressed sensing does identify all the toxic (ALT, AST>200 u/L) ASOs correctly.

Figure 20:
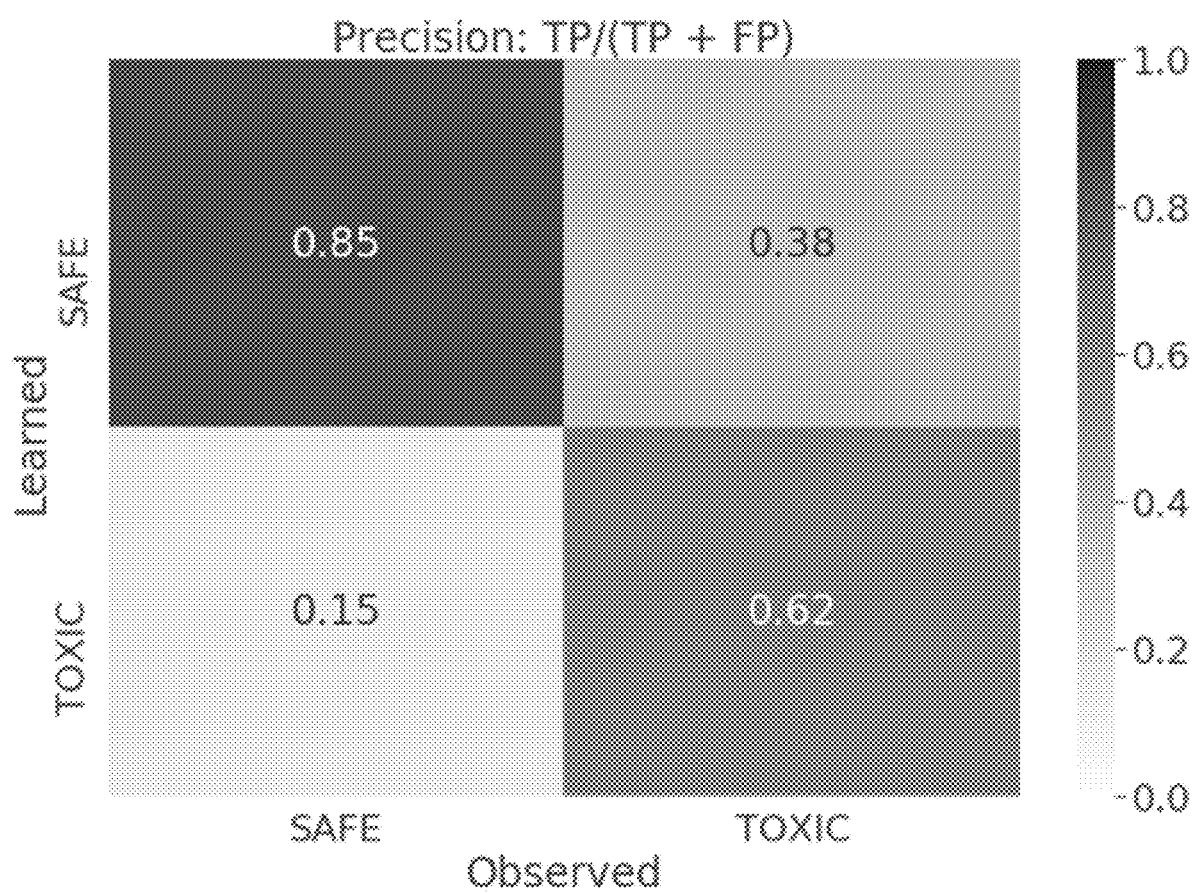
FIG. 20 is a precision matrix plot summarizing the predictive power of the compressed sensing models. log 10(ALT)>100 was used as a cutoff for calling toxicity (connected to FIG. 19, to assess sensing performance.) Overall, the method is precise on safety.

FIG. 20 is a confusion matrix summarizing the predictive power of the compressed sensing models. Precision plot with log 10(ALT)>100 was used as a cutoff for calling toxicity (connected to FIG. 5, to assess sensing performance.) Overall, the method is precise on safety.

In effect, by using in vitro data, and longitudinal measurements on the same animal, the compressive sensing method can reduce animal testing by 3 fold, without compromise in accuracy in identifying toxic ASOs. FIG. 17 illustrates a measurement matrix used for the compressed sensing. Here every mixture (rows of the matrix) has equal proportion (by weight) of each ASOs (dark boxes, column index) selected for the mix. Each ASO is also approximately equally present in the same number of mixtures.

V. EXAMPLE COMPUTING DEVICE

Figure 21:
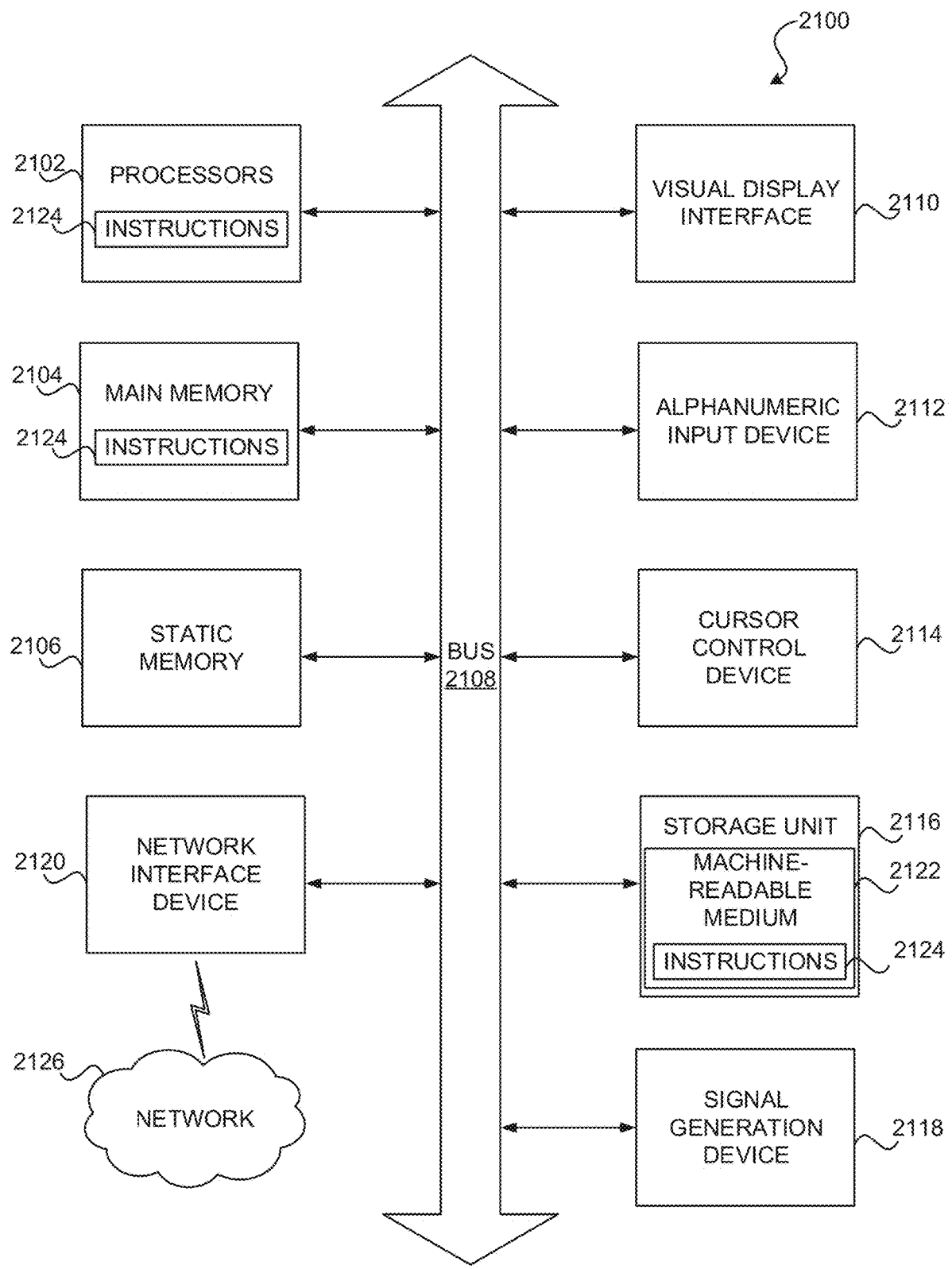
FIG. 21 is a block diagram illustrating components of an example machine able to read instructions from a machine-readable medium and execute them in a processor (or controller).

FIG. 21 is a block diagram illustrating components of an example machine 2100 able to read instructions from a machine-readable medium and execute them in a processor (or controller). Specifically, FIG. 21 shows a diagrammatic representation of a machine 2100 in the example form a computer system, within which program code (e.g., software or software modules) for causing the machine to perform any one or more of the methodologies discussed above may be executed. The program code may be comprised of instructions 2124 (e.g., software) executable by one or more processors 2102. In alternative embodiments, the machine 2100 operates as a standalone device or may be connected (e.g., networked) to other machines. In a networked deployment, the machine 2100 may operate in the capacity of a server machine, a client machine in a server-client network environment, or a peer machine in a peer-to-peer (or distributed) network environment.

The machine 2100 may be a server computer, a client computer, a personal computer (PC), a tablet PC, a set-top box (STB), a personal digital assistant (PDA), a cellular telephone, a smartphone, a web appliance, a network router, switch or bridge, or any machine capable of executing instructions 2124 (sequential or otherwise) that specify actions to be taken by that machine. Further, while only a single machine 2100 is illustrated, the term "machine" shall also be taken to include any collection of machines that individually or jointly execute instructions 2124 to perform any one or more of the methodologies discussed above.

The example computer system 2100 includes a processor 2102 (e.g., a central processing unit (CPU), a graphics processing unit (GPU), a digital signal processor (DSP), one or more application specific integrated circuits (ASICs), one or more radio-frequency integrated circuits (RFICs), or any combination of these), a main memory 2104, and a static memory 2106, which are configured to communicate with each other via a bus 2108. The computer system 2100 may further include visual display interface 2110. The visual interface may include a software driver that enables displaying user interfaces on a screen (or display). The visual interface may display user interfaces directly (e.g., on the screen) or indirectly on a surface, window, or the like (e.g., via a visual projection unit). For ease of discussion the visual interface may be described as a screen. The visual interface 2110 may include or may interface with a touch enabled screen. The computer system 2100 may also include alphanumeric input device 2112 (e.g., a physical or touchscreen keyboard), a cursor control device 2114 (e.g., a mouse, trackball, joystick, motion sensor, touchscreen, or other pointing instrument), a storage unit 2116, a signal generation device 2118 (e.g., a speaker), and a network interface device 2120, which also are configured to communicate via the bus 2108.

The storage unit 2116 includes a machine-readable medium 2122 (e.g., a non-transitory machine-readable medium) on which is stored instructions 2124 embodying any one or more of the methodologies or functions described herein. The instructions 2124 may also reside, completely or at least partially, within the main memory 2104 or within the processor 2102 (e.g., within a processor's cache memory) during execution thereof by the computer system 2100, the main memory 2104 and the processor 2102 also constituting machine-readable media. The instructions 2124 may be transmitted or received over a network 170 via the network interface device 2120.

While machine-readable medium 2122 is shown in an example embodiment to be a single medium, the term "machine-readable medium" should be taken to include a single medium or multiple media (e.g., a centralized or distributed database, or associated caches and servers) able to store instructions (e.g., instructions 2124). The term "machine-readable medium" shall also be taken to include any medium that is capable of storing instructions (e.g., instructions 2124) for execution by the machine and that cause the machine to perform any one or more of the methodologies disclosed herein. The term "machine-readable medium" includes, but not be limited to, data repositories in the form of solid-state memories, optical media, and magnetic media.

VI. ADDITIONAL CONSIDERATIONS

The foregoing description of the embodiments of the disclosure has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules can be embodied in software, firmware, hardware, or any combinations thereof.

Any of the steps, operations, or processes described herein can be performed or implemented with one or more hardware or software modules, alone or in combination with other devices. In some embodiments, a software module is implemented with a computer program product including a computer-readable non-transitory medium containing computer program code, which can be executed by a computer processor for performing any or all of the steps, operations, or processes described.

Embodiments can also relate to a product that is produced by a computing process described herein. Such a product can include information resulting from a computing process, where the information is stored on a non-transitory, tangible computer readable storage medium and can include any embodiment of a computer program product or other data combination described herein.

Finally, the language used in the specification has been principally selected for readability and instructional purposes, and it cannot have been selected to delineate or circumscribe the inventive subject matter. It is therefore intended that the scope of the invention be limited not by this detailed description, but rather by any claims that issue on an application based hereon. Accordingly, the disclosure of the embodiments herein is intended to be illustrative, but not limiting, of the scope of the invention, which is set forth in the following claims.

What is claimed is:

1. A method for optimizing pharmacological compound development, comprising:
    a. accessing, for each compound of a plurality of compounds, effect information describing an effect of the compound;
    b. iteratively training a machine-learned compound experiment model until a threshold criterion is satisfied by:
        i. generating, for each of a plurality of experiments, a corresponding set of compounds to combine together in the experiment using the effect information;
        ii. performing, for each of the plurality of experiments, the experiment by applying the corresponding set of compounds in a subject;
        iii. determining, for each of the plurality of experiments, a resulting set of effects of the applied set of compounds within the subject;
        iv. determining, for each of the plurality of experiments, an association between each effect of the resulting set of effects and a compound of the applied set of compounds to which the effect is attributed; and
        v. updating the effect information based on the determined associations between effects and compounds;
        vi. wherein the total number of experiments performed while training the compound experiment model is less than a total number of possible combinations of the plurality of compounds.

2. The method of claim 1, wherein the trained compound experiment model comprises a matrix.

3. The method of claim 1, wherein the effect is selected from:
    a. a biophysical effect selected from:
        i. a biological effect,
        ii. a chemical effect,
        iii. a pharmacological effect,
        iv. a pharmacological interaction between the compounds within the subset of compounds,
        v. a toxicity to each individual compound or the subset of compounds,
        vi. an immune response to each individual compound or the subset of compounds, and
        vii. a combination thereof;
    b. a synergistic effect between two or more compounds,
    c. an antagonistic effect between two or more compounds; and
    d. a combination thereof.

4. The method of claim 1, wherein the corresponding set of compounds is selected from an oligonucleotide-based medicine (OBM), a small molecule, a polypeptide comprising an antibody or an antibody-binding fragment, and a combination thereof.

5. The method of claim 1, wherein the association comprises quantitative mapping between the effects is the interaction between each of the plurality of compounds that produce a positive or negative biophysical effect on the safety or efficacy of the combined compounds.

6. The method of claim 5, wherein the interaction is a chemical interaction, a molecular interaction, a toxic interaction, a synergistic or antagonistic interaction, or a combination thereof.

7. The method of claim 1, wherein the subject is a mammal or a rodent.

8. The method of claim 1, wherein steps a)-b) are repeated until a threshold criteria is satisfied by the iteratively updated trained compound experiment model based on one or more desired effects.

* * * * *